(12) United States Patent
Hall et al.

(10) Patent No.: US 6,436,627 B1
(45) Date of Patent: Aug. 20, 2002

(54) GENE ENCODING AN INVERTEBRATE α1 CALCIUM CHANNEL SUBUNIT

(75) Inventors: Linda M. Hall, Williamsville; Celian Ren, Buffalo, both of NY (US); Wei Zheng, Lafayette, CA (US); Manuel Marcel Paul Dubald, Chapel Hill, NC (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/539,879

(22) Filed: Mar. 31, 2000

Related U.S. Application Data

(60) Division of application No. 09/111,865, filed on Jul. 8, 1998, now abandoned, which is a continuation-in-part of application No. 08/374,077, filed on Jan. 19, 1995, now Pat. No. 6,027,912.

(51) Int. Cl.$^7$ .......................... C12P 21/06; C12Q 3/00; C07H 21/02
(52) U.S. Cl. ........................ 435/3; 435/69.1; 435/52.3; 435/254.11; 435/320.1; 536/23.1; 536/23.5
(58) Field of Search ........................ 435/69.1, 3, 252.3, 435/254.11, 320.1; 536/23.1, 23.5

(56) References Cited

PUBLICATIONS

Snutch et al., "Rat Brain Expresses a heterogeneous Family of Calcium Channels", *Proc. Natl. Acad. Sci. USA*, (1990) 87:3391–3395.

Snutch et al., "Distinct Calcium Channels Are Generated by Alternative Splicing and Are Differentially Expresses in the Mammalian CNS", *Neuron*, (1991) 7:45–57.

Hui et al, "Molecular Cloning of Multiple Subtypes of a Novel Rat Brain Isoform of the $\alpha_1$ Subunit of the Voltage–Dependent Calcium Channel", *Neuron*, (1991) 7:35–44.

Starr et al., "Primary Structure of a Calcium Channel That is Highly Expressed in the Rat Cerebellum", *Proc. Natl. Acad. Sci. USA*, (1991) 88:5621–5625.

Dubel et al., "Molecular cloning of the $\alpha_1$ subunit of an ω–conotoxin–sensitive calcium channel", *Proc. Natl. Acad. Sci. USA*, (1992) 89:5058–5062.

Soong et al., "Structure and Functional Expression of a Member of the Low–Voltage–Activated Calcium Channel Family", *Science*, (1993) 260:1133–1136.

Biel et al., "Primary structure and functional expression of a high voltage activated calcium channel from rabbit lung", *FEBS Lett.*, (1990) 269:409–412.

Koch et al., "cDNA Cloning of a Dihydropyridine–sensitive Calcium Channel from Rat Aorta", *J. Biol. Chem.*, (1990) 265:17786–17791.

Perez–Reyes et al., "Molecular Diversity of L–type Calcium Channels", *J. Biol. Chem.*, (1990) 265:20430–20436.

Williams et al., "Structure and Functional Expression of an ω–Conotoxin–Sensitive Human N–Type Calcium Channel", *Science*, (1992a) 257:389–395.

Williams et al., "Structure and Functional Expression of $\alpha_1$, $\alpha_2$ and β Subunits of a Novel Human Neuronal Calcium Channel Subtype", *Neuron*, (1992b) 8:71–84.

ffrench–Constant et al., "Molecular cloning and transformation of cyclodiene resistance in Drosophila: An invertebrate γ–aminobutyric acid subtype A receptor locus", *Proc Natl. Acad. Sci. USA* (1991) 88:7209–7213.

ffrench–Constant et al., "A point mutation in a Drosophila GABA receptor confers insecticide resistance", *Nature*, (1993) 363:449–451.

Harvey et al., "Sequence of a functional invertebrate $GABA_A$ receptor subunit which can form a chimeric receptor with a vertebrate α subunit", *EMBO J.*, (1991) 10:3239–3245.

Ruth et al., "Primary Structure of the β Subunit of the DHP–Sensitive Calcium Channel from Skeletal Muscle", *Science* (1989) 245:1115–1118.

Pragnell et al., "Calcium channel β–subunit binds to a conserved motif in the I–II cytoplasmic linker of the $\alpha_1$–subunit", *Nature* (1994) 368:67–70.

Tanabe et al., "Primary structure of the receptor for calcium channel blockers from skeletal muscle", *Nature*, (1987) 328:313–318.

Mikami et al., "Primary structure and functional expression of the cardiac dihydropyridine–sensitive calcium channel", *Nature*, (1989) 340:230–233.

Mori et al., "Primary structure and functional expression from complementary DNA of a brain calcium channel", *Nature*, (1991) 350:398–402.

Grabner et al., "Calcium channels from *Cyprinus carpio* skeletal muscle", *Proc. Natl. Acad. Sci. USA*, (1991) 88:727–731.

Martin et al., "Base pairing involving deoxyinosine: implications for probe design", *Nucleic Acids Res.*, (1985) 13:8927.

Knoth et al., "Highly degenerate, inosine–containing primers specifically amplify rare cDMA using the polymerase chain reaction", *Nucleic Acids Res.*, (1988) 16:11932.

Pauron et al., "Identification and affinity Labeling of Very High Affinity Binding Sites for the Phenylalkylamine Series of $Ca^+$ Channel Blockers in the Drosophila Nervous System", *Biochemistry*, (1987) 26:6311–6315.

(List continued on next page.)

*Primary Examiner*—Karen Cochrane Carlson
*Assistant Examiner*—Stephen Tu
(74) *Attorney, Agent, or Firm*—Burns, Doane, Swecker & Mathis, L.L.P.

(57) ABSTRACT

The present invention provides for the isolation and characterization of a calcium channel α, subunit gene cloned from *Drosophila melanogaster*, and designated "DmcalD" ... an invertebrate calcium channel subunit gene.

14 Claims, 30 Drawing Sheets

OTHER PUBLICATIONS

Greenberg et al., "Native and Detergent–Solubilized Membrane Extracts From Drosophila Heads Contain Binding Sites for Phenylalkylamine Calcium Channel Blockers", *Insect Biochem.*, (1989) 19:309–322.

Pelzer et al., Diversity and novel pharmacological properties of $Ca^{2+}$ channels in Drosophila brain membranes, *EMBO J.*, (1989) 8:2365–2371.

Glossmann et al., "Very high affinity interaction of DPI 201–106 and BDF 8784 enantiomers with the phenylalkylamine–sensitive $Ca^{2+}$–channel in Drosophila head membranes", *Br. J. Pharmacol.*, (1991) 102:446–452.

Babitch, J., "Channel Hands", *Nature*, (1989) 346:321–322.

Stühmer et al., Structural parts involved in activation and inactivation of the sodium channel, *Nature*, (1989) 339:597–603.

Tufty, R. M. and Kretsinger, R. H. "Troponin and Parvalbumin Calcium Binding Regions Predicted in Myosin Light Chain and T4 Lysozyme", *Science*, (1975) 187:167–169.

Tang et al., "Molecular Localization of Ion Selectivity Sites within the Pore of a Human L–type Cardiac Calcium Channel", *J. Biol. Chem.*, (1993) 268:13026–13029.

Tanabe et al., "Regions of the skeletal muscle dihydropyridine receptor critical for excitation–contraction coupling", *Nature*, (1990) 346:567–569.

Striessnig et al., "Identification of a phenylalkylamine binding region within the α1 subunit of skeletal muscle $Ca^{2+}$ channels", *Proc. Natl. Acad. Sci. USA*, (1990) 87:9108–9112.

Nakayama et al., "Identification of 1,4–dihydropyridine binding regions within the α1 subunit of skeletal muscle $Ca^{2+}$ channels by protoaffinity labeling with diazipine", *Proc. Natl. Acad. Sci. USA*, (1991) 88:9203–9207.

Striessnig et al., Dihydropyridine receptor of L–type $Ca^{2+}$ channels: Identification of binding domains for [3H](+)–PN200–110 and [3H]azidopine within the α1 subunit, *Proc. Natl. Acad. Sci. USA*, (1991) 88:10769–10773.

Catterall, W. A. and Striessnig, J., "Receptor sites for $Ca^{2+}$ channel antagonists", TIPS, (1992) 13:256–262.

J.R. Thackery and B. Ganetzky, "Developmentally Regulated Alternative Splicing Generates a Complex Array of *Drosophila para* Sodium Channel Isoforms", *J. Neurosci*, (1994) 14:2569–2578.

Hullin et al, "Calcium channel β subunit heterogeneity: functional expression of cloned cDNA from heart, aorta and brain", *EMBO J.* 11–885–890.

Perez–Reyes et al, "Cloning and Expression of a Cardiac/Brain β Subunit of the L–type Calcium Channel", *J. Biol. Chem.* (1992) 267:1792–1797.

Pragnell et al, "Cloning and tissue–specific expression of the brain calcium channel β–subunit" *FEBS Lett.* 291:253–258.

Harpold et al, "Structure and Functional Expression of $α_1$, $α_2$ and Subunits of a Novel Human Neuronal Calcium Channel Subtype", *Neuron* (1992) 8:71–84.

Grabner et al., "Cloning and Functional Expression of a Neuronal Calcium Channel β Subunit from House Fly (*Musca domestica*)*", *J. Biol. Chem.* 269(38):23668–23674.

Williams et al., "Structure and Functional Expression of $α_1$, $α_2$, and β Subunits of a Novel Human Neuronal Calcium Channel Subtype", *Neuron* 8:71–84 (1992).

Grabner et al., "Molecular Cloning of an $α_1$–Subunit from Housefly (*Musca domestica*) muscle", *FEBS letters* 339:189–194 (1994).

Matthews et al., "Molecular Cloning and Genomic Mapping of a Calcium Channel $α_1$ Subunit From *Caenorhabditis elegans* E.", *Soc Neuroscience Abstr.* 20:69 (1994).

Zheng et al., "Cloning and Characterization of a Novel $α_1$ Subunit of Drosophila $Ca^{2+}$ Channel", *Soc. Neuroscience Abstr* 18:1138 (1992).

Pelzer et al., "Diversity and Novel Pharmacological Properties of $Ca^{2+}$ Channels in Drosophila Brain Membranes", *EMBO J.* 8:2365–2371 (1989).

Takeshima et al., "Isolation and Characterization of a Gene for a Ryanodine Receptor/Calcium Release Channel in *Drosophia melanogaster*", *FEBS Letters* 337:81–7, 1994.

```
MGGGELVNCI  AYDDNTLVIE  RKPSPSSPST  SRRYLKAETP  TRGSRKYNRK    50
SSAKSDLEVV  VVKPEHHHQH  RSPTITLPVP  ANPLTTSASA  GSSPTGAGLA   100
AGLGTASGTV  LQQSCSALDP  PEDSNQPSGT  RRRATSTELA  LSNVTSQIVN   150
NATYKLDFKQ  RRHKSNNGGS  ESGSLTGIAT  GPATSPAGPT  GPTSSSGKRR   200
KSSCTSCGGG  GISAPPPRLT  PEEAWQLQPQ  NSVTSAGSTN  SSFSSGGGRD   250
DNSSYSAVGG  DSSSSNSCNC  DITGDNSTLH  GLGVGDVCSF  IADCDDNSED   300
DDGDPNNQDL  SSQTLRTAAI  VAAVAAAAKE  QAQEQSLADC  ESFSDRRQDA   350
DEDVRIIQDC  CGGNNDSLED  VGEVDDNADV  VVRKNSRNRP  SIRRTCRITE   400
EDDDEDENAD  YGDFDREDQE  LDDEEPEGTT  IDIDEQEQQH  DQGDSAEEED   450
DDEDVDEYFE  EEEDDTQAFS  PFYSSSAELI  DNFGGGAGKF  FNIMDFERGA   500
SGEGGFSPNG  NGGPGSGDVS  RTARYDSGEG  DLGGGNNIMG  IDSMGIANIP   550
ETMNGTTIGP  SGAGGQKGGA  AAGAAGQKRQ  QRRGKPQPDR  PQRALFCLSV   600
KNPLRALCIR  IVEWKPFEFL  ILLTIFANCI  ALAVYTPYPG  SDSNVTNQTL   650
EKVEYVFLVI  FTAECVMKIL  AYGFVLHDGA  YLGNGWNLLD  FTIVVMGAIS   700
TALSQLMKDA  FDVKALRAFR  VLRPLRLVSG  VPSLQVVLNS  ILKAMVPLFH   750
IALLVLFVII  IYAIIGLELF  SGKLHKACRD  EITGEYEENI  RPCGVGYQCP   800
PGYKCYGGWD  GPNDGITNFD  NFGLAMLTVF  QCVTLEGWTD  VLYSIQDAMG   850
SDWQWMYFIS  MVILGAFFVM  NLILGVLSGE  FSKERNKAKN  RGDFQKLREK   900
QQIEEDLRGY  LDWITQAEDI  EPDAVGGLIS  DGKGKQPNEM  DSTENLGEEM   950
PEVQMTESRW  RKMKKDFDRV  NRRMRRACRK  AVKSQAFYWL  IIVLVFLNTG  1000
VLATEHYGQL  DWLDNFQEYT  NVFFIGLFTC  EMLLKMYSLG  FQGYFVSLFN  1050
RFDCFVVIGS  ITETLLTNTG  MMPPLGVSVL  RCVRLLRVFK  VTKYWRSLSN  1100
LVASLLNSIQ  SIASLLLLLF  LFIVIFALLG  MQVFGGKFNF  DGKEEKYRMN  1150
FDCFWQALLT  VFQIMTGEDW  NAVMYVGINA  YGGVSSYGAL  ACIYFIILFI  1200
CGNYILLNVF  LAIAVDNLAD  ADSLSEVEKE  EEPHDESAQK  KSHSPTPTID  1250
GMDDHLSIDI  DMEQQELDDE  DKMDHETLSD  EEVREMCEEE  EEVDEEGMIT  1300
ARPRRMSEVN  TATKILPIPP  GTSFFLFSQT  NRFRVFCHWL  CNHSNFGNII  1350
LCCIMFSSAM  LAAENPLRAN  DDLNKVLNKF  DYFFTAVFTM  ELILKLISYG  1400
FVLHDGAFCR  SAFNLLDLLV  VCVSLISLVS  SSDAISVVKI  LRVLRVLRPL  1450
RAINRAKGLK  HVVQCVIVAV  KTIGNIVLVT  CLLQFMFAVI  GVQLFKGKFF  1500
KCTDGSKMTQ  DECYGTYLVY  DDGDVHKPRL  REREWSNNRF  HFDDVAKGML  1550
TLFTVSTFEG  WPGLLYVSID  SNKENGGPIH  NFRPIVAAYY  IIYIIIIAFF  1600
MVNIFVGFVI  VTFQNEGEQE  YKNCDLDKNQ  RNCIEFALKA  KPVRRYIPKH  1650
GIQYKVWWFV  TSSSFEYTIF  ILIMINTVTL  AMKFYNQPLW  YTELLDALNM  1700
IFTAVFALEF  VFKLAAFRFK  NYFGDAWNVF  DFIIVLGSFI  DIVYSEIKSK  1750
DTSQIAECDI  VEGCKSTKKS  AGSNLISINF  FRLFRVMRLV  KLLSKGEGIR  1800
TLLWTFIKSF  QALPYVALLI  VLLFFIYAVV  GMQVFGKIAL  DGGNAITANN  1850
NFQTFQQAVL  VLFRSATGEA  WQEIMMSCSA  QPDVKCDMNS  DTPGEPCGSS  1900
IAYPYFISFY  VLCSFLIINL  FVAVIMDNFD  YLTRDWSILG  PHHLDEFIRL  1950
WSEYDPDAKG  RIKHLDVVTL  LRKISPPLGF  GKLCPHRMAC  KRLVSMNMPL  2000
NSDGTVLFNA  TLFAVVRTSL  SIKTDGNIDD  ANSELRATIK  QIWKRTNPKL  2050
LDQVVPPPGN  DDEVTVGKFY  ATYLIQDYFR  RFKKRKEQEG  KEGHPDSNTV  2100
TLQAGLRTLH  EVSPALKRAI  SGNLDELDQE  PEPMHRRHHT  LFGSVWSSIR  2150
RHGNGTFRRS  AKATASQSNG  ALAIGGSASA  ALGVGGSSLV  LGSSDPAGGD  2200
YLYDTLNRSV  ADGVNNITRN  IMQARLAAAG  KLQDELQGAG  SGGELRTFGE  2250
SISMRPLAKN  GGGAATVAGT  LPPEANAINY  DNRNRGILLH  PYNNVYAPNG  2300
ALPGHERMIQ  STPASPYDQR  RLPTSSDMNG  LAESLIGGVL  AAEGLGKYCD  2350
SEFVGTAARE  MREALDMTPE  EMNLAAHQIL  SNEHSLSLIG  SSNGSIFGGS  2400
AGGLGGAGSG  GVGGLGGSSS  IRNAFGGSGS  GPSSLSPQHQ  PYSGTLNSPP  2450
IPDNRLRRVA  TVTTTNNNNK  SQVSQNNSSS  LNVRANANSQ  MNMSPTGQPV  2500
QQQSPLRGQG  NQTYSSX                                         2517
```

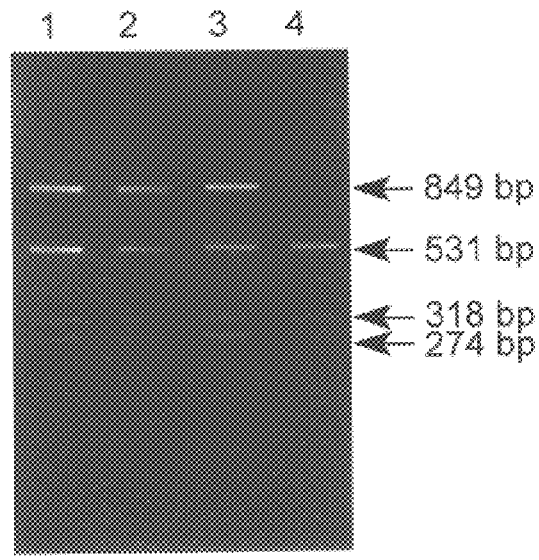
FIG. 10A
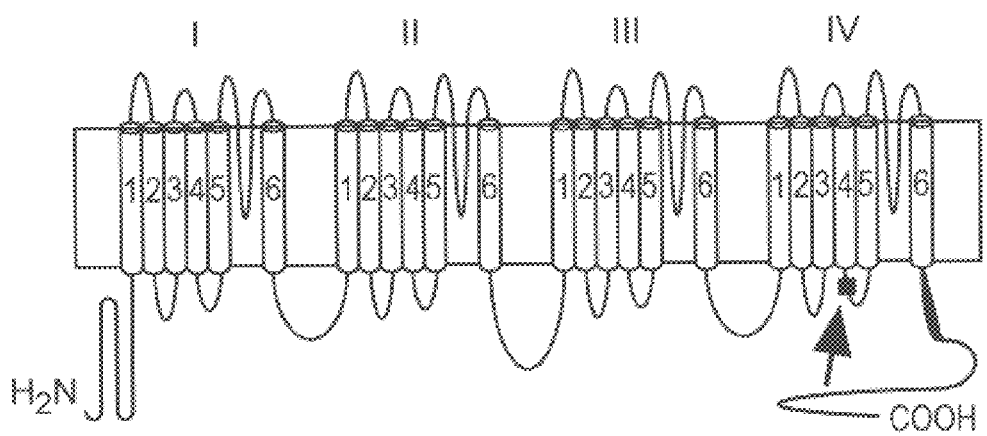
FIG. 10B
FIG. 10C

Dihydropyridines
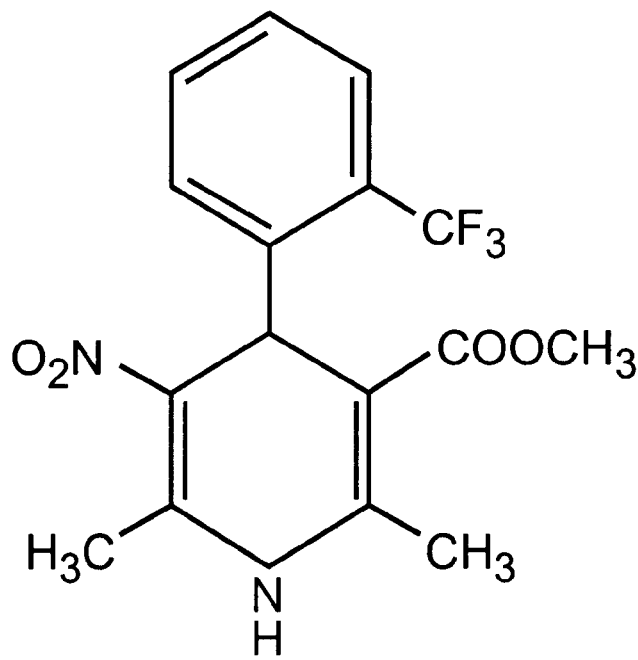
Agonist
Bay K 8644
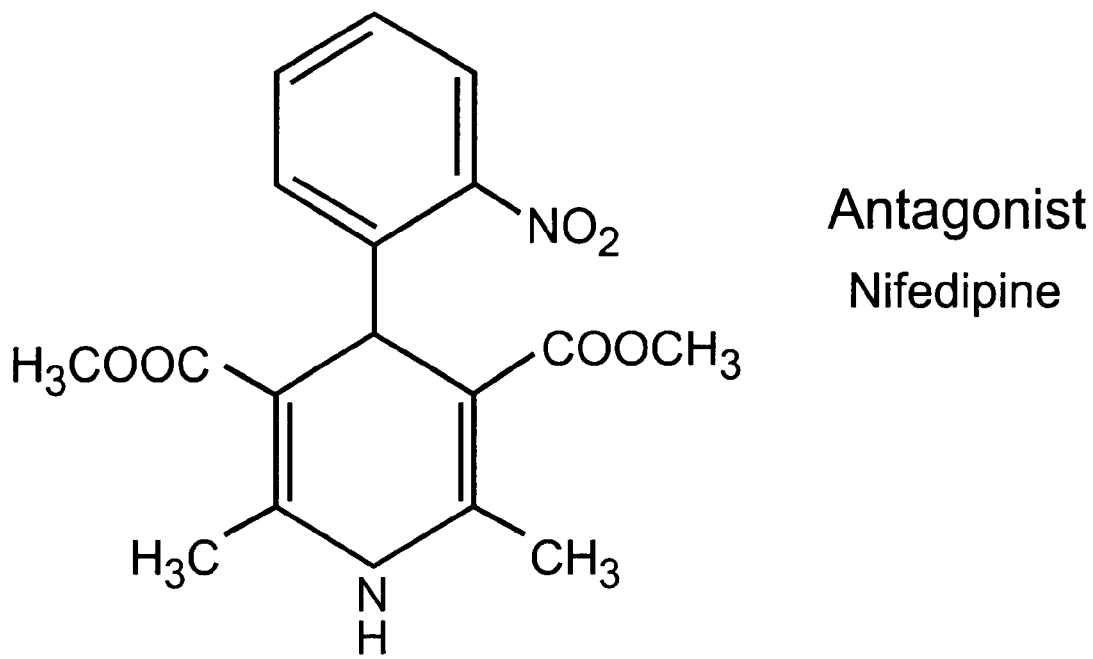
Antagonist
Nifedipine
FIG. 22

FIG. 23

Dihydropyridine Binding Regions on α₁ Subunits

```
                    IIIS6
                         *       *
         C     ISIFFIIIYIIIIAFFMMNIFVGFVIV   (1169)
         S     MAIFFIIIYIIILIAFFMMNIFVGFVIV  (1065)      DHP sensitive
         D     ISIFFIIIYIIIVAFFMMNIFVGFVIV   (1151)
   Carp Sk    ISIFFIIIYIIIIAFFMMNIFVGFVIV    (1172)
     Dmca1D   (V)A(A)(Y)(Y)IIIYIII IAFFM(V)NIFVGFVIV  (1610)
       Con+   ......IIIYIII..AFFM. NIFVGFVIV Con-   .SIFYVVYFVVFPFFFVNIFVALIII      (1520)
         A    MSIFYVVYFVVFPFFFVNIFVALIII     (1417)      DHP insensitive
         B    LSIFYVVYFVVFPFFFVNIFVALIII     (1413)
         E    MSIFYVVYFVVFPFFFVNIFVALIII
     Dmca1A   VSIFYIVYFIVFPFFFVNIFVALIII IVS6
                    ■   *     **
         C    AVFYFISFYMLCAFLIINLFVAVIM      (1478)
         S    AYYYFISFYMLCAFLIINLFVAVIM      (1380)      DHP sensitive
         D    AIVYFISFYILCAFLIINLFVAVIM      (1462)
    Carp Sk   AVFYFLSFYILCAFLIINLFVAIIM      (1482)
     Dmca1D   AY(P)YFISFY(V)LC(S)FLIINLFVAVIM   (1926)
       Con+   A.. YF.SFY.LC.FLIINLFVAVIM Con-   AY.YFVSFIF.CSFLMLNLFVAVIM      (1819)
         A    AYFYFVSFIFLCSFLMLNLFVAVIM      (1707)      DHP insensitive
         B    AYFYFVSFIFLCSFLMLNLFVAVIM      (1712)
         E    AYVYFVSFIFFCSFLMLNLFVAVIM
     Dmca1A   AYAYFVSFIFFCSFLMLNLFVAIM
```

* This residue when mutated caused decreased affinity for both antagonist and agonist.

■ This residue when mutated caused increased affinity for antagonist, but had no effect on agonist affinity.

■ Mutation of Y had no effect on either antagonist or agonist affinity. Mutation of M decreased antagonist affinity without affecting agonist affinity. When both Y & M were changed, antagonist affinity decreased and agonist interaction was abolished.

☐ Tested residue: mutation led to decreased antagonist affinity; agonist interaction not checked unless there is a ■ symbol on top of the bar.

☐ Tested residue: mutation led to no effect on antagonist affinity; agonist interaction not checked.

GENE ENCODING AN INVERTEBRATE α1 CALCIUM CHANNEL SUBUNIT

CROSS-REFERENCE TO RELATED APPLICATIONS

This application is a divisional, of application Ser. No. 09/111,865 filed Jul. 8, 1998, now abandoned which is a continuation-in-part of application Ser. No. 08/374,077, filed Jan. 19, 1995 now U.S. Pat. No. 6,027,912.

FIELD OF THE INVENTION

The present invention relates generally to the voltage-dependent calcium channel multigene family. More particularly, the present invention relates to the characterization and isolation of a neuronal invertebrate calcium channel $\alpha_1$ subunit from *Drosophila melanogaster*.

BACKGROUND OF THE INVENTION

Early electrophysiological studies on invertebrate preparations revealed the presence of calcium currents and suggested the presence of multiple types of voltage-dependent calcium channels (reviewed by Hille, B., (1992), In: Ion Channels of Excitable Membranes, 2nd Ed., Sinauer, Sunderland, Mass.). Continuing studies of calcium channels have shown that they are ubiquitous since they are found in excitable cells in species ranging from Paramecium to humans. Calcium channels are involved in many cell functions including: membrane excitability, synaptic transmission, and differentiation (Tsien et al., (1988), *Trends Neurosci.*, vol. 11, pp. 431–438). Voltage-dependent calcium channels have been studied extensively in vertebrate neuronal tissue using electrophysiological and pharmacological approaches and as a result have been divided into four classes designated L, N, T, and P (Bean, B. P., (1989), *Ann. Rev. Physiol.*, vol. 51, pp. 367–384; Hess, P., (1990), *Ann. Rev. Neurosci.*, vol. 13, pp. 1337–1356).

Gene cloning studies, which up to this point have focused exclusively on vertebrate species, have helped to elucidate the molecular nature of calcium channel structure and have suggested a remarkable degree of channel heterogeneity beyond that predicted from physiological and pharmacological approaches. This molecular diversity of calcium channels arises from several mechanisms. Calcium channels are comprised of multiple subunits designated $\alpha_1$, $\alpha_2$, $\beta$, $\gamma$, and $\delta$ (Catterall, W. A., (1991a), *Cell*, vol. 64, pp. 871–874; Catterall, W. A., (1991b), *Science*, vol. 253, pp.1499–1500). The ($\alpha_2$ and $\partial$ subunits are encoded by the same gene and are cleaved during post-translational processing whereas each of the other subunits arise from different genes. One way that calcium channel diversity arises is through the presence of a family of genes each encoding genetic variants of a given subunit. For example, in rat brain the $\alpha_1$ subunit appears to be encoded by a family of at least five different genes (Snutch et al., (1990), *Proc. Natl. Acad. Sci. USA*, vol. 87, pp. 3391–3395; Snutch et al., (1991), *Neuron*, vol. 7, pp. 45–57; Hui et al., (1991), *Neuron*, vol. 7, pp. 35–44; Starr et al., (1991), *Proc. Natl. Acad. Sci. USA*, vol. 88, pp. 5621–5625; Dubel et al., (1992) *Proc. Natl. Acad. Sci. USA*, vol. 89, pp. 5058–5062; Soong et al. (1993), *Science*, vol. 260, pp. 1133–1136). For each member the gene family further diversity is introduced by alternative splicing (Biel et al., (1990), *FEBS Lett.*, vol. 269, pp. 409–412; Koch et al., (1990), *J. Biol. Chem.*, vol. 265, pp. 17786–17791; Perez-Reyes et al., (1990), J. Biol. Chem., vol. 265, pp. 20430–20436; Snutch et al., (1991), *Neuron*, vol. 7, pp. 45–57). Recent studies point to the existence of similar molecular diversity for the other subunits as well (Williams et al., (1992a), *Science*, vol. 257, pp. 389–395; Williams et al., (1992b), *Neuron*, vol. 8, pp. 71–84). If each subunit variant can interact with more than one form of each of the other subunits to form functional channels, then there is a potential for even further molecular diversity.

Although studies of the molecular diversity of calcium channels in Drosophila are just beginning, there is evidence for structural and functional heterogeneity in this system. Binding of phenylalkylamines (calcium channel blocking agents) to Drosophila head extracts showed curvilinear Scatchard plots indicative of multiple classes differing in ligand affinity (Greenberg et al. (1989), *Insect Biochem.*, vol. 19, 309–322). Pelzer et al., (1989), *EMBO J.*, vol. 8, pp. 2365–2371, reported at least 8 distinct voltage-sensitive calcium channels in Drosophila head membranes following reconstitution into phospholipid bilayers. Patch clamp studies on cultured embryonic Drosophila myocytes and neurons also showed variability of channel properties, suggesting at least two types of calcium channels in Drosophila (Leung and Byerly, 1991). Further evidence for channel heterogeneity comes from differential sensitivity of Drosophila calcium channels to a purified toxin from the spider *Hololena curta* (Leung, H. T. and Byerly, L., (1991), *J. Neurosci.*, vol. 11, pp. 3047–3059). This heterogeneity is further supported in another neuronal invertebrate (*Periplaneta americana*) where radiotracer flux studies have demonstrated the presence of dihydropyridine-insensitive and -sensitive components of phenylalkylamine-sensitive calcium uptake in nervous system and skeletal muscle membranes, respectively (Skeer et al., (1992), *Insect Biochem Molec. Biol.*, vol. 22, pp. 539–545).

Given the heterogeneity of calcium channels in invertebrates, Drosophila provides an ideal system for a molecular genetic approach to define the significance of channel diversity by mutating individual subunit genes and determining the physiological and behavioral consequences.

Other ion channels have also been reported to date. For example, electrophysiological studies of ligand-gated ion currents in invertebrate nerve and muscle cells provide evidence for the existence of chloride channels gated by glutamate, histamine, and taurine, as well as those gated by y-aminobutyric acid ("GABA") (Sattelle, D. B., (1990), *Adv. Insect Physiol.*, vol. 22, pp. 41–56 and Lummis et al., (1990), *Annu. Rev. Entomol.*, vol. 35, pp. 345–377). Although these findings imply the existence of a large and diverse gene family encoding ligand-gated chloride channels in invertebrates, very little is known about homologous channels of invertebrates. In French-Constant et al., (1991), *Proc Natl. Acad. Sci. USA*, vol. 88, pp. 7209–7213, a *Drosophila melanogaster* cDNA having significant predicted amino acid sequence identity to vertebrate ligand-gated chloride channel genes was isolated and mapped to a genetic locus ("Rdl") that confers resistance to cyclodiene insecticides and other blockers of GABA-gated chloride channels. Rdl was shown to encode a GABA subunit by the expression of functional homomultimeric GABA receptors in *Xenopus* oocytes following injection with RD1 mRNA (French-Constant et al., (1993), *Nature*, vol. 363, pp. 449–451).

The only other example of a ligand-gated chloride channel gene from an invertebrate species is a GABA receptor β-like subunit gene isolated from the pond snail, *Lymnaea stagnalis* (Harvey et al., (1991), *EMBO J.*, vol. 10, pp. 3239–3245). The functional relationship of the product encoded by this gene to vertebrate GABA receptor β subunits was corroborated by the formation of a functional chimeric receptor with properties similar to vertebrate α/β heteromultimers when the gene was co-expressed with a vertebrate a subunit in Xenopus oocytes.

The characterization and isolation of a neuronal invertebrate $α_1$ calcium channel subunit gene(s) would be useful in the cloning of calcium channel subunits from other invertebrate preparations of physiological or economic importance for purposes such as screening chemical agents to identify chemical agents which specifically interact with, and bind to, the calcium channel receptor on the surface of a cell, such as, for example, organic calcium channel blocking agents, e.g., phenylalkylamines.

SUMMARY OF THE INVENTION

A major object of the present invention is the isolation and characterization of an invertebrate neuronal calcium channel $α_1$ subunit gene(s).

The present invention provides for the isolation of genomic DNA fragments from Drosophila melanogaster which encode a conserved amino acid sequence unique to the voltage-dependent calcium channel multigene family. Polymerase chain reaction ("PCR")-based homology and screening of cDNA libraries with homologous probe were utilized to isolate the genomic DNA fragments of the invention. Using PCR, the first neuronal invertebrate calcium channel subunit gene was cloned. That is, the neuronal calcium channel $α_1$ subunit gene was cloned from Drosophila melanogaster, and designated herein as "DmcalD". The CDNA clones corresponding to the DNA fragments are designated N1, W8A, SH22C, and SH22D.

The DNA sequence expressing the corresponding amino acid sequences encoding the calcium channel $α_1$ subunit gene(s) of the invention can be cloned into any suitable expression vector, such as, for example, plasmid DNA, viral DNA including human viruses, animal viruses and invertebrate V4 ruses and bacteriophages to form a recombinant expression system which directs the expression of the calcium channel $α_1$ subunit of the invention. It is understood that this expression system can be expressed in any suitable host cell to form a functional recombinant calcium channel receptor.

In another aspect of the invention, there is provided a method of expressing a functional neuronal invertebrate $α_1$ calcium channel receptor comprising (a) transforming a host cell with the gene of the present invention e.g., gene encoding the neuronal calcium channel $α_1$ subunit from Drosophila melanogaster, and (b) facilitating expression of the gene(s) in the host cell, thereby forming a functional ion channel receptor which exhibits similar pharmacological properties of calcium channel in neuronal invertebrate tissue.

In still another aspect of the invention, there is provided a method of screening a chemical agent for effectiveness as a pesticide, comprising (a) facilitating expression of the gene of the invention e.g., gene encoding the calcium channel $α_1$ subunit from Drosophila melanogaster, in a host thereby forming a functional calcium channel receptor, (b) exposing the host to a chemical agent having pesticidal activity, and (c) evaluating the exposed host to determine if the functional calcium channel receptor is the target site for the pesticidal activity of the chemical agent.

In still a further aspect of the invention, there is provided a method of identifying compositions which specifically interact with, and bind to, the calcium channel receptor on the surface of a cell comprising (a) contacting a vertebrate or invertebrate cell containing the gene of the invention e.g., gene encoding the calcium channel $α_1$ subunit from Drosophila melanogaster, with a plurality of chemical agents, and (b) determining those chemical agents which bind to the calcium channel expressed in the cell, thereby identifying chemical agents which specifically interact with, and bind to, the channel.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIG. 1 is a schematic diagram depicting a strategy for cloning and the relationship of cDNA clones encoding the neuronal calcium channel $α_1$ subunit from Drosophila.

Figure 2A-1:
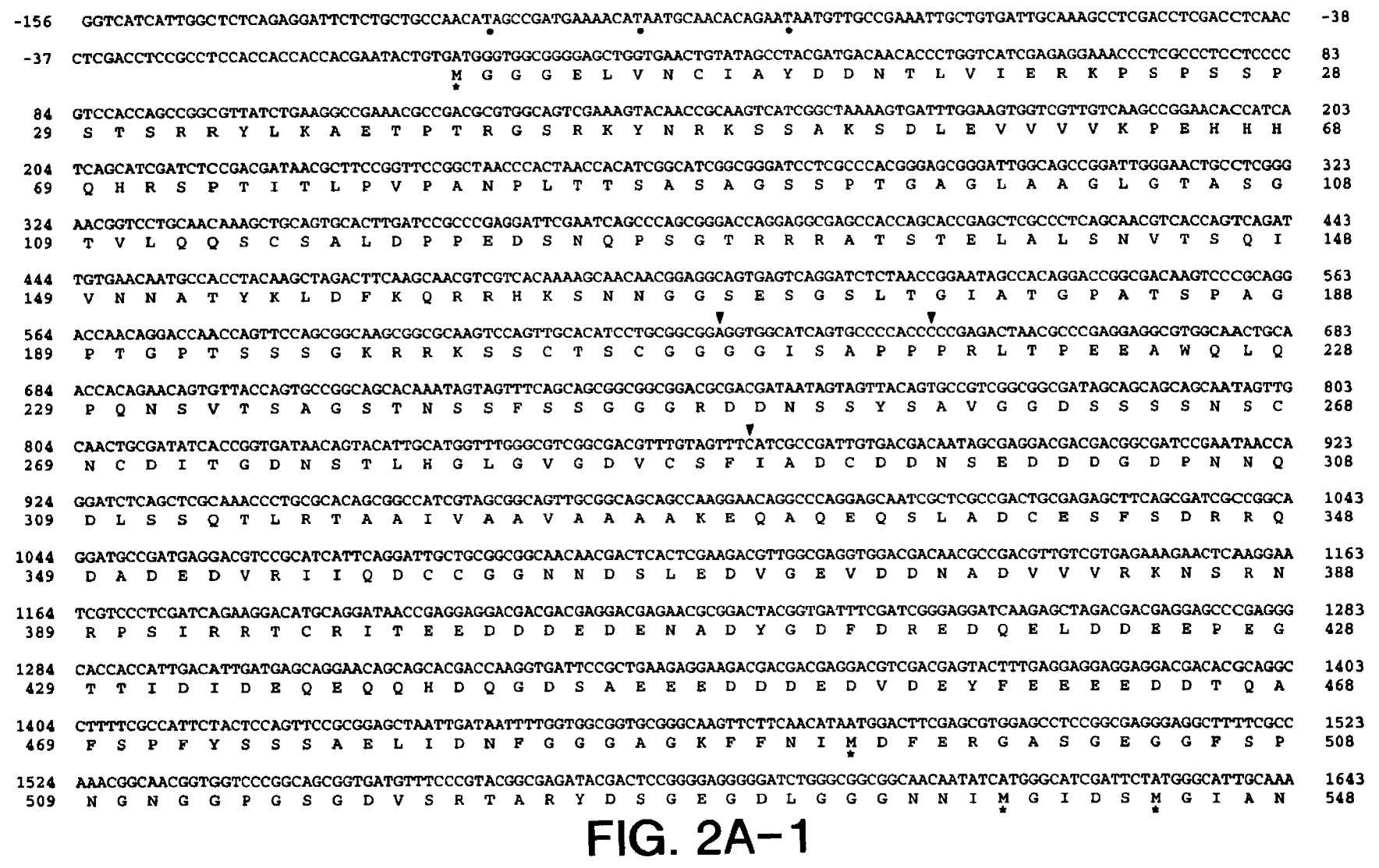
Figure 2A-2:
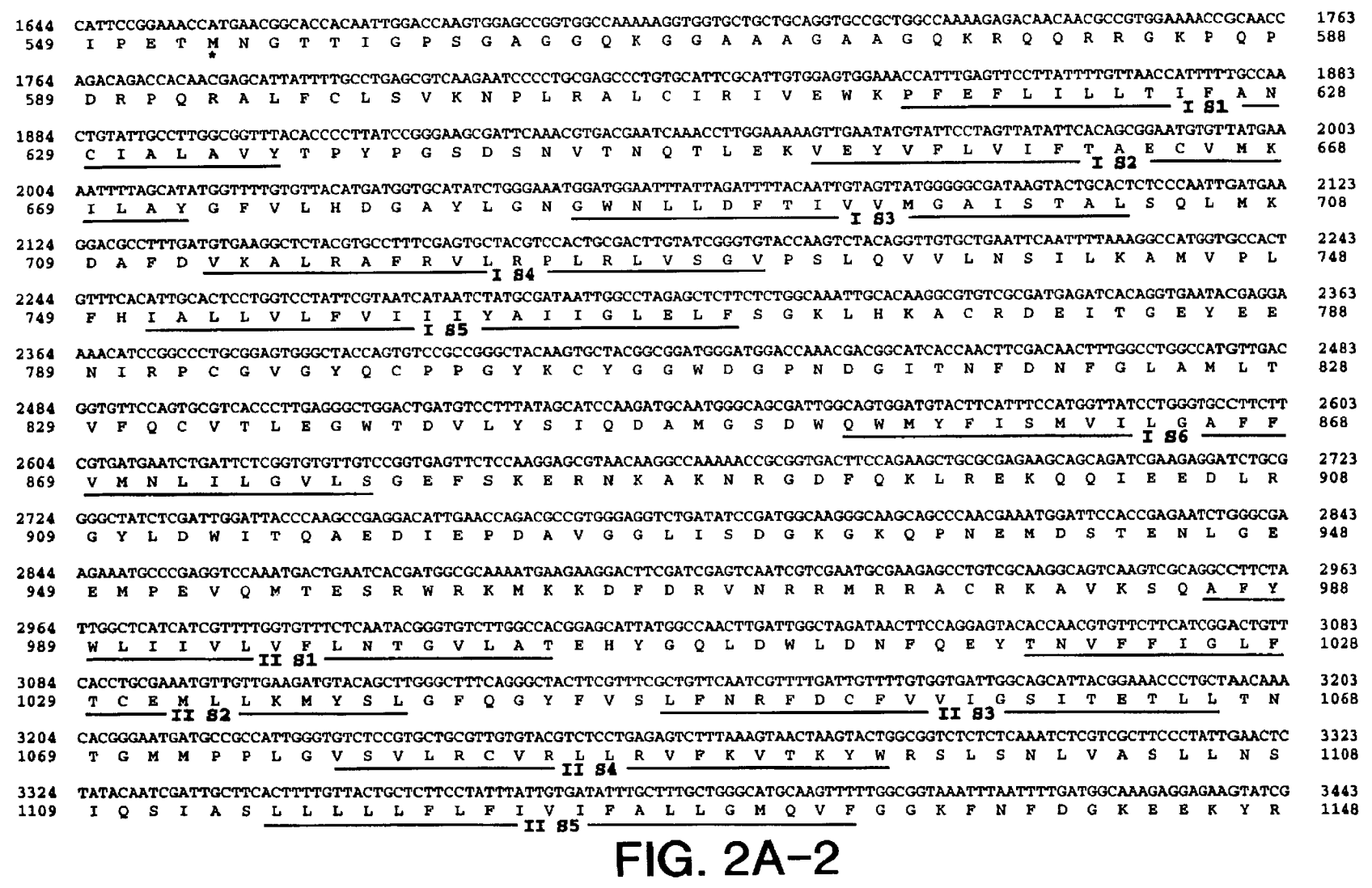
Figure 2A-3:
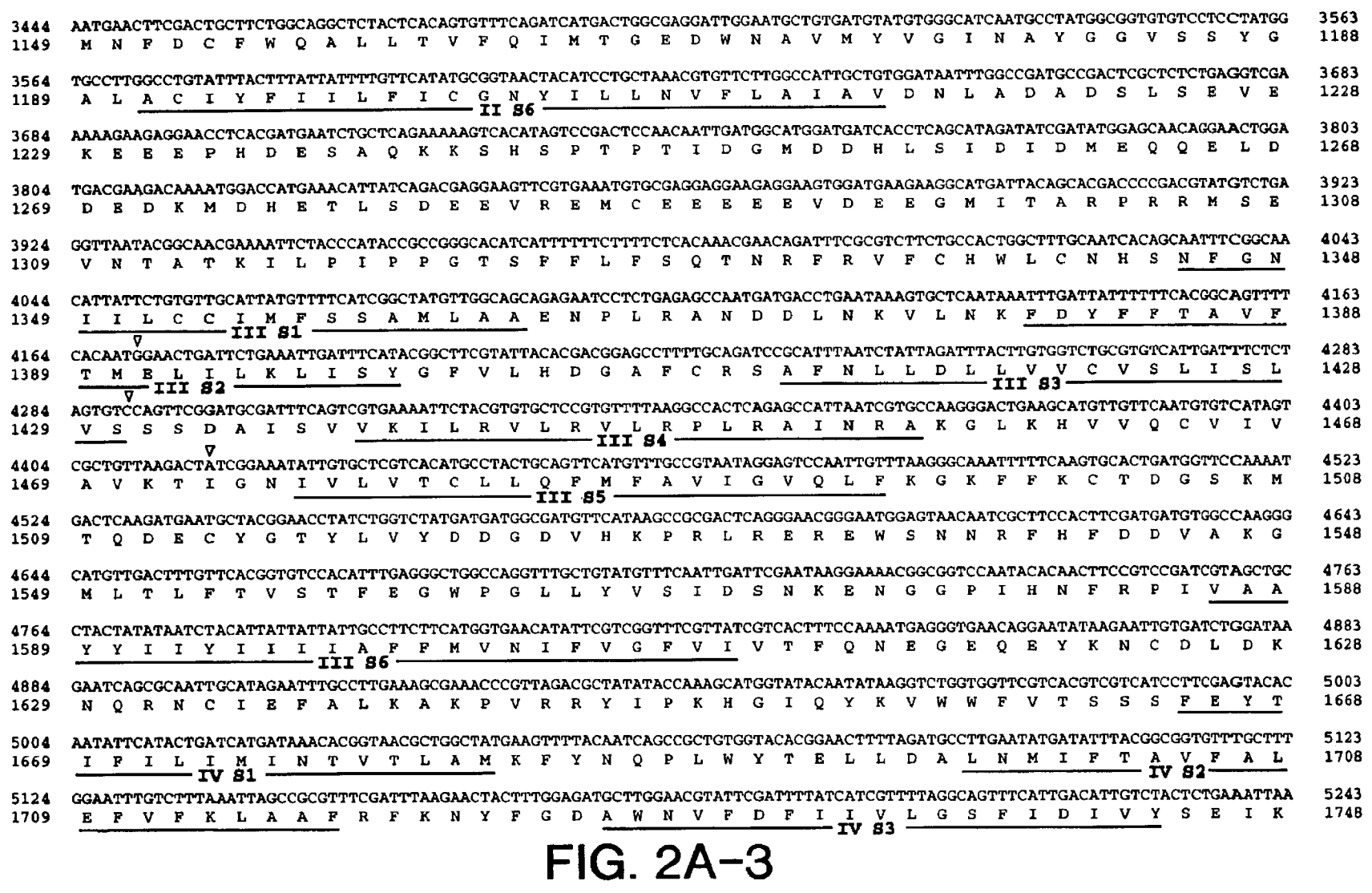
Figure 2A-4:
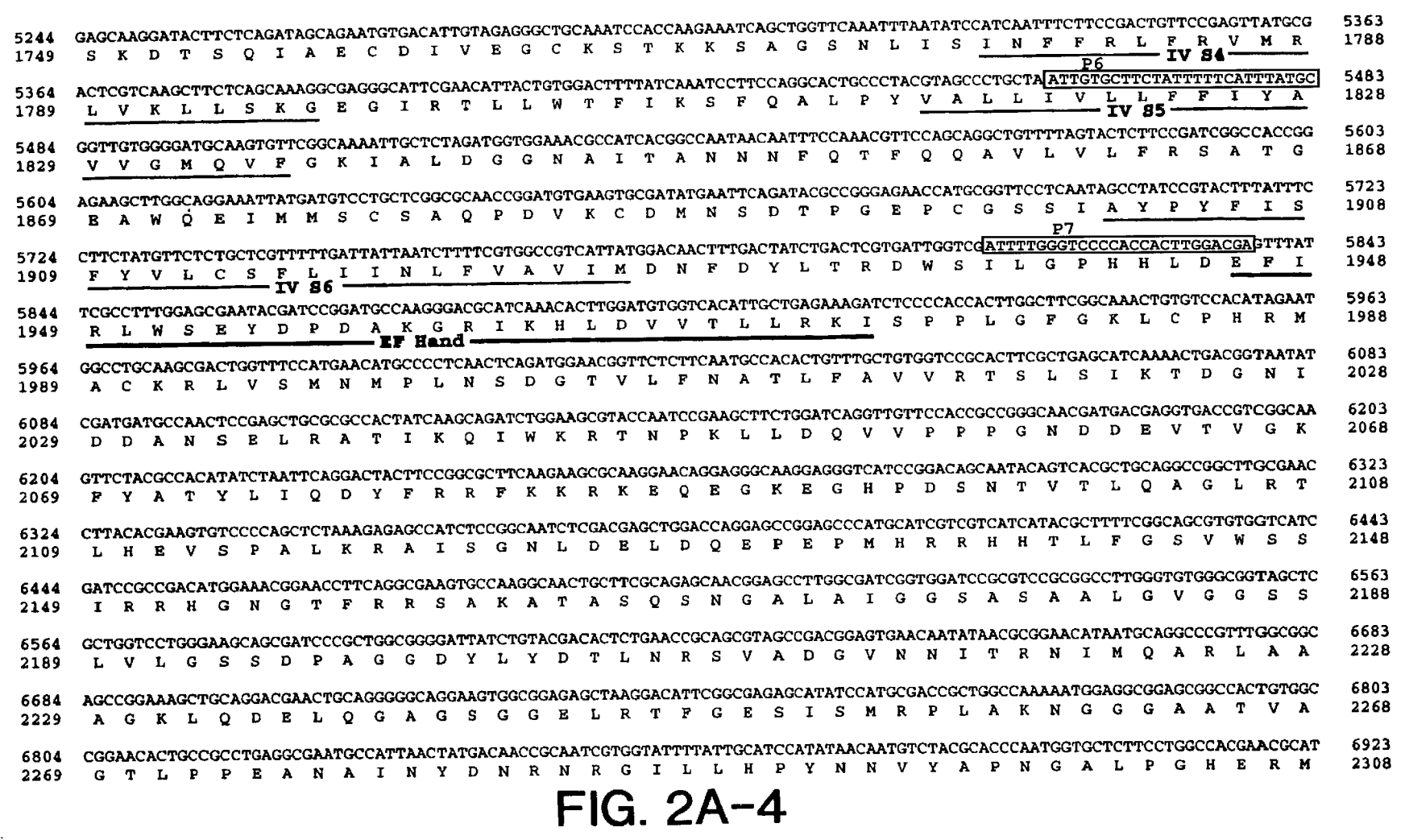
Figure 2B-1:
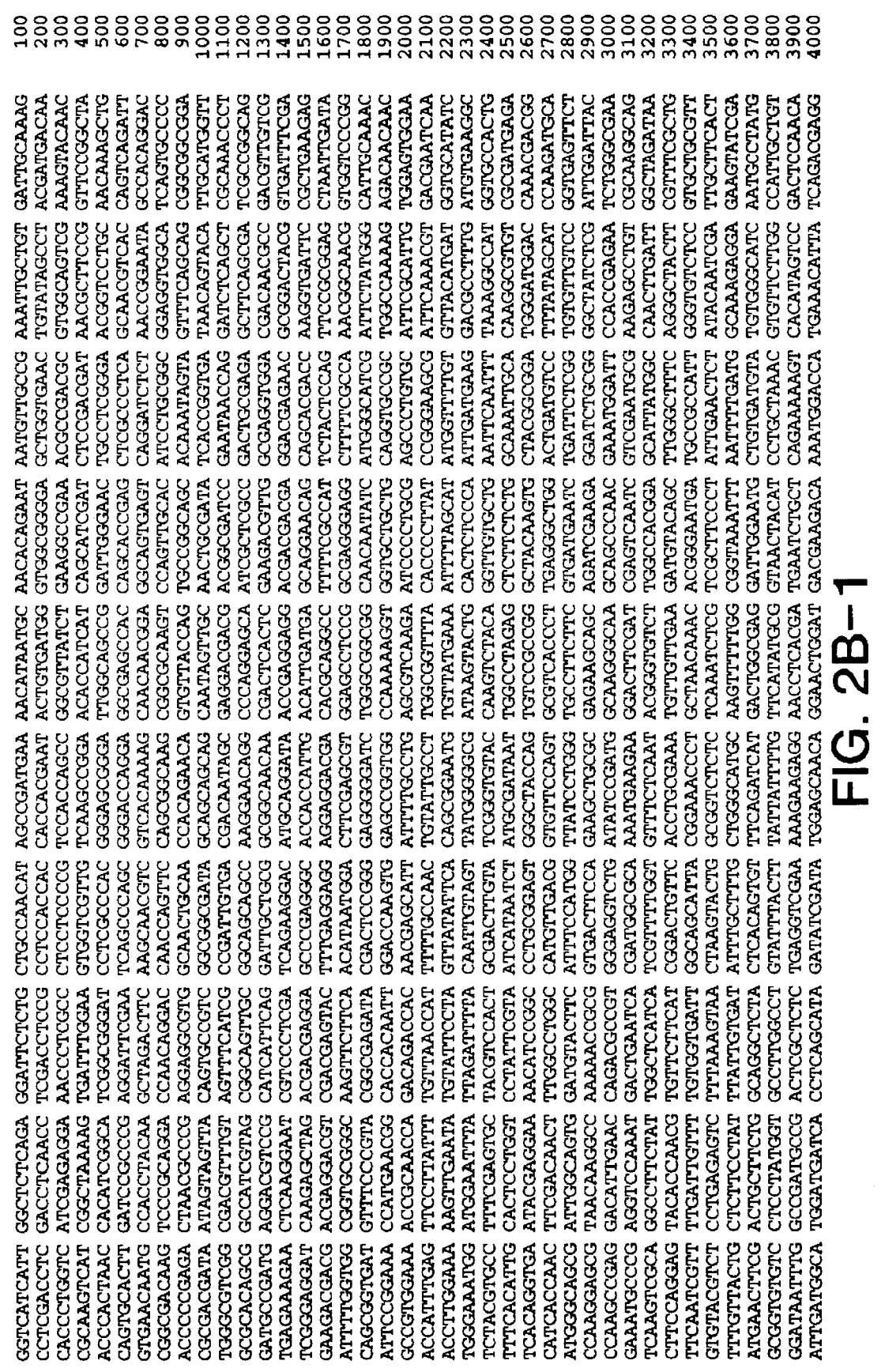

FIG. 2. illustrates the nucleotide sequence (SEQ. ID. NO. 1) and deduced amino acid sequence (SEQ. ID. NO. 2) of the cDNA encoding the Drosophila neuronal $α_1$ subunit of the invention.

FIG. 2a [SEQ ID NOS.: 1 & 2]—2 sequences aligned.

FIG. 2b—SEQ. ID No. 1.

FIG. 2c—SEQ. ID No. 2.

A: Message distribution in adult body parts.

B: developmental profile of calcium channel $α_1$ subunit mRNA expression in embryos showing a peak of expression in the late embryonic stages. Lanes 1–7 represent sequentially older embryos collected over 3 hour intervals and then aged approximately at 25° C. (1=0–3 hr, 2=3–6 hr, 3=6–9 hr, 4=9–12 hr, 5=12–15 hr, 6=15–18 hr, 7=18–24 hr).

Figure 5:
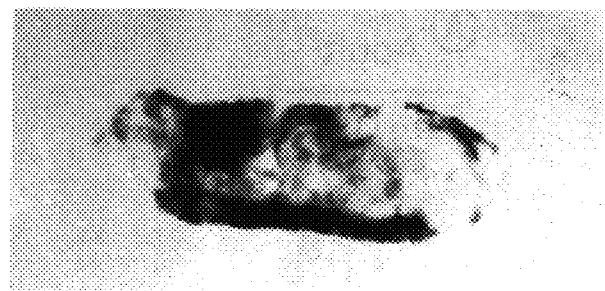

FIG. 5. is a photomicrograph of the localization of $α_1$ subunit mRNA in the embryonic nervous system using in situ hybridization to a whole mount embryo (Dorsal is up and anterior is to the left).

FIG. 6. is a comparison of hydropathy plots for $α_1$ subunits from rat brain type D (Panel A, using the first in-frame methionine (met1) as the initiating amino acid in the Drosophila sequence; Panel B, with the Drosophila subunit). Up is hydrophobic and down (negative numbers) is hydrophilic.

Figure 7:
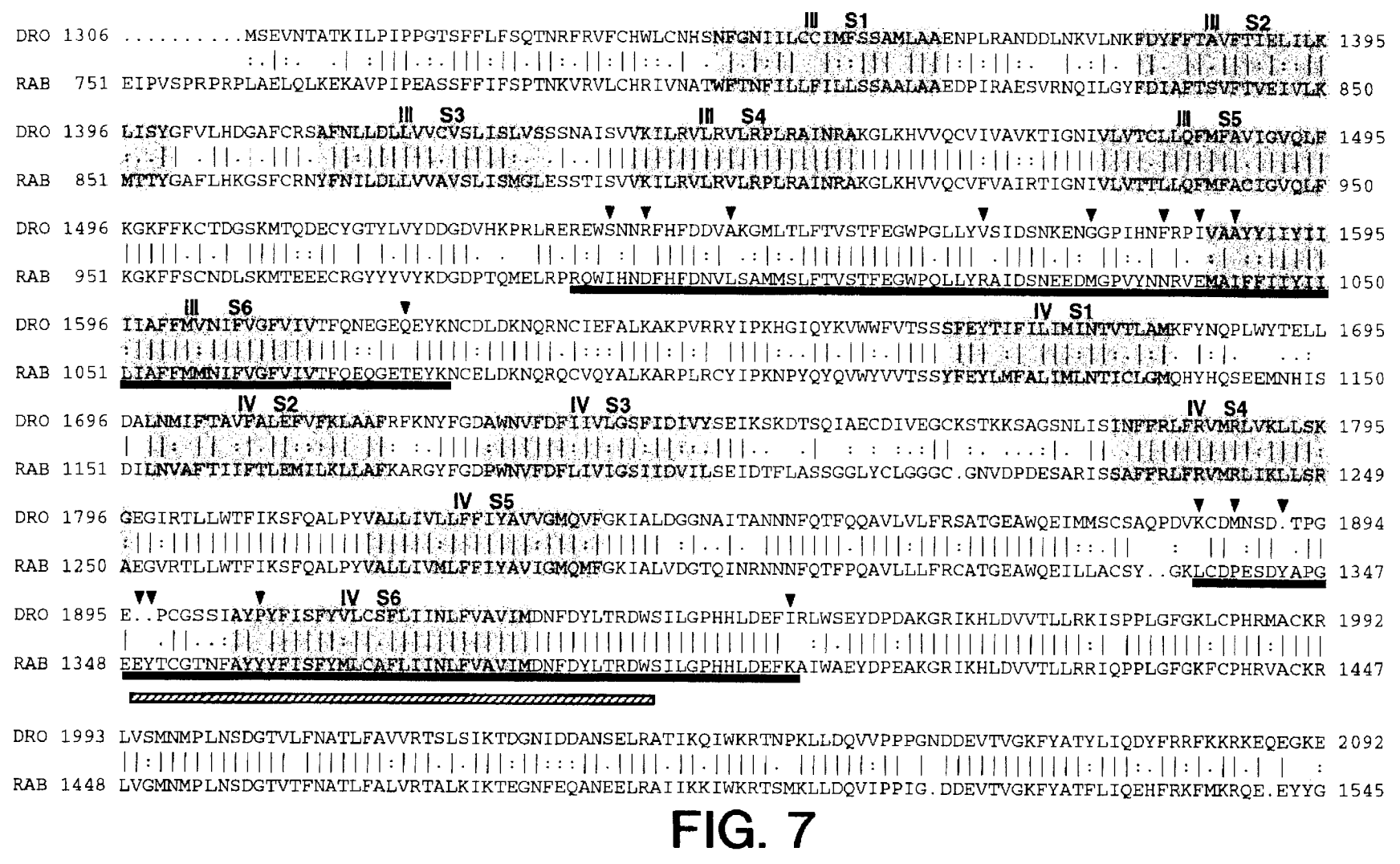

FIG. 7. [SEQ ID NO.s: 3 & 4] illustrates the alignment of the deduced amino acid sequences of $α_1$ subunits from Drosophila (upper) and rabbit skeletal muscle (lower). The transmembrane domains are shaded in gray and their identity is shown above in bold lettering. Nonconservative amino acid substitutions in regions of interest are indicated by filled triangles. The hatched bar indicates the phenylalkylamine-binding fragment. The black bars underline dihydropyridine-binding fragments.

Figure 8A:
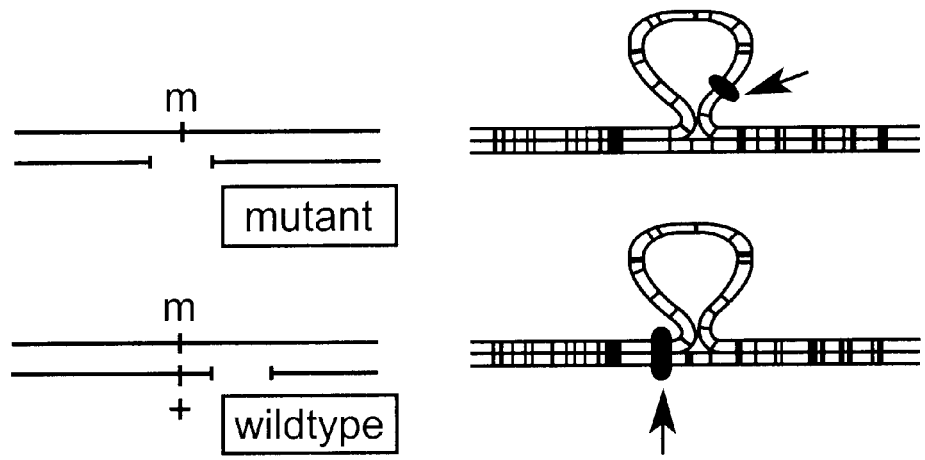
Figure 8B:
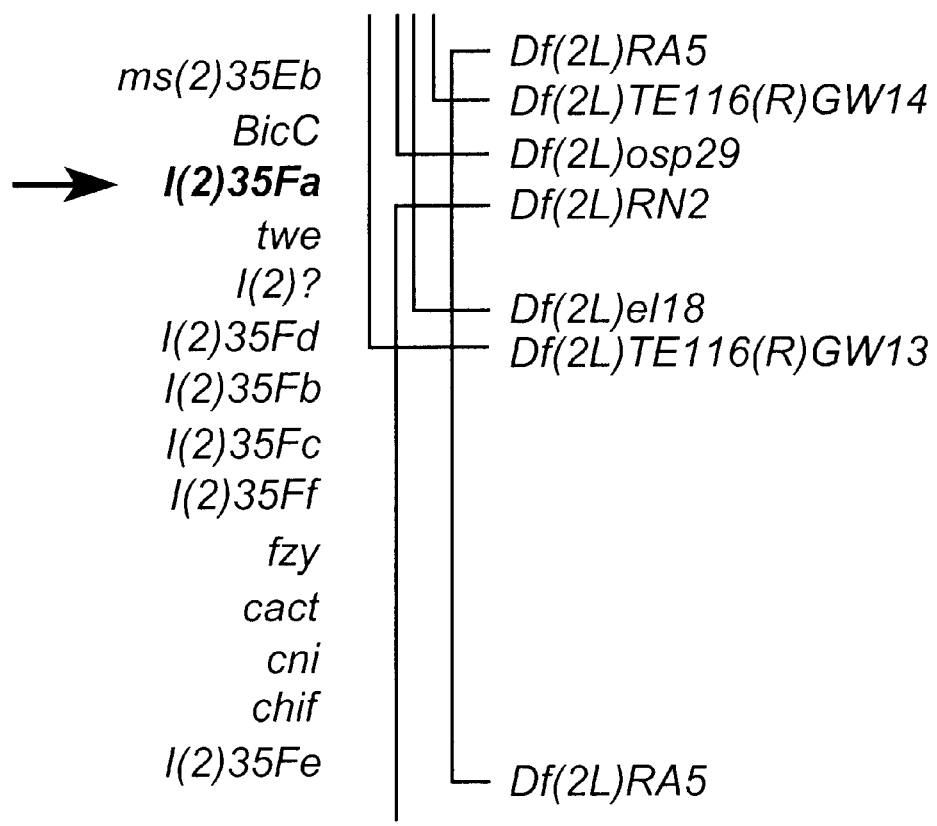

FIG. 8. (A) displays identification of candidate genes for the cloned DmCalD cDNA. (B) Genetic map of the calcium channel region. Genes (left column) have been separated and ordered by numerous deletions (right columns).

FIG. 9 (A) displays genomic cosmid (Ca01) used to rescue 1(2)35Fa. (B) Embryonic Northern blot.

FIG. 10 displays detection of a sequence change in the DmCa1D calcium channel $\alpha_1$ subunit in the X10 allele of 1(2)35Fa. In FIG. 10 (A) Taql site is missing the X10 allele. FIG. 10 (B) shows a premature stop codon in the X10 allele. FIG. 10 (C) represents a schematic diagram of the $\alpha_1$ submit protein showing the location of the stop codon in the X10 mutation (small black box indicated by the arrow).

Figure 11:
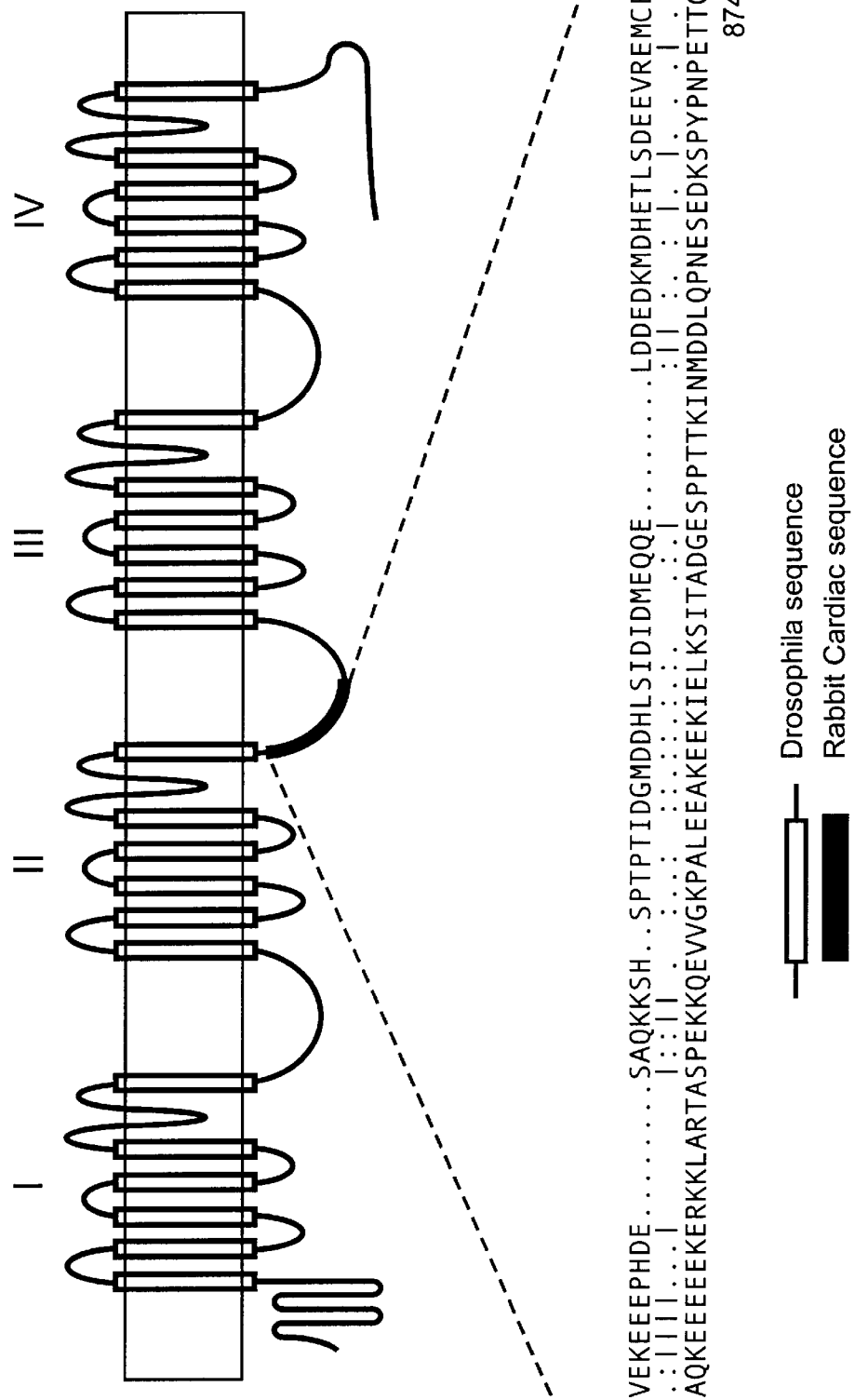

FIG. 11 is a cartoon of the Drosophila chimera L23RDD2 showing the distribution of fly and rabbit sequences.

Figure 12:
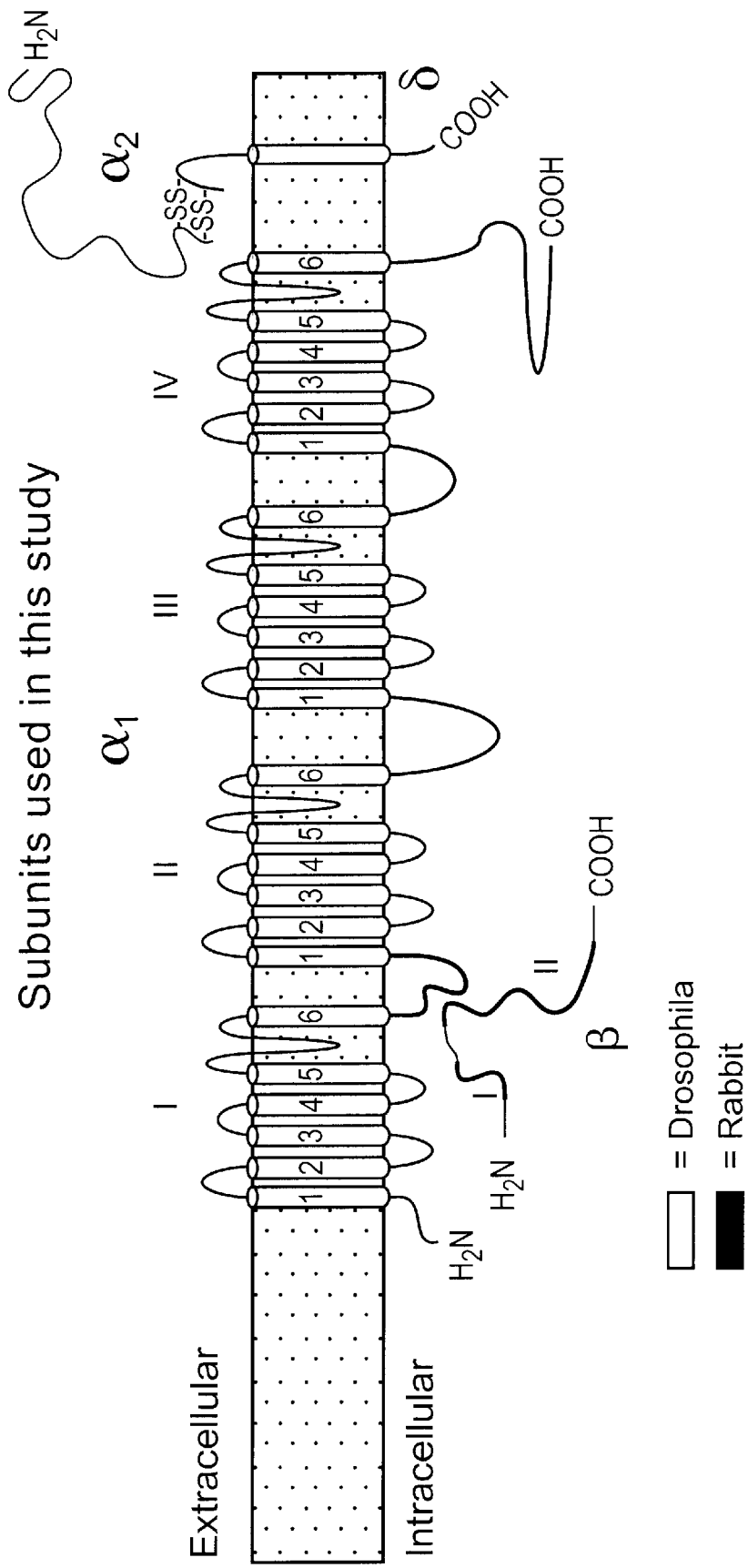

FIG. 12 displays the subunits used for studies of the insect channel.

Figure 13:
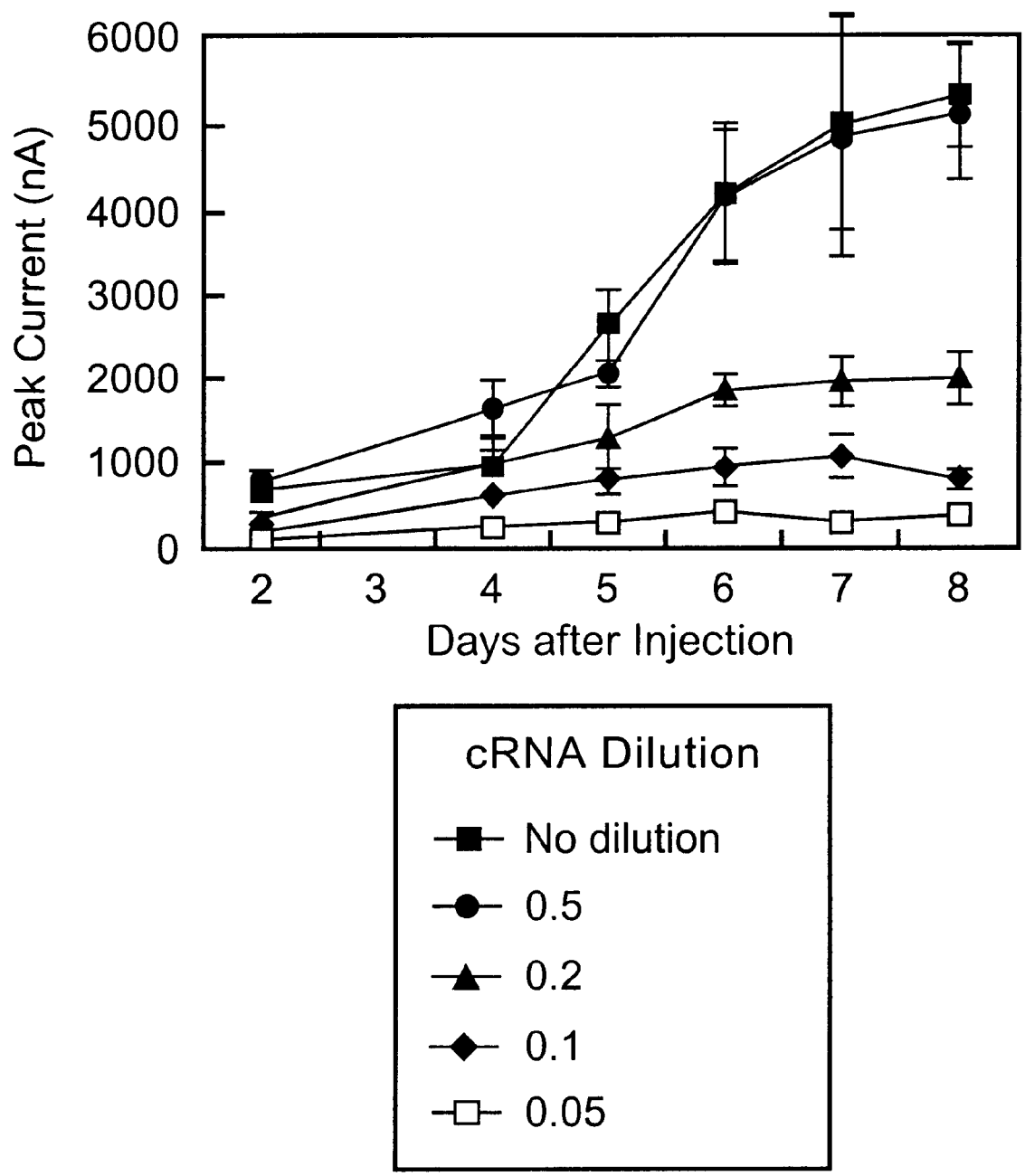

FIG. 13 shows the time course of Drosophila calcium channel expression in Xenopus oocytes. cRNA Dilution: ■=no dilution; ●=0.5; ▲=0.2; ♦=0.1; □=0.05.

Figure 14:
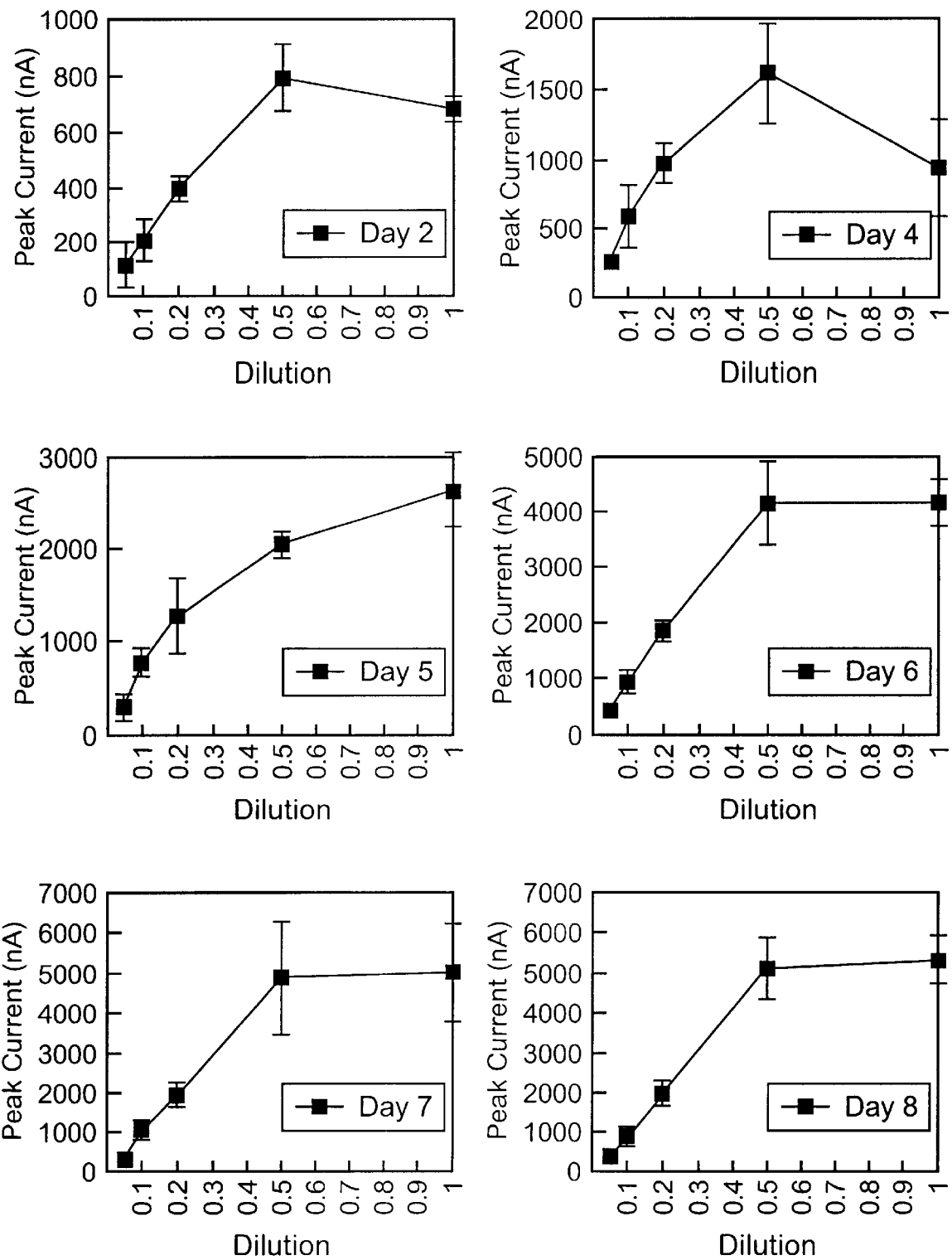

FIG. 14 displays peak current versus cRNA dilution. Day=time between injection and recording.

Figure 15:
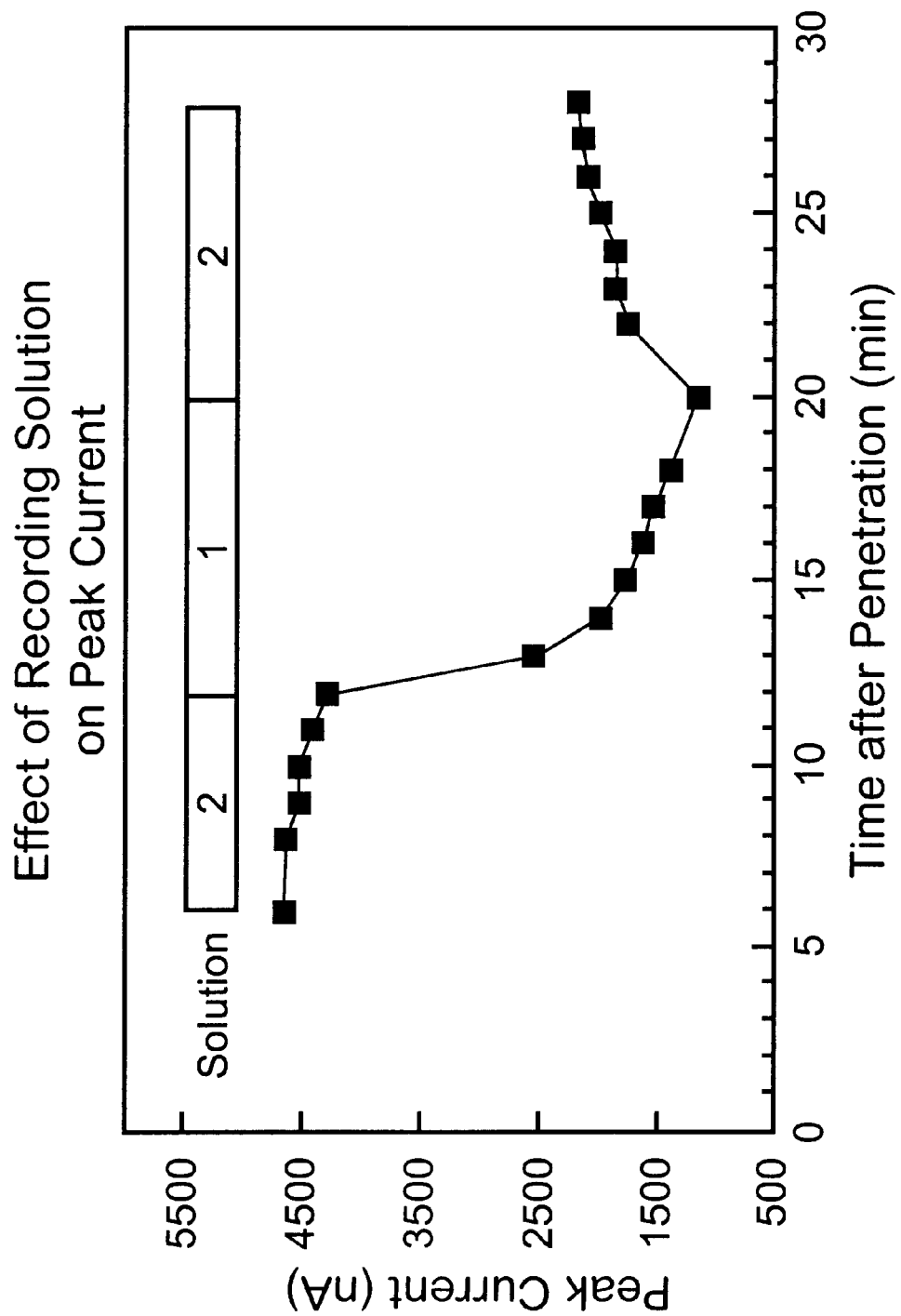

FIG. 15 shows the effect of recording solution on peak current.

Figure 16:
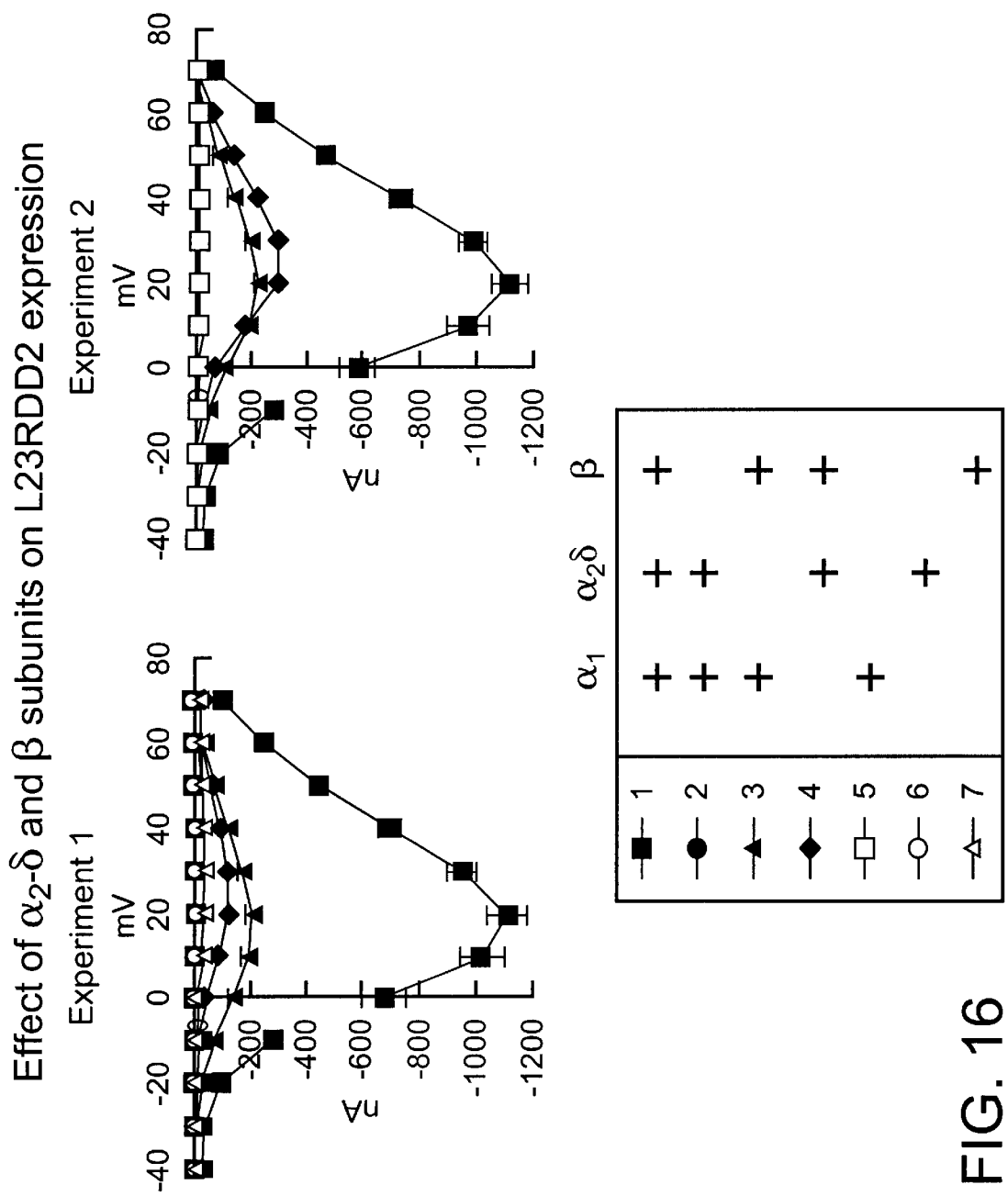
Figure 17:
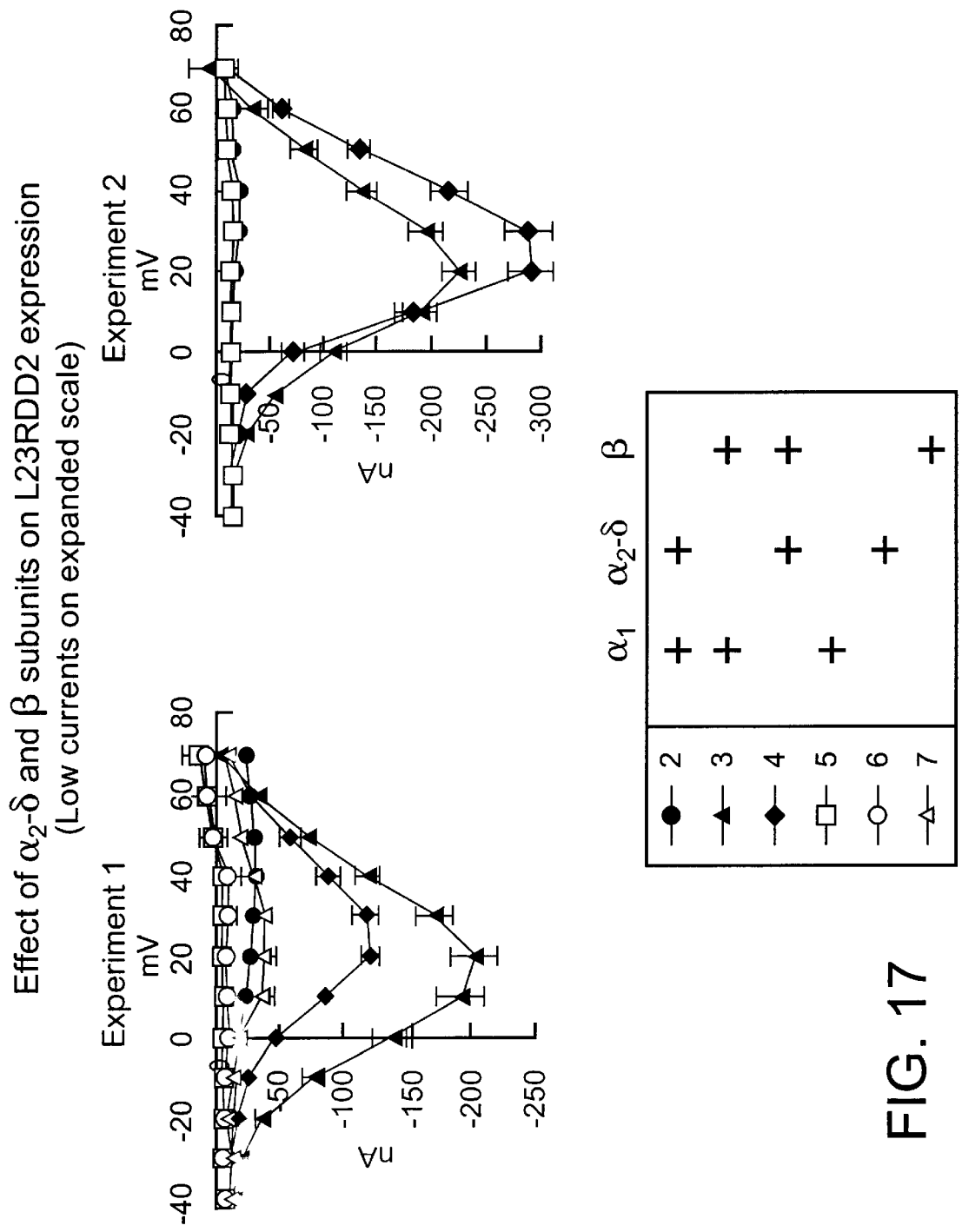

FIG. 16 illustrates the effects of $\alpha_2$–δ and β subunits on L23RDD2 expression FIG. 17 illustrates the effects of $\alpha$–δ and β subunits on L23RDD2 expression (low currents on expanded scale).

Figure 18:
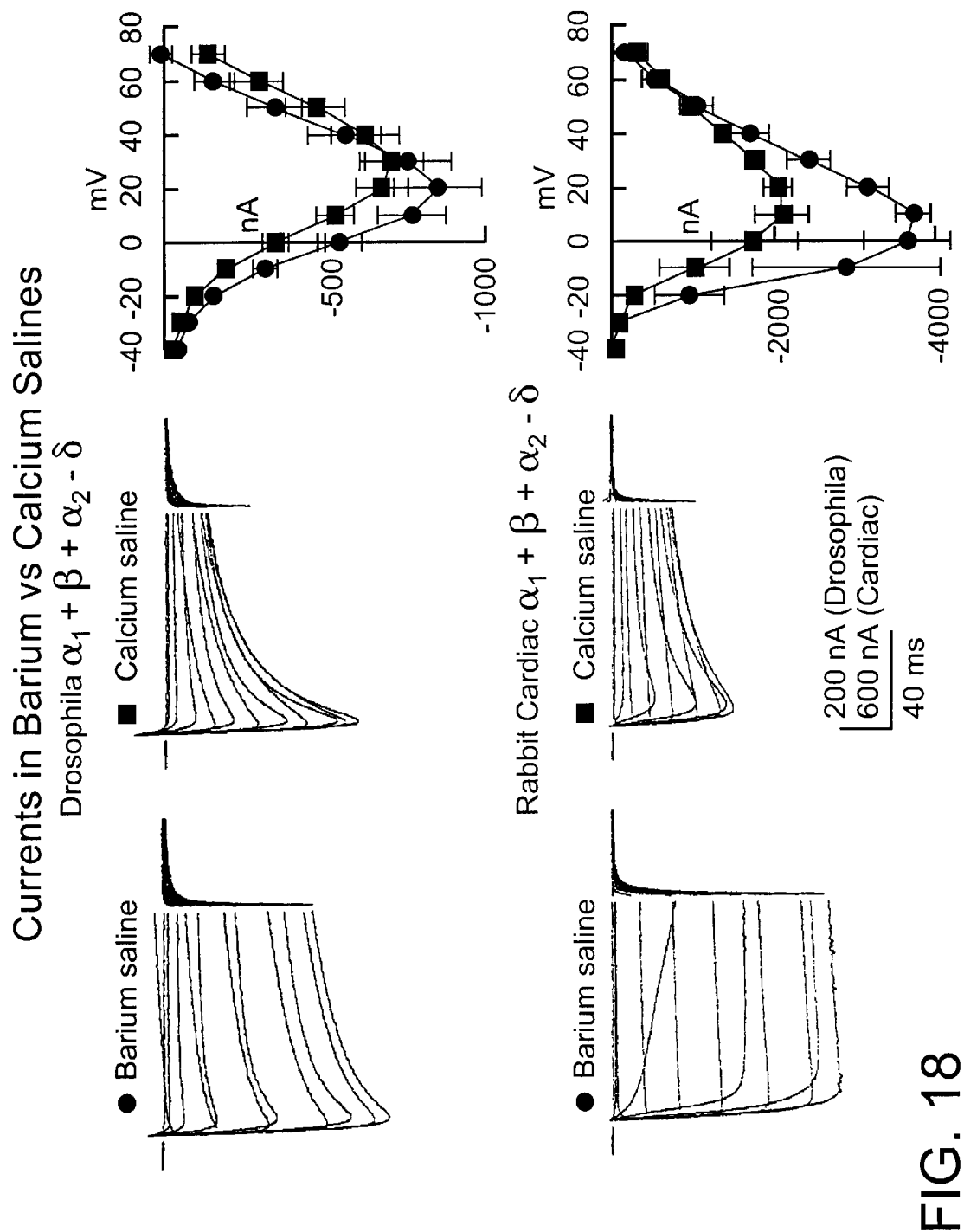

FIG. 18 shows the currents in barium versus calcium salines for the Drosophila $\alpha_1$+β+$\alpha_2$–δ channel and the rabbit cardiac $\alpha_1$+β+$\alpha_2$–δ channel. ●=barium saline; ■=calcium saline.

Figure 19:
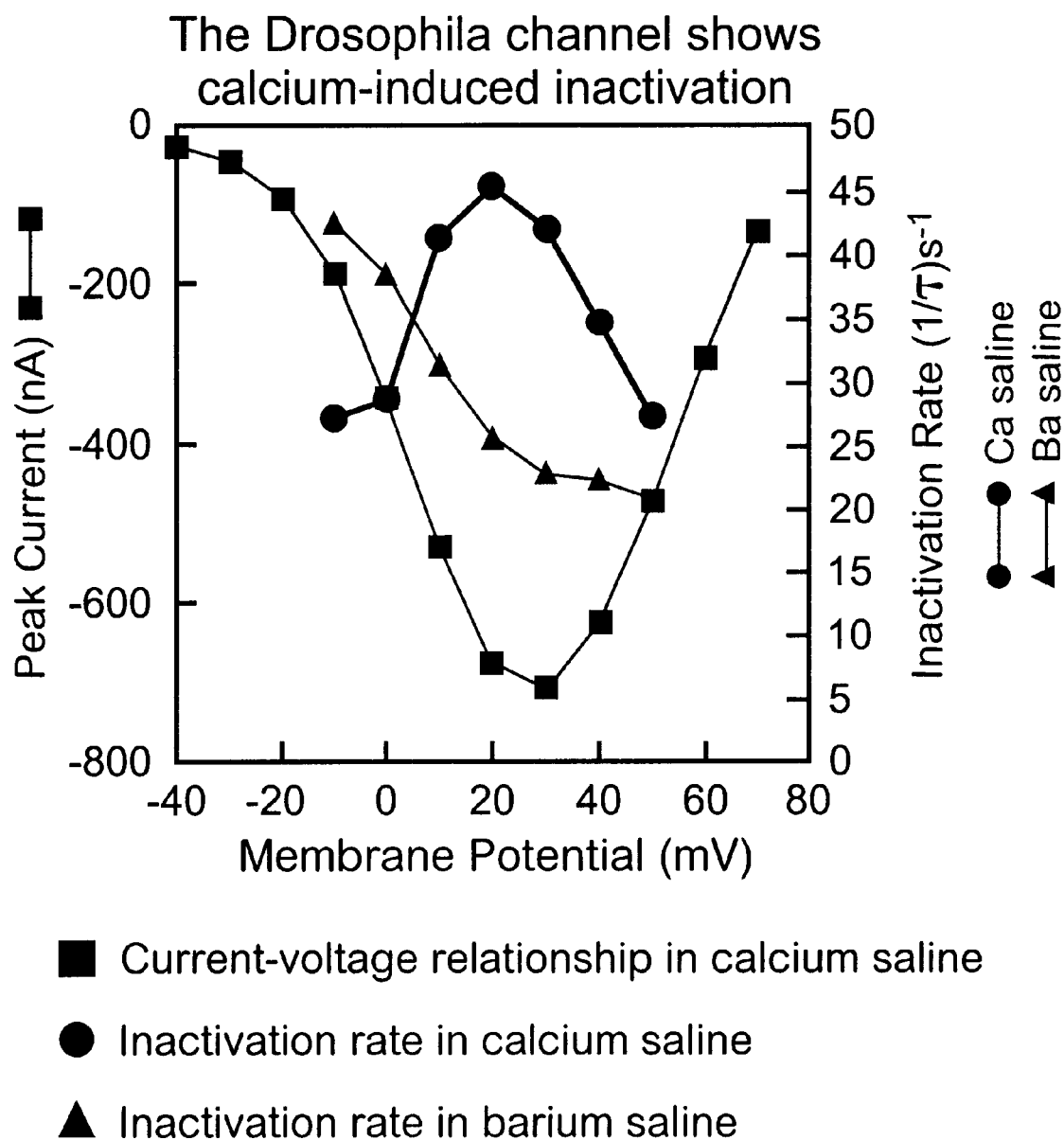

FIG. 19 demonstrates the calcium-induced inactivation of the Drosophila channel. ■=current-voltage relationship in calcium saline; ●=inactivation rate in calcium saline; ▲=inactivation rate in barium saline.

Figure 20:
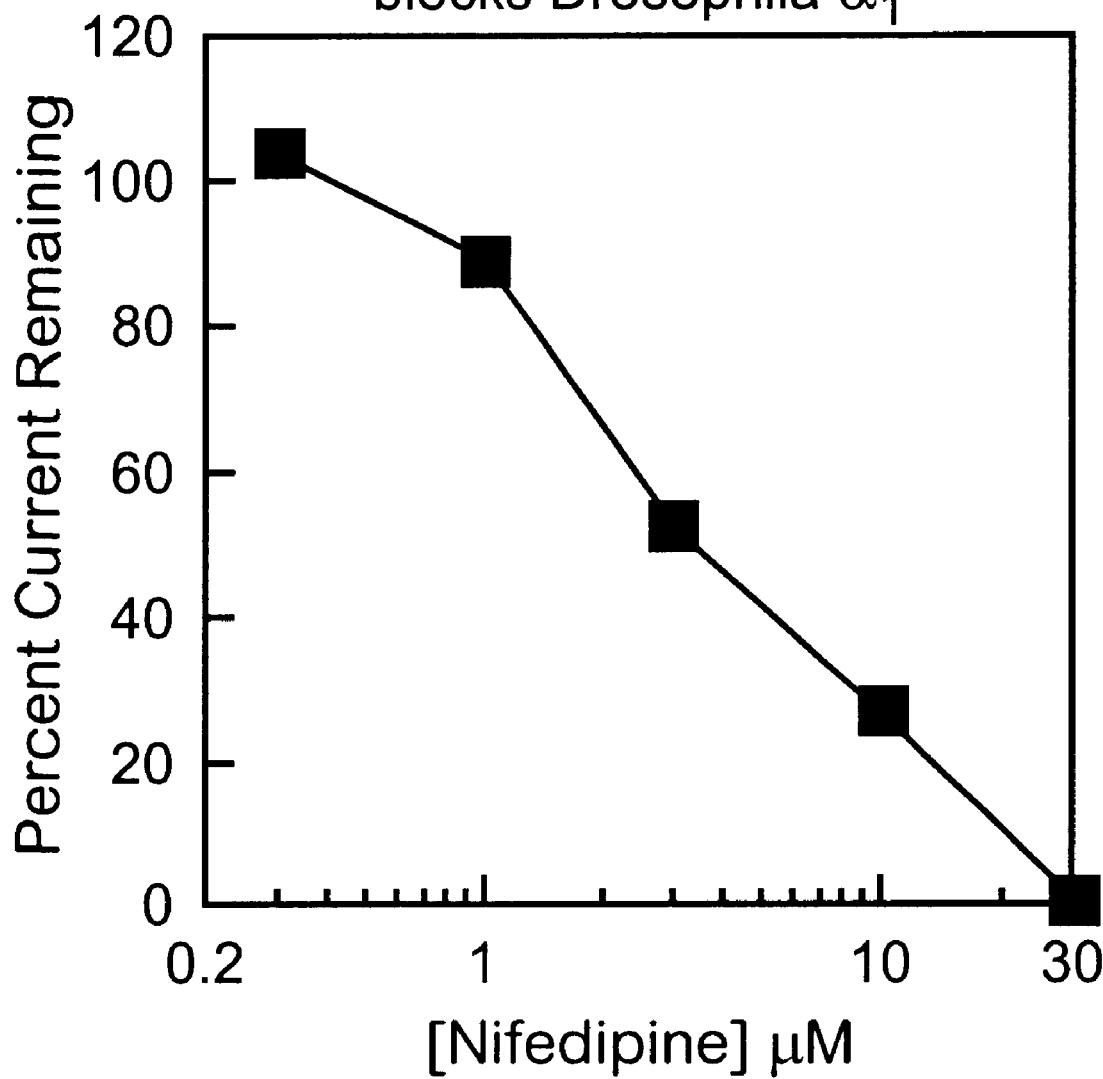

FIG. 20 illustrates the ability of the dihyrdropyridine antagonist Nifedipine to block the currents from Drosophila $\alpha_1$ subunit.

Figure 21:
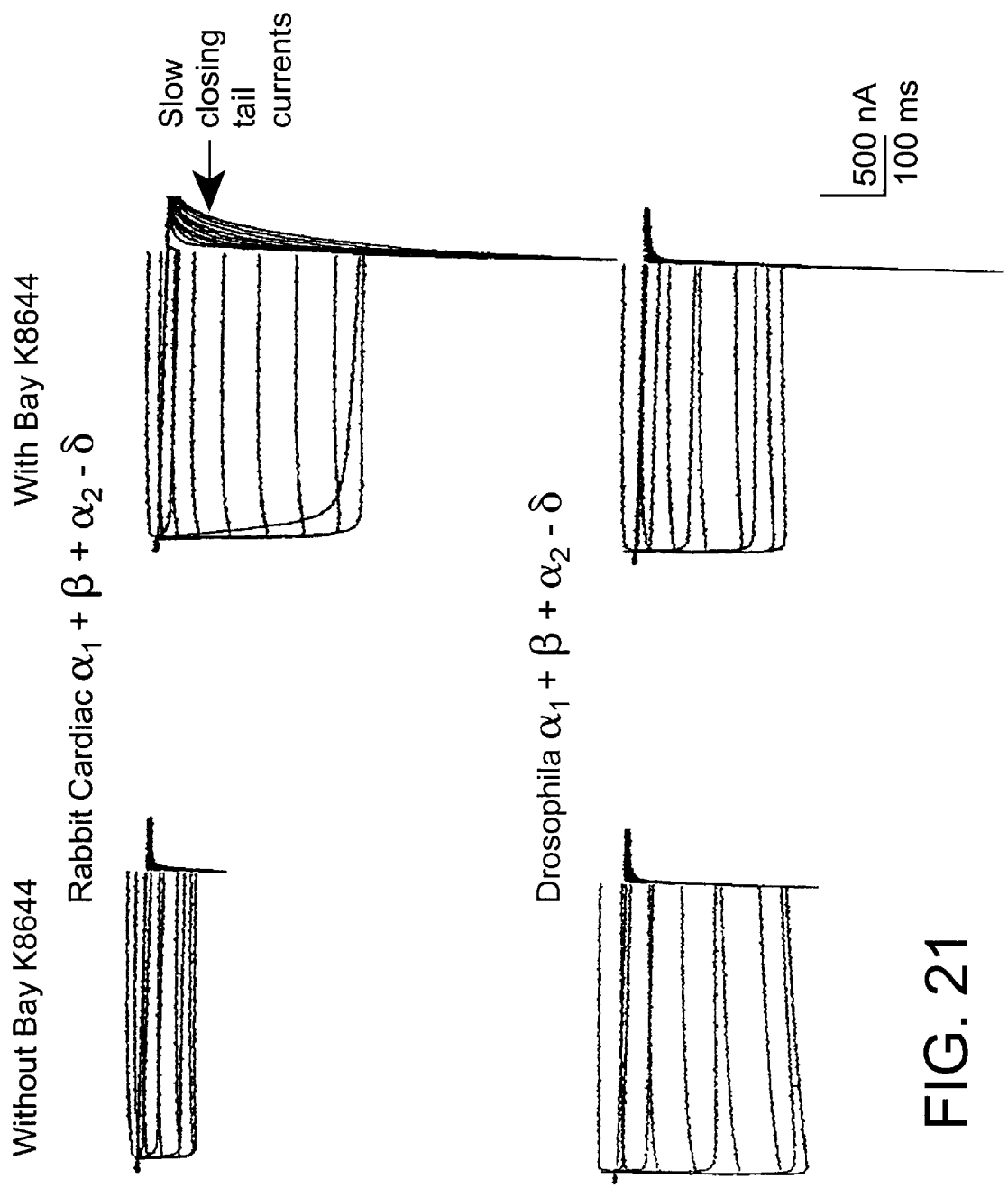

FIG. 21 shows the same oocyte recorded first in the absence of the dihydropyridine agonist BayK8644 and then perfused with 2 μM BayK8644.

FIG. 22 shows the chemical structure of the dihydropyridine agonist BayK8644 and the dihydropyridine antagonist Nifedipine.

FIG. 23 compares the sequences in the regions of interest in vertebrate channels with those in Drosophila channels. The sequences in the dihydropyridine (DHP)-insensitive channels are given in the group below the L-type DHP-sensitive group. Those residues which have been mutagenized are boxed. In general, those which do not affect dihydropyridine sensitivity when changed are boxed in blue while those which do affect sensitivity are boxed in red. Residues which differ between sensitive vertebrate channels and the DmcalD subunit are circled. These circled residues are candidates for changes which may be responsible for the difference in dihydropyridine agonist sensitivity between Drosophila and vertebrate channels. Although most of the vertebrate experiments examined sensitivity to dihydropyridine antagonists, the * residues indicate changes which affect both agonist and antagonist sensitivity.

Figure 24:
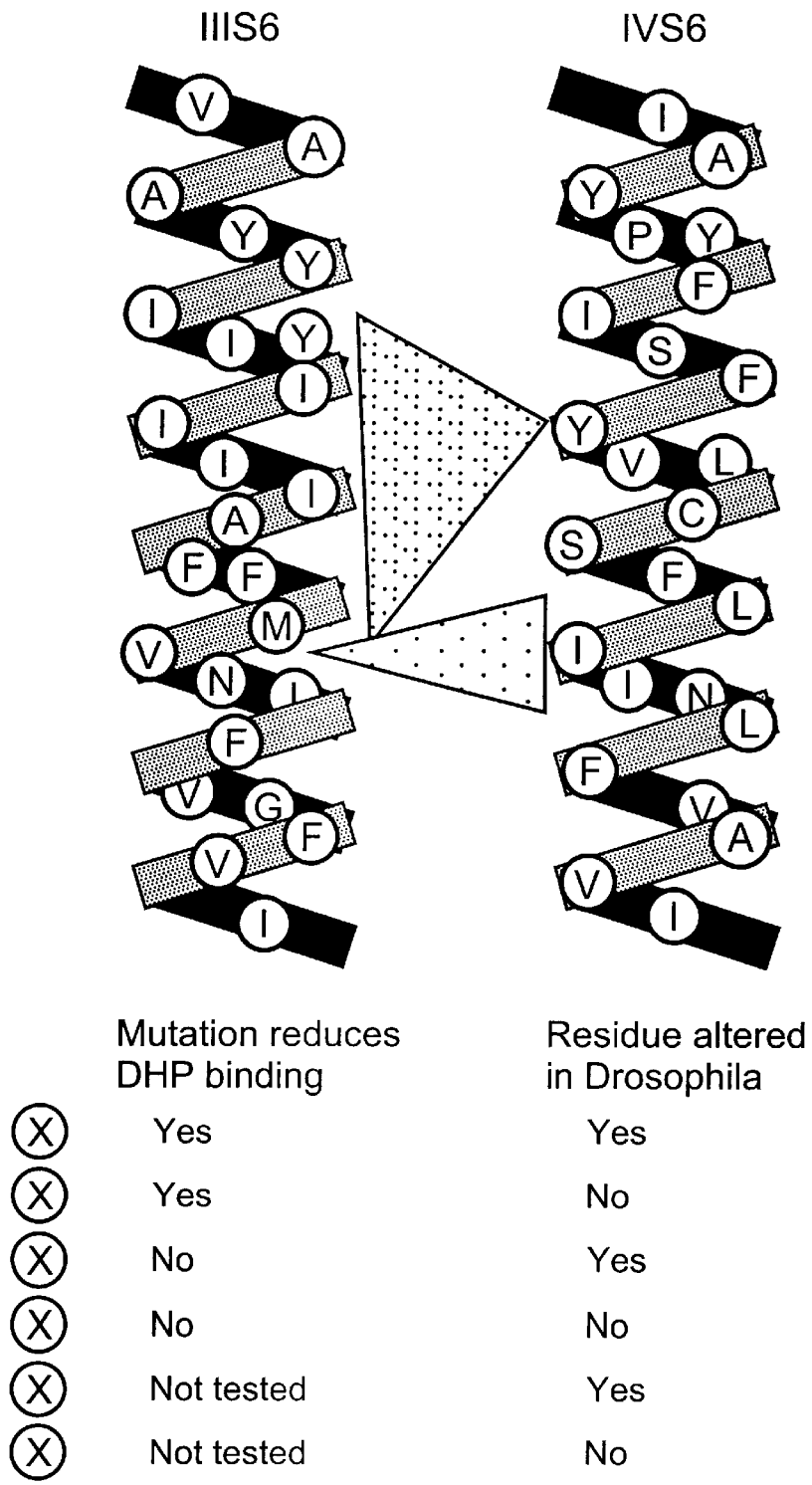

FIG. 24 shows the Drosophila DmcalD sequences in domains IIIS6 and IVS6 with the model for dihydropyridine interactions deduced from the mutagenesis studies superimposed. The yellow triangles are a schematic representation of parts of the dihydropyridine molecule thought to interact with the channel amino acid side chains. Residues within red circles affect dihydropyridine sensitivity when mutated. Those residues in which the letter for the amino acid are in green represent those amino acids in Drosophila which differ from the vertebrate L-type channels and therefore may be involved in the lack of sensitivity to dihydropyridine agonist in the insect channel.

DETAILED DESCRIPTION OF THE PREFERRED EMBODIMENTS OF THE INVENTION

The present invention provides for the characterization and isolation of a neuronal calcium channel $\alpha_1$ subunit gene cloned from *Drosophila melanogaster*, and designated herein as "Dmca1D". The present invention provides the complete sequence of a calcium channel $\alpha_1$ subunit cDNA cloned from a Drosophila head cDNA library. This appears to be the first neuronal invertebrate calcium channel subunit cloned using a PCR approach which relied on sequence similarity to previously cloned calcium channels from vertebrate species. The approach used in the present invention allowed for the rapid cloning of related genes from evolutionarily distant organisms and should be applicable for the cloning of $\alpha_1$ subunits from other invertebrate preparations of physiological or economic importance.

The present invention provides for the isolation of genomic DNA fragments) from *Drosophila melanogaster* which encode a conserved amino acid sequence unique to the voltage-dependent calcium channel multigene family. Polymerase chain reaction ("PCR")-based homology was utilized to isolate genomic DNA fragments) which were used to probe a cDNA library. Using these techniques, the first neuronal invertebrate calcium channel subunit genes were cloned. More particularly, these techniques yielded four $\alpha_1$ cDNA clones, designated N1, W8A, SH22C, and SH22D—the open reading frame of the combined cDNA clones (primarily N1, W8A, and SH22C) encompasses the Dmca1D gene sequence of the present invention.

It is understood that the cDNAs encoding the clones designated N1, W8A, SH22C, and SH22D (whose combination encompasses the open reading frame of the Dmca1D gene) are for purposes of illustration only, and the existence of a diverse family of genes in *Drosophila melanogaster* that are structurally related to the voltage-dependent calcium channel gene family of invertebrates is supported by the present invention.

The genomic sequence of the invention, designated DmcalD, exhibits the conserved features commonly found in members of the family of voltage-dependent calcium channel genes. More specifically, the DmcalD genomic sequence encodes a deduced protein estimated to contain 2516 amino acids with a predicted molecular weight of 276,493 kDa. The deduced protein shares many features with vertebrate homologs including: (1) 4 repeat structures each containing 6 transmembrane domains; (2) a conserved ion selectivity filter region between transmembrane domains 5 and 6; and (3) an EF hand in the carboxy tail. The Drosophila subunit is unusual in that the initial amino and terminal carboxy tails are much longer than those of the vertebrate homologs. The region corresponding to the last transmembrane domain (IVS6) and the adjacent cytoplasmic domain have been postulated to form a phenylalkylamine-binding site in vertebrate calcium channels. This region is completely conserved in the Drosophila sequence while domains thought to be involved in dihydropyridine binding show numerous changes. Since the Drosophila subunit of the invention exhibits 78.3% sequence similarity to the type D calcium channel $\alpha_1$ subunit from rat brain, it has been designated *Drosophila melanogaster* calcium channel $\alpha_1$ type D subunit ("DmcalD"). This appears to be the first report of a neuronal calcium channel subunit sequence from an invertebrate species. In situ hybridization using digoxigenin-labeled probes shows that DmcalD is highly expressed in the embryonic nervous system. Northern analysis shows that DmcalD cDNA hybridizes to three size classes of mRNA (9.5, 10.2 and 12.5 kb) in heads, but only two classes (9.5 and 12.5 kb) in bodies and legs. PCR analysis of CDNA versus genomic DNA suggests that the DmcalD message undergoes alternative splicing with more heterogeneity appearing in head and embryonic extracts than in bodies and legs.

In accordance with one embodiment of the invention, there is provided an isolated gene and/or gene fragment or portion thereof comprising a DNA molecule encoding a calcium channel $\alpha_1$ subunit from *Drosophila melanogaster*. Preferably, the DNA molecule of the invention encodes for an amino acid sequence, or mutant thereof, corresponding to DmcalD, as shown in FIG. 2 (SEQ. ID. No. 2). The DNA molecule of the invention preferably comprises a nucleotide sequence, or a mutant DNA sequence thereof, corresponding to DmcalD, as shown in FIG. 2 (SEQ. ID. NO. 1). It is understood that any modifications, e.g., insertions, deletions, mutations, recombinants, etc., of the DNA nucleotide and/or corresponding amino acid sequences are within the scope of the present invention provided that the modified sequences encode for a gene, its homologs or a fragment thereof producing a calcium channel $\alpha_1$ subunit from *Drosophila melanogaster*. In addition, this subunit should exhibit pharmacological properties of the native calcium channel $\alpha_1$ subunit in neuronal invertebrate tissue.

Recombinant DNA techniques are used to insert the DNA sequences of the invention (e.g. gene encoding the calcium channel $\alpha_1$ subunit from *Drosophila melanogaster*) from *Drosophila melanogaster* into an appropriate expression vector, i.e., a vector which contains the necessary elements for the transcription and translation of the inserted coding sequences. A large number of vector systems known in the art can be used, such as, plasmids, bacteriophage virus or other modified viruses. Suitable vectors include, but are not limited to the following viral vectors such as lambda vector system gt11, gtWES.tB, Charon 4, and plasmid vectors such as pBR322, pBR325, pACYC177, pACYC184, pAR series, pKK223–3, pUC8, pUC9, pUC18, pUC19, pLG339, pR290, pKC37, pKC101 and other similar systems. The DNA sequences are cloned into the vector using standard cloning procedures in the art, as described by Sambrook et al., (1989), in: *Molecular Cloning: A Laboratory Manual*, 2nd ed., Cold Springs Harbor Laboratory Press, Cold Springs Harbor, N.Y., which disclosure is hereby incorporated by reference.

The recombinant DNA molecule (e.g., vector+sequence of invention) can then be introduced into appropriate host cells, including but not limited to bacteria, virus, yeast, vertebrate or invertebrate cells or the like. The vector system must be compatible with the host cell used. The recombinant vectors can be introduced into the host cells via transformation, transfection or infection using standard techniques in the art. A variety of host cell systems can be used to express the calcium channel $\alpha_1$ subunit gene of the invention. For example, host cell systems include, but are not limited to the following: bacteria transformed with bacteriophage DNA, plasmid DNA or cosmid DNA such as *E. coli* JM103, *E. coli* C600, *E. coli* C04, *E. coil* IDH20 and *E. coli* TB1; microorganisms such as yeast containing yeast vectors; mammalian cell systems infected with virus (e.g., vaccinia virus, adenovirus, etc.); and invertebrate cell systems infected with virus (e.g., baculovirus).

In order to obtain efficient expression of the calcium channel $\alpha_1$ subunit gene, a promoter must be present in the expression vector. RNA polymerase normally binds to the promoter and initiates transcription of a gene or a group of linked genes and regulatory elements (operon). Promoters vary in their strength, i.e., ability to promote transcription. For the purpose of expressing the gene of the invention, it is desirable to use strong promoters in order to obtain a high level of transcription and, hence, expression of the gene. Depending upon the host cell system utilized, any one of a number of suitable promoters can be used, such as, the lac promoter, trp promoter, recA promoter, ribosomal RNA promoter, the $P_R$ and $P_L$ promoters of coliphage lambda, the copra (Flavell, A. J., Levis, R., Simon, M. A., and Rubin, G. M. (1981) Nucleic Acid Research 9, 6279–6291), heat-shock 70 (Ingolia, T. D., Craig, E. A., and McCarthy, B. J. (1980) Cell 21, 669–679) or metallothionein promoters (Maroni, G., Otto, E. and Lastowski-Perry, D. (1986) Genetics 112, 493–504) from Drosophila, and others including but not limited to lacUV5, ompF, bla, Ipp and the like, nos promoter, the small subunit ribulose bisphosphate carboxylase genes, the small subunit chlorophyll A/B binding polypeptide, the 35S promoter of cauliflower mosaic virus, and promoters isolated from plant genes, including the Pto promoter itself (Vallejos et al., (1986), *Genetics*, vol. 112, pp. 93–105, which disclosure is hereby incorporated by.reference) to direct high levels of transcription of adjacent DNA segments.

Host cell strains and expression vectors can be chosen which inhibit the action of the promoter unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, pro, etc., are under different controls. The trp operon is induced when tryptophan is absent in the growth media; and the PL promoter of lambda can be induced by an increase in temperature in host cells containing a temperature sensitive lambda repressor, e.g., c1857. In this way, greater than 95% of the promoter-directed transcription may be in inhibited in uninduced cells. Thus, expression of the gene of the invention can be controlled.

One such promoter/operator system is the so-called "tac" or trp-lac promoter/operator system (Russell and Bennett, (1992), Gene, vol. 20, pp.231–243, which disclosure is hereby incorporated by reference). This hybrid promoter is constructed by combining the –35 bp (–35 region) of the trp promoter and the –10 bp (–10 region or Pribnow box) of the lac promoter (the sequences of DNA which are the RNA polymerase binding site). In addition to maintaining the strong promoter characteristics of the tryptophan promoter, tac is also controlled by the lac repressor.

When cloning in a eucaryotic host cell, enhancer sequences (e.g. , the 72 bp tandem repeat of SV40 DNA or the retroviral long terminal reoeats of LTRs, etc.) may be inserted to increase transcriptional efficiency. Enhancer sequences are a set of eucaryotic DNA elements that appear to increase transcriptional efficiency in a manner relatively independent of their position and orientation with respect to a nearby gene. Unlike the classic promoter elements (e.g., the polymerase binding site and the Goldberg-Hogness "TATA" box) which must be located immediately 5' to the gene, enhancer sequences have the remarkable ability to function upstream from, within, or downstream from eucaryotic genes. Therefore, the position of the enhancer sequence with respect to the inserted gene is less critical.

Specific initiation signals are also required for efficient gene transcription and translation in procaryotic cells. These transcription and translation initiation signals may vary in strength as measured by the quantity of gene specific messenger RNA and protein synthesized, respectively. The DNA expression vector, which contains a promoter, may also contain any combination of various "strong" transcription and/or translation initiation signals. For instance, efficient translation in E. coli requires a Shine-Dalgarno ("SD") sequence about 7–9 bases 5' to the initiation codon (ATG) to provide a ribosome binding site. Thus, any SD-ATG combination that can be utilized by host cell ribosomes can be employed. Such combinations include but are not limited to the SD-ATG combination from the CR0 gene or the N gene of coliphage lambda, or from the E. coli tryptophan E, D, C, 3 or A genes. Additionally, any SD-ATG combination produced by recombinant DNA or other techniques involving incorporation of synthetic nucleotides can be used.

Any of the conventional cloning methods for insertion of DNA fragments into a vector can be used to ligate the promoter and other control elements into specific sites within the vector. Accordingly, gene sequences containing those regions coding for the calcium channel $\alpha_1$ subunit of the invention can be ligated into an expression vector at a specific site in relation to the vector promoter and control elements so that when the recombinant DNA molecule is introduced into a host cell the foreign genetic sequence can be expressed (i.e., transcribed and translated) by the host cell.

As previously mentioned, the recombinant DNA molecule can be introduced into appropriate host cells (including but not limited to bacteria, virus, yeast, vertebrate and invertebrate cells or the like) by transformation, infection or transfection (depending upon the vector/host cell systerm). Transformants are selected based upon the expression of one or more appropriate gene markers normally present in the vector, such as ampicillin resistance or tetracycline resistance in pBR322, or thymidine kinase activity in eucaryotic host systems. Expression of such marker genes should indicate that the recombinant DNA molecule is intact and is replicating. Expression vectors may be derived from cloning vectors, which usually contain a marker function. Such cloning vectors may include, but are not limited to the following: SV40 and adenovirus, vaccinia virus vectors, neuronal invertebrate viruses such as baculoviruses, yeast vectors, bacteriophage vectors such as lambda gt-WES-lambda BC, lambda gt-1-lambda B, M13mp7, M13mpg, M13mp9, or plasmid DNA vectors such as pBR322, pAC105, pVA51, pACYC177, pKH47, pACYC184, pUB110, pMB9, pBR325, Col E1, pSC101, pBR313, pML21, RSF2124, pCR1, RP4, pBR328 and the like.

The expression vectors containing the foreign gene inserts (i.e., DNA encoding the calcium channel $\alpha_1$ subunit of the invention) can be identified by three approaches: (1) DNA-DNA hybridization using probes comprising sequences that are homologous to the gene(s); (2) presence or absence of "marker" gene function and (3) expression of inserted sequences based on physical, immunological or functional properties. Once a recombinant which expresses the gene is identified, the gene product should be analyzed. Functional analysis is especially important because the ultimate goal is to use the gene(s) or recombinant expression systems that express the gene(s) in assays for screening chemical agents. Once the calcium channel $\alpha_1$ subunit is identified, it is cultured under conditions which facilitate growth of the cells and expression of the gene as will be apparent to one skilled in the art, then isolated and purified by standard methods including chromatography (e.g., ion exchange, affinity, and sizing column chromatography), centrifugation, differential solubility, or by any other standard techniques. In addition, since the amino acid sequence is known from the DNA sequence of the invention, the calcium channel $\alpha_1$ subunit can be synthesized by chemical methods according to the procedure of Hunkapiller et al., (1984), Nature, vol. 310, pp. 105–11 1, which disclosure is hereby incorporated by reference.

The functional calcium channel receptor produced by expression of the calcium channel $\alpha_1$ subunit gene above of the invention, can be used to screen for pesticides that are in the control of invertebrates. It is known that the invertebrate calcium channel receptor forms a particularly attractive site for pesticides due to pronounced differences in its pharmacology with that of vertebrates, as described by Glossman (Brit. J. Pharmacol., 202:446–456 (1991)), which disclosure is hereby incorporated by reference. Due to those differences in neuronal invertebrate and vertebrate calcium channel receptor pharmacology, cells transformed to include the neuronal invertebrate calcium channel receptor formed in accordance with the present invention can be exposed to various potential insecticides and pesticides and evaluated for their susceptibility to the agents to develop and identify invertebrate control agents that will not cause adverse effects to vertebrate species. Exemplary methods of screening are described in Eldefrawi et al.((1987), FASEB J., 1:262–271) and Rauh et al.((1990), Trends Pharmacol. Sci., 11:325–329), which disclosures are hereby incorporated by reference.

The following examples are presented in order to more fully illustrate the preferred embodiments of the invention. They should in no way be construed, however, as limiting the broad scope of the invention.

EXAMPLE I

Methods

Figure 1A:
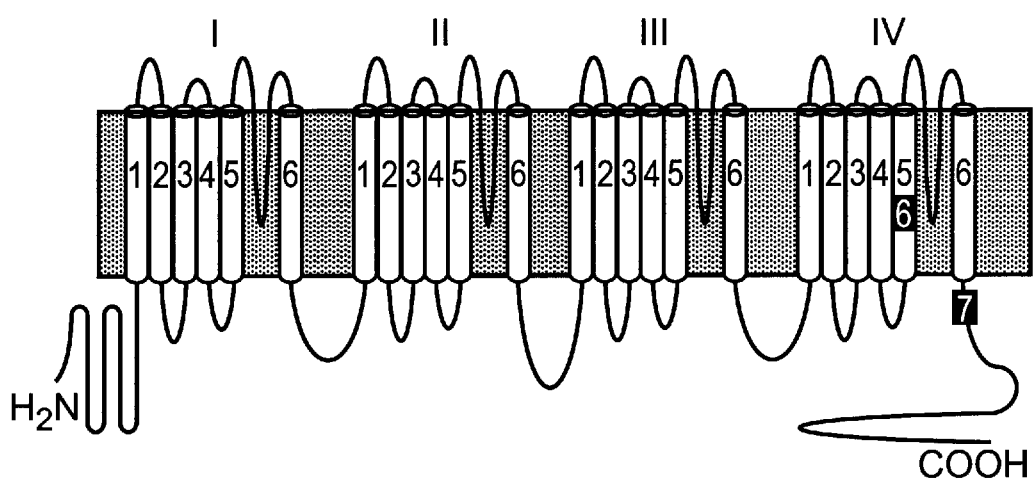
FIG. 1A: Cartoon showing the general structure of $α_1$ subunits. Black boxes, labeled 6 & 7, identify the position of primers used for successful amplification of a portion of genomic DNA encoding the Drosophila $α_1$ sequence.
Figure 3:
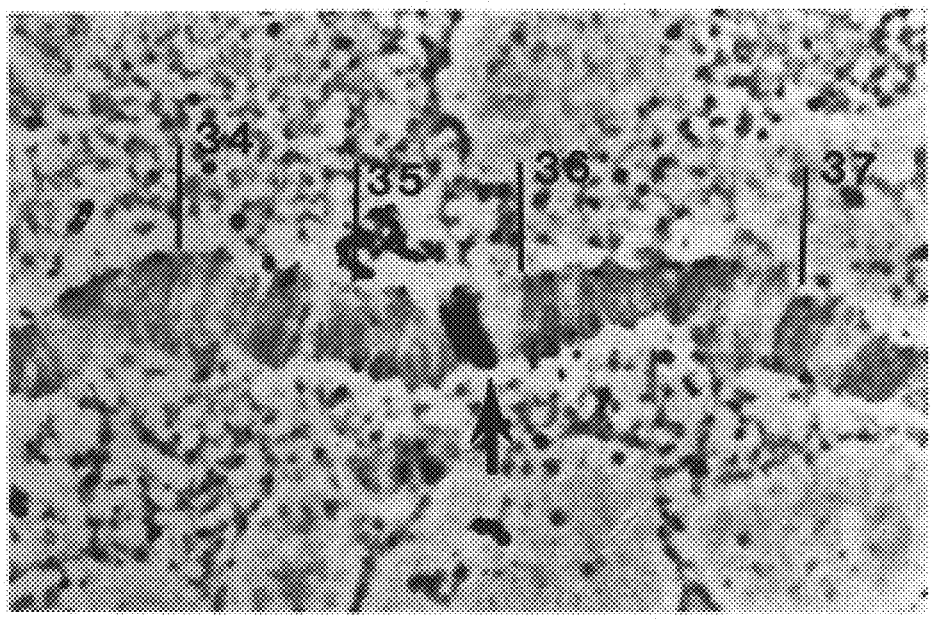
FIG. 3 is a photomicrograph of the chromosome mapping of the $α_1$ subunit DmcalD (In situ hybridization to Drosophila salivary gland polytene chromosomes using a biotinylated probe (bases 4252–5795, FIG. 2) mapped this gene to 35EF on the left arm of chromosome 2. Numbered divisions for this section of chromosome 2L are marked and the hybridization signal is indicated by the arrow).

1. Polymerase Chain Reaction ("PCR"):

Primer sites were selected by aligning cDNA sequences for $\alpha_1$ subunits of calcium channels from rabbit skeletal muscle (Tanabe et al. (1987), Nature, vol. 328, pp.313–318, which disclosure is hereby incorporated by reference), heart (Mikami et al., (1989), Nature, vol. 340, pp. 230–233, which disclosure is hereby incorporated by reference) and brain (Mori et al., (1991), Nature, vol. 350, pp. 398–402, which disclosure is hereby incorporated by reference), rat aorta (Koch et al., (1990), J. Bio. Chem., vol. 265, pp. 17786–17791, which disclosure is hereby incorporated by reference), and fish skeletal muscle (Grabner et al., (1991), Proc. Natl. Acad. Sci. USA, vol. 88, pp. 727–731, which disclosure is hereby incorporated by reference to the most highly conserved regions with the least amount of codon degeneracy. Inosine was used when A, T, G, and C were all a possibility at a given site (Martin et al., (1985), Nucleic Acids Res., vol.13, p. 9927 and Knoth et al., Nucleic Acids Res. vol. 16, p.11932, which disclosures are hereby incorporated by reference). FIGS. 1 and 3 show the positions of a successful primer pair (P6 and P7) in the carboxy portion of the channels. Primer P6 lies within IVS5 and has the sequence: 5'AT[C/T/A]G[T/C]IATG[C/T]TITT[C/T]TT[CT]ATITA[C/T]GC3' (SEQ. ID. NO. 5") Primer P7 lies between IVS6 and the putative EF hand and has the sequence: 5'TC[G/A]TCIA[G/A][G/A]TG[G/A]TGIGGICCIA-[G/A][GA/A/T]AT3' (SEQ. ID. NO. 6). FIG. 1 additionally shows that there are 4 repeat units designated I, II, III, and IV which are similar in structure to each other. Within each repeat there are six transmembrane domains designated 1 through 6 (aka S1-S6) which are thought to form $\alpha_1$-helical structures through the membrane. The S4 regions have positively charged amino acids every 3 to 4 residues which are thought to align on one side of the $\alpha$-helix to form the voltage sensor. In addition to the membrane spanning domains, the extracellular region which falls between regions S5 and S6 in each repeat is thought to dip into the membrane forming short segments SS1 and SS2 involved in the ion selectivity filter of the channel. Furthermore, the cDNA clones shown in FIG. 1 were isolated from a head library using as a probe the 499 base pair PCR amplification product from primers shown in A (SH22C) or the 5' ends of clones SH22C or W8A. The diagram shows the overlap among the clones. FIG. 3 further shows that in situ hybridization to Drosophila salivary gland polytene chromosomes using a biotinylated probe (bases 4252–5795, FIG. 2) mapped this gene to 35EF on the left arm of chromosome 2. This same position was seen using a variety of other probes from W8A and SH22C (data not shown) suggesting that these overlapping cDNAs (FIG. 1) are encoded by the same gene.

2. Reaction Conditions For Cross Species Amplifications:

The template for the polymerase chain reaction was 150 ng of Drosophila genomic DNA prepared from adult flies as described by Jowett, T. (in: *Drosophila: A Practical Approach*, Roberts, D. B. (ed.) IRL Press (Oxford)(1986)) which disclosure is hereby incorporated by reference. The 50 µL reaction mixture contained: 0.2 mM of each of the dNTPs, 10 mM Tris (hydroxymethyl) aminomethane (Tris) buffer pH 8.3, 50 mM KCl 1.5 mM $MgCl_2$, 0.001% gelatin, 0.1 µM of each primer, and units AmpfiTaq™ DNA polymerase from Perkin Elmer Cetus (Norwalk, Conn.). Following an initial 2 minutes at 95° C., the following cycle was repeated 35 times: denaturation 2 minutes at 95° C., annealing 2 minutes at 40° C., extension 2 minutes at 72° C. The final extension was 10 minutes at 72° C. PCR products were analyzed by electrophoresis of 10 µL of reaction mix on a 1% agarose gel.

3. DNA Sequencing

The band containing the PCR product of interest was extracted from the gel by the phenol/freezing method of Benson, S. A., (1984), *Biotechniques*, vol. 2, pp. 66–68, which disclosure is hereby incorporated by reference), resuspended in Tris EDTA buffer, ph 8.0 (TE buffer, ph 8.0) (Sambrook et al., (1989), In: *Molecular Cloning: A Laboratory Manual*, 2nd ed., Cold Spring Harbor Laboratory Press, Cold Spring Harbor, N.Y., which disclosure is hereby incorporated by reference) to a concentration of 10–20 g/µl and 25 ng template was used for reamplification in 100 µl reactions prior to sequencing. The PCR conditions were as described above, except that the annealing temperature was 65° C. Sequencing templates were purified and concentrated using Centricon-100 columns (Amicon, Danvers, Mass.). Double-stranded DNA sequencing was performed on an Applied Biosystems Sequencer Model 373A using the dideoxy chain termination method with fluorescent dye-tagged M13 or SP6 primers according to instructions supplied with a Taq Dye Primer Cycle Sequencing kit (Applied Biosystems, Inc., Foster City, Calif.). Using this approach 300–400 bases were generally read from each template. Each segment of DNA was sequenced at least twice in each direction. For sequencing PCR products without subcloning or for sequencing phage clones, new tailed primers were synthesized adding an 18 nucleotide M13 or SP6 sequence to the 5' end of the original PCR primer sequence.

Figure 1B:
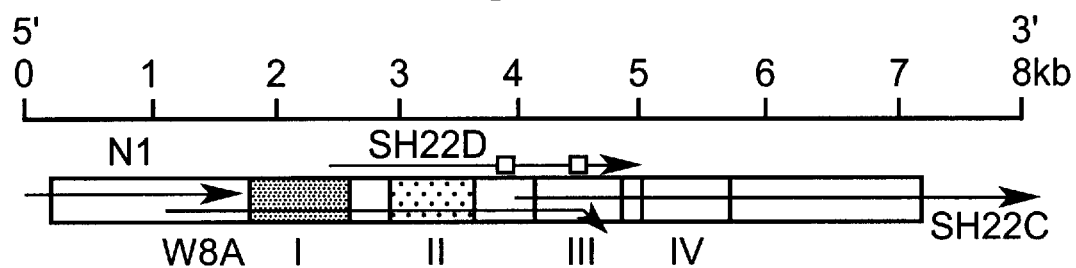
FIG. 1B: The region extending diagonally from the 3' end of W8A indicates an alternatively spliced sequence which is not present in clone SH22C. The small open boxes in SH22D.indicate positions of the alternative splice regions studied in Table 1. The large rectangular box indicates the open reading frame for the Drosophila $α_1$ subunit starting with the first possible methionine codon (designated met1 herein). The positions of the repeats (I–IV) are shown as shaded gray boxes within the open reading frame).

4. Screening for cDNA Clones:

A total of $2\times10^5$ plaque-forming units (pfu) of a Drosophila head cDNA library in λgt11 (Itoh et al., (1986), *Proc. Natl. Acad. Sci. USA*, vol. 83, pp. 4081–4085, which disclosure is hereby incorporated by reference, generously provided by Dr. Paul Salvaterra, Beckman Research Institute, Duarte, Calif.) were screened on Nylon membranes (ICN, Costa Mesa, Calif.) using the 499 base pair amplification product from primer pair P6/P7. The probe was random-prime labeled with $^{32}$P-dCTP using the Multiprime Kit (Amersham Corp., Arlington Heights, Ill.). Standard conditions were used for prehybridization, hybridization, and washing (Sambrook et al., (1989), cited elsewhere herein, which disclosure is hereby incorporated by reference). A 4 kb cDNA clone (SH22C) was isolated initially and further clones (including W8A and SH22D) were obtained using the 5' end of SH22C. Since W8A did not contain the 5' end of the open reading frame, rapid amplification of cDNA ends was done with the 5' rapid amplification of CDNA ends (RACE) kit from Clontech (Palo Alto, Calif.) and a primer from the 5' end of W8A and extended the sequence 360 bases upstream. Since this extension was still incomplete, the 5' end of W8A was also used to isolate the N1 cDNA clone (FIG. 1B).

5. In situ Hybridization To Salivary Gland Chromosome Squashes:

The map position of cloned cDNAs was determined as described by Engels et al., (1985), Focus, vol. 8, pp. 6–8 and Murtagh et al., (1993), *Biochemistry*, vol. 32, pp. 6011–6018, which disclosures are hereby incorporated by reference, using biotinylated probes hybridized to salivary gland chromosomes.

6. Northern Blots:

Heads, bodies and legs were isolated from frozen adult flies as described by Schmidt-Nielsen et al. (1977), *J. Neurochem.*, vol. 29, pp.1013–1029, which disclosure is hereby incorporated by reference. Total RNA was prepared and poly(A)-mRNA isolated by the guanidinium isothiocyanate-CsCl gradient method followed by one passage over oligo (dT)cellulose columns (Sambrook et al., (1989), cited elsewhere herein, which disclosure is hereby incorporated by reference). 10 µg of poly(A)+ RNA in TE was added to each lane of 0.8% agarose gel containing 6.3% formaldehyde and electrophoresed for 3 hours at 100V using 1×MOPS buffer (3-(N-Morpholino)propanesulfonic acid) according to Sambrook et al. (1989), cited elsewhere herein, which disclosure is hereby incorporated by reference. The gel was capillary blotted onto a nylon membrane (Schleicher & Schuell, Keene, N.H.) and fixed by UV crosslinking. Prehybridization was for 6 hours at 42° C. in 50% deionized formamide, 5×SSPE, 5×Denhardt's, 0.5% sodium dodecyl sulfate (SDS), 100 µg/ml denatured salmon sperm DNA and then $10^6$ cpm/ml $^{32}$P-labeled cDNA probe was added and the incubation continued for 16 hr at 42° C. The blot was washed 2 times for 15 minutes each at room temperature in 2×SSC, 0.1% SDS followed by 2 more washes for 30 minutes each at 65° C. in 0.1×SSC, 0.1% SDS. The blots were exposed to X-ray film at −70° C. Standard solutions (SSC, SSPE, Denhardt's) are as described by Sambrook et al. (1989), cited elsewhere herein, which disclosure is hereby incorporated by reference.

7. Reverse Transcriptase-Coupled PCR ("RT-PCR"):

First strand cDNA synthesis in 50 µL was conducted at 42° C. for 60 minutes using 1200 units/ml AMV (avian myeloblastosis virus) reverse transcriptase and 80 µg/mi poly(A)+ mRNA as described by Gubler, U. and Hoffman, B J., (1983), Gene, vol. 25, pp. 263–269, which disclosure is hereby incorporated by reference, with the following changes: 40 µg/ml oligo dT primer, 50 mM KC1, 0.5 mM spermidine, 1 mM each DNTP, 800 units/ml RNasin. The reaction was stopped with 1 mM EDTA (ethylenediaminetetraacetic acid) and 0.5 µL of the reaction mix was used for a 50 µL PCR as described for the cross species amplifications above except that 0.005% gelatin was used and the amplification was 35 cycles of: 95° C. 1 minute, 60° C. 1 minute, 72° C. 1 minute, followed by a final 5 minute extension at 72° C. Forty µL of the amplification reaction was electrophoresed and extracted from an agarose gel by the freezing phenol method as described above. DNA pellets were resuspended in 20 µL distilled water and 6 µL was used for each restriction enzyme digestion described in Table 1.

TABLE 1

RT-PCR followed by restriction enzyme digestion reveals more DmcalD message heterogeneity in heads than in bodies or legs

| Region amplified by RT-PCR | Source of mRNA | mRNA isoforms present | Diagnostic restriction enzyme |
|---|---|---|---|
| Cytoplasmic loop between II & III (bases 3830–4033) | Heads | (1)A, D | Hinf I |
| | Bodies | A | Hinf I |
| | Legs | A | Hinf I |
| IIIS3 to Loop between IIIS5 & S6 (bases 4251–4635) | Heads | C, D | Pst I or RSA I |
| | Bodies | C | Pst I or RSA I |
| | Legs | D | Pst I or Rsa I |

(1)A, C, D refer to splice forms found in different cDNA clones (A = W8A, C = SH22C, D = SH22D) in the regions indicated by open boxes in the SH22D diagram in FIG. 1B. Although the alternative forms were similar in size, they could be distinguished in the PCR amplification products following digestion with the indicated restriction enzymes.

8. In situ Hybridization To Embryo Whole Mounts:

Whole mount in situ hybridization to Drosophila embryos was done as described by Tautz and Pfeifle, (1989), cited elsewhere herein, which disclosure is hereby incorporated by reference, using the formaldehyde fixation method. A single-stranded digoxigenin-labeled cDNA probe was prepared from a PCR product (bases 6488–6777 of the coding region, FIG. 2) which had been extracted from the gel using an Ultrafree-MC filter unit from Millipore Corp. (Bedford, Mass.), and concentrated using a Centricon-30 spin column. This purified PCR product (200 ng) was used as template to prepare single-stranded antisense DNA in a total volume of 25 µl using 5 µl of the nucleotide solution from vial 6 in the Genius Kit from Boehringer Mannheim (Indianapolis, Ind.), 2 µl primer stock for the antisense strand (10µM), and 0.3 µl Taq polymerase (5U/µl). Amplification conditions for the synthesis of this single-stranded probe were: 94° C. 45 seconds, 55° C. 30 seconds, and 72° C. for 60 seconds, for a total of 25 cycles. Labeled probe was stored at −20° C.

EXAMPLE II

Strategy For Cloning An $\alpha_1$ Subunit Of Drosophila Calcium Channels

When these studies were conducted, it was evident that Drosophila had multiple calcium channel subtypes, at least some of which had a different pharmacological specificity from that reported for the cloned dihydropyridine from vertebrate skeletal muscle (Pauron et al., (1987), Biochemistry, vol. 26, pp. 6311–6315; Greenberg et al., (1989), Insect. Biochem., vol. 19, pp. 309–322; Pelzer et al., (1989), EMBO J., vol. 8, pp. 2365–2371; Glossmann et al., (1991), Br. J. Pharmacol., vol. 102, pp. 446–452, which disclosures are hereby incorporated by reference). It was not clear, however, how much structural conservation would exist between Drosophila calcium channel subunits and those which had been cloned from vertebrates (Tanabe et al., (1987), Nature, vol. 328, pp. 313–318; Mikami et al., (1989), Nature, vol. 340, pp. 230–233; Koch et al., (1990), J. Biol. Chem., vol. 265, pp.17786–17791; Mori et al., (1991), Nature, vol. 350, pp. 398–402; and Grabner et al., (1991), Proc. Natl. Acad. Sci. USA, vol. 88, pp. 727–73 which disclosures are hereby incorporated by reference). Since both the Drosophila head binding activity and the cloned vertebrate subunits were known to be phenylalkylamine sensitive, it was reasoned that at least some regions of the sequence were likely to be conserved. Using a polymerase chain reaction ("PCR") based strategy allowed focus on short regions for primer design which were most likely to be conserved across species. Drosophila genomic DNA was used as a template to avoid assumptions concerning the tissue and stage in development when calcium channels would be expressed. Products approximately the same size as (or larger than) that predicted from vertebrate $\alpha_1$ subunits were sequenced to identify those which encoded deduced amino acid sequences with structural similarity to the corresponding region of vertebrate calcium channel $\alpha_1$ subunits. By including products larger than predicted from the vertebrate sequences, it allowed for the occurrence of introns in the genomic DNA used as template.

The product from primer pair P6/P7, spanning the region from IVS5 to a cytoplasmic region following IVS6 (FIG. 1A), had a deduced amino acid sequence very similar to that of vertebrate a I subunits except that the 3' end of the IVS5 coding region and the middle of the IVS6 coding region were disrupted by 59 and 60 base pair introns, respectively. These introns were readily recognized using codon preference analysis from the University of Wisconsin Genetics Computer Group (GCG) software package.

Northern analysis showed that this Drosophila genomic fragment recognized a message that was expressed at a relatively high level in heads as would be expected for a neuronal calcium channel component (Greenberg et al., (1989), Insect Biochem., vol. 19, pp. 309–322, which disclosure is hereby incorporated by reference), so an adult head cDNA library was screened. The two longest cDNA clones, W8A and SH22C, with an overlap of 572 nucleotides were sequenced and combined as shown schematically in FIG. 1B. Although the sequence match between the two clones is excellent within the region of overlap (only 3 nucleotide discrepancies, indicated by open triangles in FIG. 2), there is a region of 149 nucleotides in W8A which shows no sequence similarity with SH22C. This nonmatch region begins in the intracellular loop between IIIS4 and S5 and extends into transmembrane domain IIS5. In situ hybridization to salivary gland chromosomes (FIG. 3) showed that both W8A and SH22C mapped to the same position at 35EF on the left arm of the second chromosome suggesting that the two cDNA clones are derived from the same gene. This was confirmed by sequencing a genomic clone and the SH22D cDNA clone in the regions flanking the non-overlap section. Sequence analysis revealed two alternatively spliced exons in this region.

The 5' end sequence of the cDNA was derived from the N1 clone. In addition, 5' RACE (rapid amplification of cDNA ends) was done starting with poly (A)+ mRNA from Canton-S and a primer from the 5' end of W8A. The RACE product extended only 360 bases upstream from the end of W8A whereas N1 clone provided 1116 bases upstream of the 5' end of W8A. In the 360 bases of overlap between the RACE product and clone N1, there was an exact match except for three bases (indicated by the closed triangles in FIG. 2) within the proposed open reading frame. These differences did not affect the amino acid sequence and most likely represent sequence polymorphisms between DNA from different wild-type sources.

Example III

Structural Features Of The CDNA Sequence

The complete nucleotide sequence and the deduced amino acid sequence for the Drosophila $\alpha_1$ subunit are shown in FIG. 2. (SEQ. ID. NO. 1 and SEQ. ID. NO. 2, respectively). Bases are numbered from the first of five possible AUG initiation codons all of which are marked with a *. Three nucleotides which differ in sequence between the N1 clone and the 5' RACE product using Canton-S poly (A)+ mRNA are indicated with a closed triangle above the nucleotide. The sequence shown is from the N1 clone. The 3 nucleotides which differ between cDNA clones W8A and SH22C are indicated with an open triangle above each. The sequence shown is. that found in W8A because those nucleotides have also been found in the corresponding genomic DNA sequence (D. Ren and L. M. Hall, unpublished). The deduced amino acid sequence is shown below the DNA sequence and the proposed transmembrane domains are indicated as labeled lines underneath the corresponding amino acid sequences. The position of a proposed calcium binding domain (the EF hand, Babitch, J., ((1989), Nature, 346: 321–322, which disclosure is hereby incorporated by reference) is indicated by the heavy labeled line under the amino acids involved. The in-frame stop codons preceding and following the open reading frame are indicated with a dark dot underneath the first base in each codon. The positions of the primers used in the initial PCR amplification of genomic DNA are indicated by the boxed gray areas of the nucleic acid sequence with labels P6 and P7 directly above them. This sequence was submitted to GenBank and received Accession No. U00690.

The carboxy terminus of the deduced protein is unambiguously determined by the TAG stop codon at nucleotide position 7549–7551 which is followed by 10 additional in-frame stop codons (indicated by a black dot below the first nucleotide in each triplet). There is no polyadenylation consensus sequence (AAUAAA) in the 3' untranslated region, so there may be some additional 3' sequence which was not included in the SH22C clone. The total assembled cDNA sequence (~8 kb) is about 1.5 kb shorter than the smallest message observed in Northern blotting experiments (FIG. 4). This may be due to missing 5' and/or 3' untranslated regions in the cDNA clones sequenced and/or to extensive polyadenylation.

With reference to FIG. 4, there is shown the Northern blot of poly(A)+ mRNA (10 µ/lane) isolated from bodies (B), heads (H), or legs (L) was probed with a PCR fragment (bases 6141/7511, FIG. 2) from clone SH22C and washed at high stringency. The tics on the right of the figure indicate positions of bands. The lower inset shows the results of reprobing with ribosomal protein 49 cDNA (rp49) to control for mRNA recovery and gel loading differences since rp49 is expressed uniformly throughout the organism and throughout the different developmental stages (see B below) (O'Connell, P. O. and Rosbash, M., (1984), Nucleic Acids Res., vol. 12, pp. 5495–5513, which disclosure is hereby incorporated by reference). A Northern blot (as in part A) consisting of mRNA isolated from embryos of different ages was hybridized with a $^{32}$P-labeled double-stranded probe from W8A (nucleotides 961 to 2214, FIG. 2).

The most likely start translation start site is in the first methionine marked with a * since it is preceded by 3 in-frame stop codons within the 156 bases upstream as shown in FIG. 2. However, there are 4 additional methionines (also marked with a * underneath the M symbol in FIG. 2) encoded in the region between the first methionine and IS9. The area immediately upstream of each of these methionine codons was compared with the Drosophila translation start site consensus sequence (C/A AA A/C AUG) (Cavener, D. R., (1987), Nucleic Acids Res., vol. 15, pp. 1353–1361, which disclosure is hereby incorporated by reference).

The first methionine shows 0/4 matches. Although it lacks an A at the crucial −3 position, it has the second most commonly used base (G) at this position. The second, third and fifth methionines all have an A in the −3 position. In addition, the second (M494) and fifth (M553) methionines show 3 out of 4 nucleotide matches to the upstream consensus sequence for Drosophila. In Drosophila, the average fit to the 4 nucleotide consensus positions immediately upstream of a start codon is 3.1 matches. On the basis of nucleotide sequence, met494 and met553 could be start site candidates, however there are no upstream in-frame stop codons preceding them. Therefore, it is believed that met1 is the start site.

Example IV

Tissue Distribution And Heterogeneity Of Dmca1D Message Expression

Figure 4A:
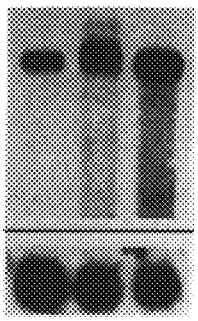
FIG. 4 illustrates the tissue and temporal expression of the Drosophila $α_1$ subunit mRNA by Northern blotting.
Figure 4B:
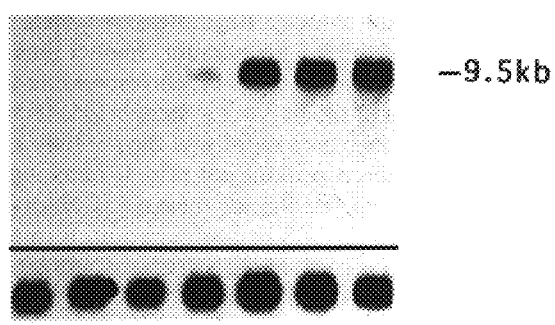

The relative expression of Dmca1D transcripts in different body parts was determined by Northern blot analysis using rp49 (a uniformly expressed ribosomal protein mRNA) (O'Connell, P. O. and Rosbash, M., (1984), Nucleic Acids Res., vol. 12, pp. 5495–5513, which disclosure is hereby incorporated by reference) as a control for amount of RNA loaded into each lane. As shown in FIG. 4A, poly (A)+ RNA from bodies (B), heads (H), and legs (L) were compared following hybridization with a probe from the 3' end of clone SH22C. This probe contains the coding sequence for the nonconserved carboxy terminus of the a, subunit. All three preparations show a major band at 9.5 kb and a minor band at 12.5 kb. The minor band is seen most clearly in the head preparation. In addition, the head preparation shows a second major band at 10.2 kb. A similar result (data not shown) was obtained using a probe derived from W8A. The relationship among the three mRNA size classes is not known. The largest size class (12.5 kb) is a very weak signal in all lanes suggesting that it might be an unprocessed transcript or the product of another gene picked up by sequence similarity. Compared to messages expressed in heads, there is less heterogeneity in the message expressed in the bodies and legs since only one major band (9.5 kb) is visible.

To further investigate the difference in message heterogeneity among heads, bodies and legs, two regions where sequence data from 3 different cDNA clones (W8A, SH22C, and SH22D; see FIG. 1) had shown differences were reviewed. The positions of the regions studied are shown as open boxes in the SH22D clone in FIG. 1B. These differences could be most easily distinguished by RT-PCR (reverse transcriptase coupled PCR) amplification followed by a diagnostic restriction enzyme digestion. It should be noted that the differences in the actual nucleic acid sequences were extensive as expected for alternative splice products and could not be explained by single base changes due to sequence polymorphisms (D. Ren and L. M. Hall, unpublished). As shown in Table 1, in each of the two regions tested for alternative splicing, two different forms were found in heads but only a single form was found in bodies or legs. Embryos (which express this subunit only in the nervous system as shown in FIG. 5 and discussed below) show the same pattern of heterogeneity seen in heads. Taken together, these results again suggest there may be more functional heterogeneity in Dmca1D type calcium channels in neuronal tissue than elsewhere in the fly.

Example V

Temporal Pattern. Of Expression Of Dmca1D

To determine when the Dmca1D message is expressed in Drosophila embryos, a Northern blot (FIG. 4B) containing poly(A)+ mRNA from a variety of embryonic stages was probed with two different Dmca1D specific probes: one from W8A (shown in FIG. 4B) and one from SH22C (from nucleotide 5665 in IVS6 to the end, data not shown). Regardless of which probe was used, expression of the 9.5 kb calcium channel message is detected faintly in embryos at 9 to 12 hours corresponding to the time when condensation of the nervous system begins (Kankel et al., (1980), In: The Genetics and Biology of Drosophila, vol. 2, Ashburner, M. and Wright, T. R. F., eds., Academic Press (New York), which disclosure is hereby incorporated by reference). Expression increases rapidly as the nervous system matures within the embryo, peaking just prior to hatching. A second peak of expression of the 9.5 kb message is observed in late pupal stages around 73 to 108 hours post puparium formation when the nervous system is completing a dramatic reorganization (F. Hannan, unpublished observations, which disclosure is hereby incorporated by reference).

Example VI

Embryonic Whole Mount in situ Hybridization

To determine where the message for this $\alpha_1$ subunit is expressed, a digoxigenin-labeled antisense probe was used on embryonic whole mounts. As shown in the 13–15 hour embryo in FIG. 5, the Dmca1D subunit was preferentially expressed in the nervous system. A single-stranded, antisense DNA probe labeled with digoxigenin was hybridized to embryo whole mounts and the signal detected as described by Tautz, D. and Pfeifle, C., (1989), Chromosoma, vol. 98. pp. 81–85, which disclosure is hereby incorporated by reference. The dark staining pattern highlights the round, dorsal cerebral hemisphere and the ventral ganglion which comes off the ventral side of the sphere and curves posteriorly on the ventral surface of the embryo.

Example VII

General Structural Features Of The Deduced Amino Acid Sequence

Figure 6A:
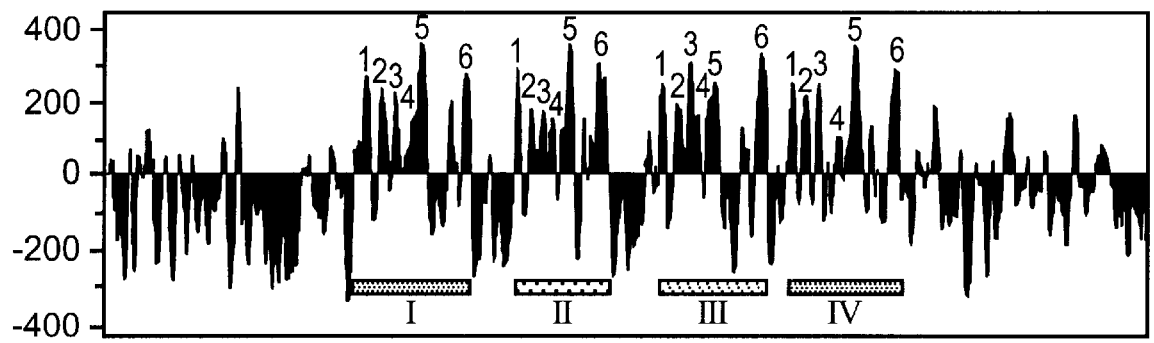
Figure 6B:
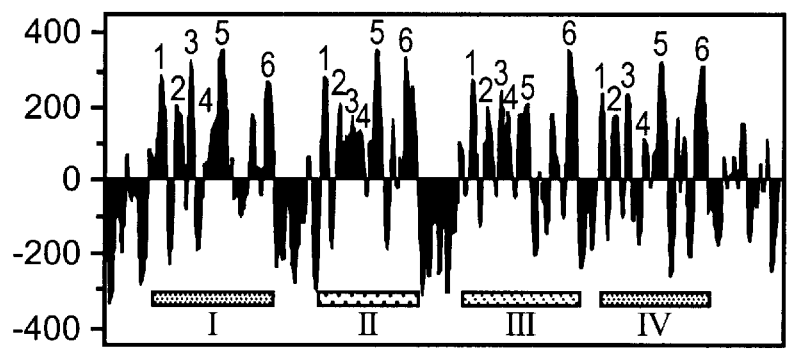

Using the first in-frame AUG (met1) following a series of in-frame stop codons as the translation start site, FIG. 2 shows that the open reading frame of the combined cDNA clones would encode a protein of 2516 amino acids with an expected molecular weight of 276,493 and a predicted pI of 5.04. The hydrophobicity plot of this complete deduced protein is shown in FIG. 6A where it is compared with the calcium channel type D $\alpha_1$ subunit from rat brain (FIG. 6B). Hydropathy plots were determined using the method of Kyte, J. and Doolittle, R. F., (1982), J. Mol. Biol., vol. 157, pp. 105–132, which disclosure is hereby incorporated by reference, with the GeneWorks software. If the second AUG is the actual translation start site, the Drosophila protein would consist of 2023 amino acids and have a predicted molecular weight of 224,369 and a pI of 6.49. If it begins with the fifth AUG, the protein would consist of 1964 amino acids with a predicted molecular weight of 218,580 and a predicted pI of 6.78. Just as in the vertebrate calcium channel $\alpha_1$ subunits, the Drosophila subunit shows four repeat domains (indicated by the bars in FIG. 6 labeled I through IV). Each of these repeats shows 6 hydrophobic domains (labeled 1 through 6) which would be long enough to span the membrane. The resemblance to the vertebrate $\alpha_1$ hydropathy plots is striking in the hydrophilic as well as the hydrophobic domains. The only places where there are differences are in the cytoplasmic amino and carboxy terminal tails. Both regions are much longer in Drosophila than in the vertebrate homologs. Although there is striking similarity in the region of the carboxy tail closest to transmembrane region IVS6, the similarity falls off after about 163 amino acids from the end of the IVS6 region when the Drosophila sequence is compared with the rat brain D sequence or after 199 amino aids when compared with the rabbit skeletal-muscle sequence (comparison not shown). On the amino terminal end the similarity to the vertebrate homologs falls of after about 40 to 50 amino acids upstream of the beginning of IS1.

The repeat structure and the pattern of the hydrophobic domains puts this newly cloned Drosophila protein in the same superfamily as the voltage-gated sodium and calcium channels. As shown in Table 2, when the deduced protein is compared with available sequences for sodium and calcium channels, in general there is more similarity in amino acid sequence between the Drosophila clone and vertebrate calcium channels (ranging from 63.4 to 78.3%) than between this sequence and sodium channels (57.9 to 58.9%) even if the sodium channel is from Drosophila. These differences are even more striking if amino acid identity is considered (42.7 to 64.2% identity for calcium channels versus 29.6 to 30.5% for sodium channels). Thus, based on overall sequence similarity, the newly cloned gene would be designated as a member of the calcium channel gene family.

TABLE 2

Comparison of a Drosophila calcium channel $\alpha_1$ subunit with the vertebrate a, subunits at amino acid level.

| DHP Sensitivity | Similarity | Identity | Loop II/III* | References |
|---|---|---|---|---|
| +Rat Brain-D | 78.3 | 64.2 | 134 | Hui et al., 1991 |
| +Rabbit Skeletal Muscle | 72.4 | 56.1 | 138 | Tambe et al., 1987 |
| +Human Brain | 71.3 | 55.5 | 134 | Williams et al, 1992b |
| +Rabbit Lung | 70.2 | 54.1 | 125 | Biel et al., 1990 |
| +Carp Skeletal Muscle | 70.0 | 51.7 | 139 | Grabner et al., 1991 |
| +Rat Brain-C | 69.9 | 54.1 | 150 | Snutch et al., 1991 |
| +Rat Heart | 69.6 | 53.3 | 147 | Mikarni et al., 1989 |
| +Rat Aorta | 68.7 | 53.0 | 147 | Koch et al., 1990 |
| −Rat Brain-A | 65.2 | 45.1 | 479 | Starr et al., 1991 |
| −Rabbit Brain- 1 | 64.5 | 44.2 | 539 | Mori et al., 1991 |

TABLE 2-continued

Comparison of a Drosophila calcium channel $\alpha_1$ subunit with the vertebrate a, subunits at amino acid level.

| DHP Sensitivity | Simi-larity | Iden-tity | Loop II/III* | References |
|---|---|---|---|---|
| –Rat Brain-B | 63.4 | 43.7 | 438 | Dubel et al., 1992 |
| –Human N-type | 63.4 | 42.7 | 451 | Williams et al., 1992a |
| Na⁺ channel (Drosophila) | 58.9 | 30.5 | | Loughney et al., 1989 |
| Na⁺ channel (Rat skel. muscle) | 57.9 | 29.6 | — | Trimmer et al., 1989 |

*This is the cytoplasmic loop between IIS6 and IISI. In Dmca1D the length of this loop is 129 amino acids.

Within the calcium channel group, the Drosophila sequence shows the closest relationship to rat brain type D. The next highest scoring channel frorn rabbit skeletal muscle shows ~8% less identity and ~6% less similarity than the rat brain type D channel. Based on this sequence similarity hierarchy and on its expression in the nervous system, the Drosophila channel was designated as Drosophila melanogaster calcium channel alpha 1 subunit type D ("Dmca1D").

TABLE 3

Comparison of alternating positive charges in S4 transmembrane domains in calcium channel $\alpha_1$ subunits.
Numbers of positively charged amino acids in S4 domain

| Clone Source† | #K | R | T | K | R | T | K | R | T | K | R | T |
|---|---|---|---|---|---|---|---|---|---|---|---|---|
| Drosophila head (DmcalD) | 1 | 4 | 5 | 2 | 3 | 5 | 1 | 5 | 6 | 2 | 3 | 5 |
| Carp skeletal muscle | 1 | 4 | 5 | 1 | 4 | 5 | 1 | 5 | 6 | 1 | 4 | 5 |
| Rabbit skeletal muscle | 1 | 4 | 5 | 2 | 3 | 5 | 1 | 5 | 6 | 1 | 4 | 5 |
| Human brain | 1 | 4 | 5 | 1 | 4 | 5 | 1 | 5 | 6 | 1 | 4 | 5 |
| Rat brain-D | 1 | 4 | 5 | 1 | 4 | 5 | 1 | 5 | 6 | 1 | 4 | 5 |
| Rat brain-C | 1 | 4 | 5 | 1 | 4 | 5 | 1 | 5 | 6 | 1 | 4 | 5 |
| Rat aorta | 1 | 4 | 5 | 1 | 4 | 5 | 1 | 5 | 6 | 1 | 4 | 5 |
| Rabbit heart | 1 | 4 | 5 | 1 | 4 | 5 | 1 | 5 | 6 | 1 | 4 | 5 |
| Rat brain-B | 1 | 0 | 1 | 2 | 1 | 3 | 2 | 3 | 5 | 1 | 2 | 3* |
| Rabbit brain-1 | 1 | 4 | 5 | 2 | 3 | 5 | 2 | 4 | 6 | 1 | 3 | 4* |
| Rat brain-A | 1 | 4 | 5 | 2 | 3 | 5 | 2 | 4 | 6 | 1 | 3 | 4* |

†The references for sequences used in this comparison are given in Table 2.
K = lysine; R - arginine; T - total positively charged side chains placed every 3–4 residues.
*For this domain; these $\alpha_1$ subunits have a glutamine (Q) in the position occupied by arginine (R) or lysine (K) in other species. This position is the fourth amino acid from the previous positively charged amino acid and falls near the cytoplasmic end of this transmembrane α-helix. There is an arginine residue in the immediately preceding position for each of these proteins.

As for other members of the voltage-sensitive cation channel family, each of the S4 transmembrane domains of the newly cloned channel subunit shows positively charged amino acids (R=arginine or K=lysine) every third or fourth amino acid. In a commonly proposed model, this pattern would put all of the positively charged side chains on the same side of an alpha helix so that they sit in the membrane as the voltage-sensor (Stuhmer et al., (1989), *Nature*, vol. 339, pp. 597–603, which disclosure is hereby incorporated by reference). As summarized in Table 3, the Drosophila protein shows the same general pattern as the majority of other calcium channels with 5 positively charged side chains the S4 helices in domains I, II, and IV and 6 in domain III. Only the rat brain A and B and rabbit brain-1 channels deviate from this pattern.

Example VIII

Proposed Calcium Binding EF Hand Region

Another feature commonly found in both sodium and calcium channel $\alpha_1$ subunits is a protein motif known as the EF hand, which consists of two α-helices flanking a calcium binding loop (Babitch, J., (1 990), *Nature*, vol. 346, po. 321–322, which disclosure is hereby incorporated by reference). As indicated by the heavy underlined region beginning 20 amino acids downstream from the IVS6 region in FIG. 2, an EF hand is found in the Drosophila sequence. As shown in Table 4, in the Tufty-Kretsinger test (Tufty, R. M. and Kretsinger, R. H., (1975), *Science*, vol. 197, pp. 167–169, which disclosure is hereby incorporated by reference) the Dmca1D sequence has 11 matches (out of 16 possibilities) for residues important for calcium binding. The number of matches for Dmca1D can be increased to 14 by allowing conservative amino acid substitutions. Many vertebrate calcium channel $\alpha_1$ subunits show a similar pattern of matching (Babitch, J., (1990), *Nature*, vol. 346, pp. 321–322, which disclosure is hereby incorporated by reference). Again, the Drosophila sequence shows more similarity to calcium channels than to sodium channels in this critical area.

Example IX

Ion Selectivity Filter

A portion of the sodium channel involved in the ion selectivity filter has been identified within short segment 2 (SS2) lying between S5 and S6 in all repeats (Heinemann et al., (1992), *Nature*, vol. 356, pp. 441–443, which disclosure is hereby incorporated by reference). By changing a single amino acid residue (K1422 in repeat III or A1714 in repeat IV of rat sodium channel II) to a negatively charged glutamic acid (E) (as found in calcium channels), the ion selectivity of the channel can be changed from that of a sodium channel to resemble that of a calcium channel. Recently, Tang et al., (1993), *J. Biol. Chem.*, vol. 268, pp. 13026–13029, which disclosure is hereby incorporated by reference, have done the reciprocal experiment on cardiac calcium channels and have shown that modification of conserved glutamate residues in the SS2 region of repeats I, II, or IV alters the ion selectivity and permeability of calcium channels. Table 5 compares the SS2 sequences of the newly cloned Dmca1D cDNA with those of other sodium and calcium channels. In general, the new Drosophila sequence resembles the calcium channel sequences more closely than it does the sodium channel sequences. In the crucial region of repeats I, II, III and IV all of the negatively charged glutamic acids (bold E) found in calcium channels have been conserved in the Drosophila sequence, providing further evidence that Dmca1D encodes a calcium channel subunit. The conservation of glutamate residues in all four SS2 regions is consistent with the suggestion of Tang et al. (1993), cited above, which disclosure is hereby incorporated by reference, that these residues form a ring in the pore-lining SS1-SS2 region involved in ion selectivity and permeability.

Example X

Possible Sites for Posttranslational Modification of the Protein Encoded by Dmca1D There are 2 partially overlapping, possible N-linked glycosylation sites (NX[S/T]X) (N644 and N647) in the Drosophila α₁ subunit located in a region of the protein predicted to be external to the plasma membrane. (X generally is any amino acid, but in this site only X refers to any amino acid except P.) These asparagines fall in the loop between IS1 and IS2 which is predicted to be extracellular (see FIGS. 1 and 2). There are 8 possible cAMP-dependent protein kinase phosphorylation sites ([R/K]XX[S/T]) lying in predicted cytoplasmic domains. Six are in the amino terminal region; one is in the region between II-S6 and III-S1, which, in skeletal-muscle L-type channels, has been implicated in excitation-contraction coupling processes (Tanabe et al., (1990), *Nature*, vol. 346, op. 567–569, which disclosure is hereby incorporated by reference); one is in the carboxy terminus in the cytoplasmic region corresponding to the calcium-binding EF hand. In addition, there are 21 possible protein kinase C phosphorylation sites ([S/T]X[R/K]). Twelve of these are in the amino terminus; 2 are in the region between IIS6 and IIIS1; and 7 are in the carboxy terminal tail. There are also 27 possible casein kinase phosphorylation sites [S/TIXX[D/E]): 12 in the amino terminus, 1 each in the loops IS6/IIS1 and IIIS6/IVS1, 4 in loop IIS6/IIIS1, 1 at the cytoplasmic end of IVS4, and 8 in the carboxy-terminal tail. The high concentration of potential phosphorylation sites within several regions (the amino terminus, the II/III cytoplasmic loop and the C terminal tail) suggests that they may play roles in channel modulation by phosphorylation.

Example XI

Comparison of Sequences in Region of the Proposed Phenylalkylamine-Binding Domain The phenylalkylamines constitute an important class of organic calcium channel blockers. A proposed binding site for phenylalkylamines has been localized to a 42 residue segment extending from E1349 to W1391 in the rabbit skeletal muscle subunit (Striessnig et al., (1990), *Proc. Natl. Acad. Sci. USA*, vol. 87, pp. 9108–9112, which disclosure is hereby incorporated by reference). This region (shown by hatched underline in FIG. 7) includes transmembrane domain IVS6 and adjacent intracellular and extracellular segments. Since phenylalkylamines exert their blocking effects from the inner surface of the membrane (Hescheler et al., (1982), *Pflügers Arch.*, vol. 393, pp. 287–291; Affolter, J. and Coronado, R., (1986), *Biophys. J.*, vol. 49, pp. 767–771, which disclosures are hereby incorporated by reference), the binding site for this class of blockers is thought to include the intracellular side of transmembrane segment IVS6 and the adjacent intracellular amino acids (Striessnig et al., (1990), *Proc. Natl. Acad. Sci. USA*, vol. 97, pp. 9108–9112, which disclosure is hereby incorporated by reference). In FIG. 7, starting with the intracellular amino acids (right end of the hatched underline) and proceeding to the left into the transmembrane region IVS6, it is apparent that this segment is completely conserved between Drosophila (upper line) and rabbit skeletal muscle (lower line) until about halfway through the transmembrane region where there is a weakly conserved change from alanine (A) in the rabbit to serine (S) in Drosophila and a highly conserved change from methionine (M) to valine (V). This high degree of conservation predicts that this Drosophila subunit should bind phenylalkylamines with high affinity.

Example XII

Sequence Comparisons Relevant to Dihydropyridine Sensitivity

Among the calcium channel α₁ subunits listed in Table 2, the Drosophila subunit is most similar in sequence to those isoforms which have been shown to be dihydropyridine ("DHP") sensitive (indicated by+in this table). The four isoforms which are known to be insensitive to dihydropyridines (rat brain A and B, rabbit brain-1, and human N-type) show the least similarity to the Drosophila sequence. Another correlation is seen if the length of the cytoplasmic loop between repeats 11 and IIl is considered since all the known dihydropyridine-sensitive subunits have a short loop (134 to 150 amino acids in length) whereas the insensitive subunits have a much longer loop, ranging in length from 479 to 539. By this criterion, the Drosophila sequence would also fall into the DHP-sensitive category with a loop length of 129 amino acids.

A model for dihydropyridine-binding sites has been developed using photoaffinity labeling with dihydropyridines and has implicated the extracellular sides of transmembrane segments IIIS6 and IVS6 and the extracellular amino acids immediately adjacent to these transmembrane regions (Nakayama et al, (1991), *Proc. Natl. Acad. Sci. USA*, vol. 88, 9203–9207; Striessnig et al., (1991), *Proc. Natl. Acad. Sci. USA*, vol. 88, pp. 10769–10773; Catterall, W. A. and Striessnig, J., (1992), *TIPS*, vol. 13, pp. 256–262, which disclosures are hereby incorporated by reference). The segments involved are shown by the black underline in FIG. 7. In the portions of those two segments which include the left end (extracellular surface) of both S6 segments and the regions which extend to the left from the shaded transmembrane region, there are many amino acid differences (filled triangles above point to the changes) including: 8 nonconserved amino acid substitutions in the region adjacent to IIIS6 and extending into the extracelluar side of S6. In region IVS6 and the adjacent extracellular amino acids, there are three nonconserved substitutions and two deletions (involving one and two amino acids) in the Drosophila sequence compared with the rabbit. The functional significance of these changes can be addressed by expression of these new subunits.

RESULTS

1. Invertebrate voltage-dependent calcium channels belong to the same multigene family as those in mammals:

It was clear that Drosophila had calcium channels in both neurons and muscles, but the pharmacological specificity of these channels was apparently different from that described for the vertebrate L-type channel from skeletal muscle (Pauron et al., (1987), *Biochemistry*, vol. 26, pp. 6311–6315; Greenberg et al., (1989) *Insect Biochem.*, vol. 19, pp. 309–322; Peizer et al., (1989) *EMBO J.*, vol. 8, pp. 2365–2371; Glossman et al., (1991), *Br. J. Pharmacol.*, vol. 102, pp. 446–452, which disclosures are hereby incorporated by reference) since the predominant channel in Drosophila heads was phenylalkylamine sensitive and dihydropyridine insensitive. In addition, other pharmacological differences were apparent in side-by-side comparisons of guinea pig skeletal muscle with Drosophila head extracts (Glossman et al., (1991), *Br. J. Pharmacol.*, vol. 102, pp. 446–452, which disclosure is hereby incorporated by reference). Using PCR with degenerate primers, we were able to rapidly cross species to isolate the first invertebrate calcium channel α₁ subunit using information from vertebrate homologs. Our results indicate that despite pharmacological differences across species, insect calcium channel α₁ subunits belong to the same multigene family as mammalian α₁ subunits. The subunit described here shows the same 4 repeat structure, each containing 6 transmembrane segments, that is the characteristic pattern for voltage-dependent calcium channels. This Drosophila sequence highlights regions of $\alpha_1$ subunits which have been conserved across large evolutionary distances and therefore will facilitate the design of primer pairs for cloning homologous subunits from other invertebrate preparations of physiological importance or for cloning this subunit from pest insects.

2. Analysis Of Dmca ID Suggests Heterogeneity Of Neuronal $\alpha_1$ Subunits:

In the tissues tested, the size of the mRNA on Northern blots is larger (9.5, 10.2, or 12.5 kb) than the cDNA sequence-which we report here (8.0 kb). One possible explanation for this difference is that some untranslated regions are missing from the 5' and 3' ends. Indeed, we have not found a polyadenylation site on the 3' end. The finding of multiple in-frame stop codons in both the 5' and 3' untranslated regions provides strong evidence that the sequence presented here contains the full length open reading frame. The predominant forms seen on the Northern blot (FIG. 4) may represent major differences due to alternative splicing. Preliminary comparisons between genomic and cDNA using PCR have demonstrated the presence of at least 22 introns ranging in size from 55 base pairs to 3 kb (D. F. Eberl and D. Ren, unpublished observations, which are hereby incorporated by reference). We demonstrate here that alternative splicing occurs in at least two of these intron regions, but there are still many additional regions to be characterized. Depending on how the alternative splicing is done, it is possible to generate a large variety of mRNAs which will encode subunit forms with potentially different properties. Preliminary results suggest that this calcium channel subunit will show much heterogeneity due to alternative splicing. Indeed, the Drosophila sodium channel $\alpha$ subunit has the potential to express more than 48 different splice variants and at least 19 of which have been identified to date (J. R. Thackery and B. Ganetzky, 1994, *J. Neurosci.*, 14:2569–2578, personal communication, which is hereby incorporated by reference).

In view of the wide variety of potential alternative splice forms, it should be emphasized that the cDNA sequence shown in FIG. 2 represents the synthetic fusion of sequence information from two cDNA clones joined in a region of overlap within repeat III. Because of the large size of the full length message, it has not been possible to isolate a single cDNA clone that contains a complete open reading frame. One challenge of future work on this calcium channel subunit will be to identify physiologically relevant forms and define functional differences resulting from alternative splicing.

Using the Dmca1D cDNA as a probe in Northern blot analysis, there is more $\alpha_1$ subunit heterogeneity in heads than in bodies and legs since a prominent band at 10.2 kb is seen in heads and is not detected in bodies and legs. Only the 9.5 kb band is seen in all preparations. The heads would be enriched for nervous system compared to bodies and legs so the heterogeneity which we see in size of mRNA from heads could, in part, be due to functional diversity of channels expressed in neurons. This is interesting because it mirrors the greater heterogeneity observed by Leung, H. T. and Byerly, L., (1991), *J. Neurosci.*, vol. 11, pp. 3047–3059, which is hereby incorporated by reference, in the physiological properties of neuronal compared to muscle calcium channels in primary cultures of neurons and muscle from Drosophila embryos.

Indeed, there could be much more heterogeneity than reflected by our Northern analysis with respect to the Dmca1D gene since alternatively spliced messages close in size would not be readily distinguished by Northern blot analysis of a message of this large size. PCR analysis of cDNA using strategically placed primers is a more sensitive approach. In the preliminary PCR experiment summarized in Table 1 we again see more heterogeneity in heads than in bodies and legs. Peizer et al., (1989), *EMBO J.*, vol. 8, 2365–2371, which disclosure is hereby incorporated by reference, found 8 different conductance levels for calcium channels when Drosophila head membranes were reconstituted into lipid bilayers. These conductances were found in single channel activity records and did not interconvert suggesting that each activity results from a different type of channel molecule. It is possible that these functionally distinct, nonconverting channel subtypes reflect, in part, the alternative splicing which we observe in Dmca1D expressed in Drosophila head mRNA. Functional expression of different splice variants of this cloned calcium channel subunit will allow us to define the molecular basis of these biophysically and pharmacologically distinct channel subtypes.

3. Using Genetics To Define Subunit Properties In The Organism:

One of the primary motivating factors in extending calcium channel molecular biology studies to Drosophila is the ability to use genetics to inactivate subunit genes singly and in combination in order to define functional roles within the organism. The chromosome mapping studies described here show that the newly cloned Dmca1D gene falls within a well-studied region of the Drosophila genome (see Ashburner et al., (1990), *Genetics*, vol. 126, pp. 679–694, which adisclosure is hereby incorporated by reference). This region includes several lethal mutations. Recently, we have demonstrated that one of these embryonic lethal mutations causes a premature stop codon within the open reading frame of the Dmca1D gene (D. F. Eberl, D. Ren, G. Feng, L. J. Lorenz, D. Van Vactor, and L. M. Hall (1998) *Genetics* 148:1159–1169, hereby incorporated by reference). Genetic analysis of double mutants from this and other calcium channel subunits will allow us to define which subunits actually interact in vivo. Transformation rescue experiments (Spradling, A. C., (1986), In: *Drosophila: A Practical Approach*, Roberts, D. B., ed., IRL Press, Washington, D.C., pp. 175–197, which disclosure is hereby incorporated by reference) using this $\alpha_1$ subunit will allow us to test whether there is functional overlap among the different genes encoding homologous subunits and to determine the role in vivo of the different splice variants of this gene.

Example XIII $Ca^{2+}$ Channel $\alpha_1$ Subunit Mutation in Drosophila—A Late Embryonic Lethal In this example we describe the identification of the first mutations in Drosophila to affect an $\alpha_1$ subunit.

PCR procedure.

PCR was done in 100 $\mu$l volumes with three different polymerases: (1 & 4) (AmpliTaq (Perkin Elmer); (2) Pfu (Stratagene); (3) HotTub (Amersham) and with 0.1 $\mu$M of each primer (M1314A1B) (coordinates 3680–3701, ref. 18) and SP6SH18A1a (coordinates 4662–4684, ref. 18), which were tagged at the 5' end with either M13 or Sp6 sequence as indicated. Thermal cycling conditions were: 35 cycles of 1 min at 95° C., 1 min at 50° C., and 90 s at 72° C., followed by 10 min at 72° C., and cooling to 4° C. The PCR products were extracted from a 1% agarose gel with GeneClean glass powder (Bio101, CA), digested with Taql (BRL) for 1 hr at 65° C. and analyzed on 2.5% agarose gel. Fragments smaller than 120 bp are not visible in this gel.

Chromosome mapping of DmCa1D.

To determine the consequences of genetically inactivating this $\alpha_1$ subunit, we used the approach diagrammed in FIG.

8A to determine whether any existing mutants corresponded to DmCa1D. We first used in situ hybridization with biotinylated probes from DmCa1D to determine the approximate map position (35E3-F3), on the left arm of chromosome 2. Next deletions and chromosome aberrations were used to refine the cytogenetic map. Mutations which map to the same general area were ordered with respect to the same chromosome aberrations (Ashburner et al. (1990), *Genetics* 126:679). As summarized in FIG. 8B, this analysis revealed only 1 complementation group, 1(2)35Fa which showed the same mapping pattern as the clone DmCa1D. Strong mutations in this complementation group cause lethality at a late embryonic stage, while weak alleles allow some adult escapers which enclose with down turned wings. Lethal embryos appear to move within the egg, but do not hatch. Calcium channels are known to be present in Drosophila embryos (Leung et al. (1991), *J. Neurosci.* 11, 3047). Furthermore, developmental Northern analysis of DmCa1D has shown that there is a peak of mRNA synthesis in mid to late embryos. These observations are consistent with an embryonic lethal phenotype for mutations in an $\alpha_1$ subunit, thus 1(2)35Fa is a good candidate for the DmCa1D structural gene.

Rescue of 1(2)35Fa with a cosmid carrying DmCa1D.

To determine whether the 1(2)35Fa gene encodes DmCa1D, we used P-element-mediated transformation (Spradling, in Drosophila: A Practical Approach. D. B. Roberts, Ed. (IRL Press, Oxford, 1986) pp.175–197) to test whether a cosmid carrying this gene would cure the lethal phenotype. We isolated three cosmids from a genomic library using the following method: The PB1 and PB2 probes used for library screening (FIG. 9A) were labeled with $^{32}$pdCTP using the Megaprime random primer labeling kit (Amersham) and used to screen ~16,800 colonies of the iso-1 Drosophila genomic cosmid library (provided by John Tamkun, University of California at Santa Cruz). The PB1 probe is a 712 bp PCR fragment from the 3' end of DmCa1D (coordinates 5406–6118). The PB2 probe is a 664 bp PCR fragment that spans the first putative translation start site (coordinates –519 to +145). Prehybridization conditions were: overnight at 65° C. in 0.1×SSC, 50 mM sodium phosphate buffer pH 6.8, 5×Denhardt's, 0.25% sodium dodecyl sulfate (SDS), and 0.01% denatured salmon sperm DNA. Hybridization conditions were: overnight at 65° C. in the above buffer containing $10^6$ cpm/ml labeled probe. Washes were: twice for 15 min each in 2×SSC, 0.1% SDS at room temperature and twice for 30 min each in 0.1×SSC, 0.1% SDS at 65° C.

Figure 9A:
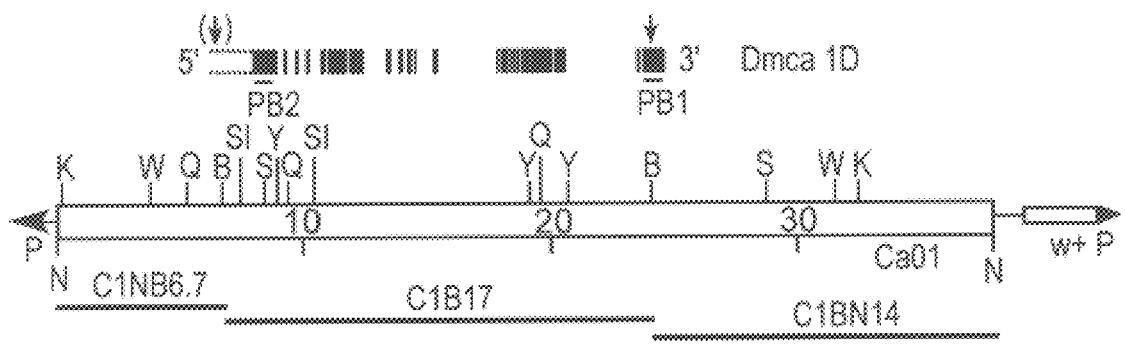

One of the cosmids isolated using this method (Ca01) was used for rescue. Ca01carries the entire DmCa1D coding region (~17 kb of genomic DNA) plus ~28 kb of the 5' upstream region (FIG. 9A). Ca01 was injected into embryos from a strain (y w; Sb P[Δ2-3]/TM6) that endogenously express the P-element transposase. To test whether Ca01 can rescue 1(2)35Fa mutations, flies carrying the transforming cosmid P[Ca01.88, w$^+$] in a mutant background [w; Df(2L) RA5α(2)35Fa; P[Ca01.88. w$^+$]/+] were constructed (Table 4). Df(2L)RA5 deletes a region that includes the 1(2)35Fa gene. Thus, these flies will live only if the Ca01.88 insert rescues 1(2)35Fa. Such rescued flies should have straight wings (Cy$^+$) and red eyes (w$^+$). Two transformed lines were tested and shown to fully rescue the lethality caused by each of the three mutant alleles of 1(2)35Fa since we recovered w$^+$Cy+ flies in the expected frequencies (Table 4). This means that the transcript that rescues 1(2)35Fa is encoded within the Ca01 cosmid. To determine whether the rescuing transcript is DmCa1D, we determined the number of embryonic transcripts encoded on Ca01, and we looked for sequence changes caused by the 1(2)35Fa mutants.

A single embryonic transcript encoded by Ca01.

Figure 9B:
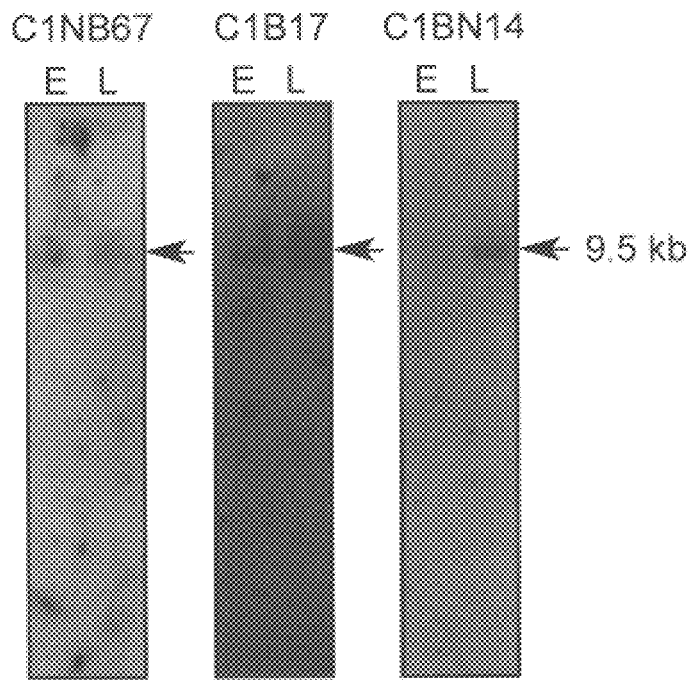

To determine how many candidate embryonic transcripts were encoded by the Ca01 cosmid clone, three subclones (C1NBG.7, C1B17, and C1BN14) shown in FIG. 9A were used to probe replicate embryonic Northern blots. Only one message (10.5 kb, the size expected for DmCa1D) was seen with any of the probes (FIG. 9B). The relative intensity of the signal on each blot is consistent with the relative proportion of the DmCa1D message encoded within that fragment. Thus the DmCa1D message is the only one transcribed from the Ca01 region, providing further evidence that DmCa1D corresponds to the 1(2)35Fa complementation group.

Stop codon produced by the 1(2)35Fa$^{X10}$ mutation.

To determine whether the 1(2)35Fa alleles alter the DmCa1D sequence, we used heteroduplex analysis on MDE gels (AT Biochem) which can identify single base substitutions in heterozygous DNA. This method is necessary since the mutations were induced with ethyl methanesulfonate which usually causes single base substitutions. In addition, heterozygote DNA must be tested because the homozygous mutations are lethal. Finally, the length of the genomic sequence encoding DmCa1D would make sequencing the complete genes from several mutants very labor intensive. Heteroduplex analysis is most efficient in small fragments (200–600 bp).

To minimize the number of PCR reactions required to analyze the genomic DNA containing the ORF (>17 kb), we amplified larger fragments (0.7–2 kb) and used frequently cutting restriction enzymes to create fragments of optimal size in a single gel lane. Use of several enzymes provided multiple opportunities to detect a sequence change.

MDE analysis of 5.6 kb of the coding region of the genomic sequence revealed an alteration in one allele, 1(2)35Fa$^{X10}$, that suggested a TaqI site had been destroyed (data not shown). This was confirmed by amplifying a smaller fragment containing the site in question and analyzing the fragments from a TaqI digestion (FIG. 10). The loss of a TaqI site is visualized by the appearance of a new, larger fragment (848 bp) only in the 1(2)35Fa$^{X10}$ heterozygotes (FIG. 10, lanes 1–3) and not with wild-type (FIG. 10, lane 4) and not with the other alleles (data now shown). Therefore, the X10 allele of 1(2)35Fa eliminates this TaqI site.

To determine whether the 1(2)35Fa$^{X10}$ alteration could be due to a PCR amplification artifact in which a base substitution occurred in an early round of replication, we repeated the amplification with three different polymerases, AmpliTaq, Pfu and Hot Tub (FIG. 10, lanes 1, 2, 3, respectively). TaqI digests the PCR products from heterozygous mutant (1(2)35Fa$^{X10}$/+) genomic DNA amplified with different polymerases all shown an extra 849 bp band compared with the wild-type chromosome alone.

The 1(2)35Fa gene: structural gene for a $Ca^{2+}$ $\alpha_1$ subunit.

To identify the alteration caused by the X10 allele, we sequenced the normal and mutant forms of this genomic region. Sequencing showed that the wild-type TaqI site TCGA (FIG. 10) is mutated to TTGA (FIG. 10) in the X10 allele, thereby changing an arginine CGA codon (RI307) to the TGA stop codon. The position of this change within the deduced DmCa1D protein is in the cytoplasmic loop just following the IV-S4 transmembrane region (FIG. 10). Introduction of a stop codon at this position would produce a truncated protein missing the last two transmembrane domains (IV-S5 and -S6) as well as the complete cytoplasmic carboxy tail. This tail contains both an EF hand motif, thought to bind $Ca^{2+}$, and the phenylalkylamine binding domain. Loss of these regions would likely result in a nonfunctional channel.

Taken together, the rescue of 1(2)35Fa with cosmid Ca01 which includes the entire coding domain for the calcium channel $\alpha_1$ subunit, the demonstration that the transcripts for the $\alpha_1$ subunit are the only ones detectable in embryos by Ca01 probes, and the identification of the Arg to stop codon produced within the $\alpha_1$ subunit coding region by the X10 allele constitute strong evidence for the conclusion that the 1(2)35Fa complementation group is the structural gene for the $Ca^{2+}$, channel $\alpha_1$ subunit cDNA, DmCa1D. Furthermore, the embryonic lethality of 1(2)35Fa is consistent with lethality observed when flies are fed the $Ca^{2+}$ channel blocker verapamil and with the peak of $\alpha_1$ subunit mRNA expression in mid to late embryos.

Role of the DmCa1D α1 subunit in the organism.

These studies demonstrate that DmCa1D is first required for survival in the developing embryo. It is not yet known whether the embryonic defect is simply physiological, preventing the proper hatching movements or whether is also affects developmental processes. The muscular dysgenesis (mdg) mutation in a mouse skeletal muscle $Ca^{2+}$ channel $\alpha_1$ subunit gene causes skeletal muscle paralysis. Our Drosophila work represents the first mutations described for neuronal calcium channels.

Gene cloning studies in a variety of species have shown that there are multiple genes encoding structurally similar α1 subunit. Drosophila is no exception to this observation because there are at least two distinct genes encoding $\alpha_1$ subunits: one on the second chromosome and one on the X chromosome. $\alpha_1$ subunits encoded by other genes are not functionally redundant with DmCa1D since mutations in the DmCa1D goes alone cause embryonic lethality even when the other $\alpha_1$ gene is normal.

Now that we can rescue 1(2)35Fa with a genomic clone, we are in a position to test the contribution of alternative splicing of DmCa1D to functional channel diversity using constructs with various spliced cDNA forms under control of the endogenous promoter in rescue experiments. Such analysis will define how much of the physiological heterogeneity observed in calcium channels in Drosophila embryonic cultures is due to alternative splicing and will begin to investigate functional redundancy of different splice variants.

Table 4. Rescue of 1(2)35Fa with the Ca01 cosmid. Two cosmid inserts, Ca01.88C4 and Ca01.88C7, were crossed into a strain carrying a deletion (Df(2L)RA5) of 1(2)35Fa. Crosses were made between the deletion heterozygote carrying the cosmid (w;Df (2L) RA5/CyO;P[Ca01.88, w$^+$]/+] and a strain heterozygous for a mutant allele [w;1(2)35Fa/CyO]. If Ca01 did not rescue 1(2)35Fa, there would be no straight-winged (Cy$^+$) offspring. Since w$^+$Cy$^+$ flies appear at half the frequency of each Cy class, there is complete rescue. Some mutant survivors (w Cy$^+$ flies) are allowed by the leaky allele 1(2)35Fa AR66 even in the absence of rescue by Ca01.

TABLE 4

| Cosmid insert | 1(2)3 5Fa allele | Cy | | Cy$^+$ | |
|---|---|---|---|---|---|
| | | w+ | w | w+ | w |
| Ca01.88C4 | X7 | 152 | 180 | 81 | 0 |
| | X10 | 121 | 145 | 57 | 0 |
| | AR66 | 150 | 180 | 81 | 16 |

TABLE 4-continued

| Cosmid insert | 1(2)3 5Fa allele | Cy | | Cy$^+$ | |
|---|---|---|---|---|---|
| | | w+ | w | w+ | w |
| Ca01.88C7 | X7 | 178 | 167 | 97 | 0 |
| | X10 | 262 | 251 | 139 | 0 |
| | AR66 | 198 | 214 | 86 | 9 |
| Ratio expected with complete rescue | | 2 | 2 | 1 | 0 |

FIG. 8. (A) displays identification of candidate genes for the cloned DmCaID cDNA. The left panel illustrates the method for localizing a recessive mutation relative to deletion breakpoints in deletion heterozygotes. If the mutation is within the breakpoint (upper diagram), then the wild type copy of the gene will be missing and the recessive mutant phenotype will be expressed. If the mutation is not within the deletion (lower diagram), then it will be "covered" by the wild-type (+) allele and will not be expressed. The right panel shows the corresponding cases for deletion mapping a cloned gene (indicated by arrow) by in situ hybridization to banded polytene chromosomes. (Note that the two homologous chromosomes are synapsed together along their lengths and the specific banding pattern identifies the chromosome region.) The upper diagram shows the cloned gene within the deletion while the lower panel illustrates a case where it is outside the deletion. Candidate mutations are those which show the same deletion mapping pattern as the cloned gene. (B) Genetic map of the calcium channel region. Genes (left column) have been separated and ordered by numerous deletions (right columns). The left and right deletion endpoints are indicated by the horizontal lines while the extent of the deletion is indicated by the vertical line. Vertical lines connected to only one horizontal line represent deletions whose other breakpoint extends beyond the limits of this figure. In situ hybridization with DmCa1D probes to polytene chromosomes of deletion heterozygotes showed that DmCa1D co-maps with a single complementation group, 1(2)35Fa (arrow).

FIG. 9(a) displays genomic cosmid (Ca01) used to rescue 1(2)35Fa. A drosophila genomic library was screened using probes (PB1 and PB2) derived from DmCa1D cDNA sequences. The Ca01 cosmid was used for P-element-mediated transformation rescue of 1(2)35Fa. Exons (black rectangles) in the DmCa1D cDNA clone are shown on the top line relative to the genomic sequences. The vertical lines above the first and last exon indicate the proposed positions of the start and end of the open reading frame. The dotted lines extending to the left of the 5' end of DmCa1D indicate the extension of the transcript beyond the existing cDNA clones as deduced from the faint signal in the blot probed with CINB 6.7. The positions of the red eye marker gene (w$^+$ and the flanking P-element ends (arrow heads) in the genomic clone are shown. Subclones of Ca01, designated CINB6.7, CIBI7 and CIBN14, used for probing Northerns are indicated. Restriction enzyme sites are abbreviated as follows: B=BamHI; K=Kpn I; N=Not I; Q=Xbal; S=Sal I; SI=SStl; W=Nhe I; Y=Spe I. (B) Embryonic Northern blot. Embryos were collected at 25° C. in two batches; early (E:3–12 hr) and late (L:13–21 hr). Poly(A)$^+$ mRNA was extracted from each batch, run on formaldehyde gels (20 μg/lane) and replicate Northern blots were prepared. The probes are indicated above each blot.

FIG. 10 displays detection of a sequence change in the DmCa1D calcium channel $\alpha_1$ subunit in the X10 allele of 1(2)35Fa. In FIG. 10(A) TaqI site is missing the X10 allele. Genomic DNA from mutant heterozygotes [1(2)Fa$^{X10}$/+] (lanes 1–3) or wild-type (lane 4) was amplified by PCR (33 using different polymerases (1 & 4 AmpliTaq; 2 Pfu; 3 HotTub) and cut with TaqI. The X7, X10 and AR66 alleles of 1(2)35Fa were induced on a common background chromosome, b pr cn wx bw. A fourth mutation induced on this background, AR146, mutates a nearby complementation group, 1(2)35F2. Because the b pr cn wx bw stock was unavailable, we used the 1(2)35Fd$^{AR146}$ chromosome, which should be unaltered in the 1(2)35Fa gene, to represent the "wild-type" background. Hemizygous DmCa1D region background DNA was obtained from 1(2)35Fd$^{Ar146}$/Df(2L) el18 flies, since Df(2L)el18 deletes the 1(2)35Fa region (FIG. 14B) but not the 1(2)35Fd region. A fourth allele, 1(2)35Fa$^{Ugia}$ was included in some analysis even though it was induced on a different background. The 848 bp fragment (lanes 1–3) found in the mutant DNA is missing a TaqI site which normally cuts this fragment into 530 and 318 bp pieces for the wild-type allele. FIG. 10(B) shows a premature stop codon in the X10 allele. To determine the molecular change in the mutant fragment missing the TaqI site (A, lanes 1–3), purified PCR products from the mutant heterozygote were digested with AccI and XbaI, ligated into pBlueScriptSK-II (Stratagene, Calif.) and used to transform the DH5 strain of Escherichia coli. Colonies with different TaqI restriction digestion patterns were sequenced using double stranded DNA cycle sequencing on an Applied Biosystems Sequencer Model 373A with the dideoxy chain termination method. In wild-type DNA the TaqI site is present but in the X10 mutant allele, the TaqI site is destroyed by a C to T transition resulting in the change of an arginine codon into a premature stop codon. FIG. 10(C) represents a schematic diagram of the $\alpha_1$ submit protein showing the location of the stop codon in the X10 mutation (small black box indicated by the arrow). The amino and carboxy terminal are thought to be cytoplasmic. There are 4 repeats (I, II, Ill, IV) each comprised of 6 transmembrane domains (S1-S6)(1).

EXAMPLE XIV

Time Course of Drosophila Calcium Channel Expression in Xenopus Oocytes as a Function of Injected cRNA Concentration We completed an analysis of 14 different chimeras to identify the region which was preventing expression of the Drosophila Dmca1D calcium channel currents in Xenopus oocytes. As a result of that analysis we defined a short region of 67 amino acids in the cytoplasmic loop between repeats II and III that was causing the difficulty (see FIG. 11). When an 85 amino acid segment from the rabbit cardiac $\alpha$1 C subunit was substituted in place of this 67 amino acid Drosophila sequence, we were able to reproducibly generate small calcium channel currents using barium as the charge carrier. A cartoon of the chimera showing the distribution of the fly and rabbit sequences is shown in FIG. 11. In this Example, and in the experiments described in the Examples below, we used a combination of subunit cRNAs. FIG. 12 shows the subunits used for studies of the insect channel. When control experiments were run using rabbit cardiac calcium channels, the same auxiliary subunits were used and the rabbit $\alpha$1C$\Delta$N60 subunit was used in place of the Drosophila L23RDD2 $\alpha$1 chimera.

As a first step in characterizing the L23RDD2 $\alpha$1 subunit, we determined the effect of calcium channel subunit cRNA concentration on peak current expression as a function of time after injection of Xenopus oocytes. These studies were based on our concurrent work with insect sodium channels in which we found that diluting the cRNA prior to injection often results in higher current levels than undiluted cRNA, presumably because of some inhibitory factor present in the cRNA preparation.

As summarized in FIG. 13, the peak currents were measured between 2 and 8 days after oocyte injection with different cRNA dilutions (from undiluted to a 1/20 dilution). The undiluted cRNA was a mixture containing the following cRNAs at concentrations given in ng/$\mu$l:300 L23RDD2 $\alpha$l, 150 $\alpha$2-$\delta$, and 83 $\beta$, The $\alpha$2-$\delta$ was from rabbit skeletal muscle while the $\beta$ was the Drosophila beta subunit isoform $\beta$-DN2C1. The recordings were done in Solution 2 without BAPTA preinjection. (See the Materials and Methods section below for experimental details.)

As shown in FIG. 13, the currents increase during the first five days after injection and then level to a plateau on days 6 through 8. There was no significant difference in total current or kinetics of current development in the undiluted versus the 0.5 dilution of cRNAs. As shown in FIG. 14, in the dilution range of 0.05 to 0.2, the amount of CRNA injected is linearly proportional to the peak current on days 2 through 8 after injection. At higher concentrations the peak currents are less than predicted by a linear relationship. This suggests that there is an inhibiting factor in the cRNA preparation. To conserve cRNA, a dilution of 0.5 was chosen for routine use and currents are routinely measured when they reach the 0.5 to 1.5 $\mu$A level. In general, recordings are best done within 3 to 6 days after injection to insure healthy oocytes with small leak currents.

MATERIALS AND METHODS

Clones

Construct L23RDD2 in the pAGA2 vector (Wei et al. (1991) *J. Biol. Chem.* 266:21943–21947) encodes the Drosophila Dmca1D calcium channel $\alpha$1 subunit. The coding sequence begins with the fifth methionine in the published sequence (Zheng et al. (1995) *J. Neurosci.* 15:1132–1143). A part of the II-III cytoplasmic loop (amino acids 1222–1228 in Zheng et al. (1995) *J. Neurosci.* 15:1132–1143) has been replaced with 85 amino acids from the rabbit cardiac $\alpha$1C subunit (amino acids 790–874, Wei et al. 1991, supra ). The $\alpha$2-$\delta$ subunit used in these studies is MXT$\alpha$2-$\delta$. This is an EcoRI fragment from the rabbit skeletal muscle $\alpha$2-$\delta$ subunit described by Mikami et al. ((1989) *Nature*340:230–233) subcloned into the Xenopus oocyte expression vector pBScMXT (from L. Salkoff, Washington, St Louis). The Drosophila beta subunit clone used was $\beta$-DN2CI in oocyte expression vector pAGA2. This beta subunit isoform contains both conserved domains and the N2 form of form of the amino terminus. The rabbit cardiac $\alpha$1C subunit clone (Wei et al. 1991, supra) (in the pAGA2 vector) was Card$\Delta$N60 in which the first 60 amino acids on the N terminus were deleted to enhance expression.

Oocyte Injections

Injection mixtures were prepared in 1 mM Tris pH7.0 and 50 nl was injected into each oocyte. For studies of the Drosophila L23RDD2 channel $\alpha$l subunit the concentrations of the "undiluted" cocktail in ng/ul were: 300 $\alpha$l, 150 $\alpha$2-$\delta$, 83 $\beta$. For studies of the rabbit cardiac $\alpha$l subunit the concentrations of the "undiluted" cocktail in ng/$\mu$l were: 12 $\alpha$1, 6.6 $\alpha$2-$\delta$, 3.6 $\beta$. Oocytes were incubated at 18° C. in ND96 plus supplements (Goldin (1992) *Methods Enz.* 207:266–279) (changed daily) until recording.

Recording conditions

Two different recording solutions were used. Solution 1 consisted of (in mM): 40 Ba(OH)$_2$, 50 NaOH, 2 KOH, 1 niflumic acid, 0.1 EGTA, 5 HEPES, adjusted to pH 7.4 with methanesulfonic acid (Pragnell et al. (1994) *Nature* 368:67–70). Solution 2 was used for some experiments and consisted of (in mM): 40 Ba(OH)$_2$, 52 TEA, 5 HEPES, adjusted to pH 7.4 with methanesulfonic acid (Yang et al. (1993) *Nature* 366:158–161). In some experiments as indicated, 5 to 15 minutes prior to recording the oocyte was injected with 50 nl of 100 mM BAPTA (adjusted to pH 7 with methanesulfonic acid). BAPTA chelates calcium and helps to prevent calcium-dependent run-down of the currents during the recordings. In some experiments the oocytes were perfused at a rate of ≈1.67 ml per min.

After the initial penetration of the oocyte, the oocyte was held at −80 mV and given a 100 ms pulse to +10 mV every-minute until the peak current stabilized (typically by 5 min). The general recording protocol consisted of a series of 100 ms pulses given at 10 sec intervals from −40 to +70 mV in 10 mV increments. The holding potential was −80 mV.

Nifedipine was prepared as a 10 mM solution in chloroform and stored as aliquots at −20° C. protected from light until use when it was diluted directly into recording solution. BayK8644 was prepared as a 50 mM stock solution in 100% methanol, stored as for nifedipine, and diluted directly into the recording solutions just prior to use. The perfusion solutions were protected from light during the course of the experiment.

EXAMPLE XV

Effect of Recording Solutions on the Peak Current for Calcium Channels Containing the Drosophila L23RDD2 α1 Subunit When we first began insect calcium channel expression in Xenopus oocytes, we were using a recording solution commonly used in the literature. This solution, designated Solution 1, consists of (in mM): 40 Ba(OH)$_2$, 50 NaOH, 2KOH, 1 niflumic acid, 0.1 EGTA, 5 HEPES, adjusted to pH 7.4 with methanesulfonic acid (Pragnell et al. (1994) *Nature* 368:67–70). Work of others (Polo-Parada and Korn (1997) *J. Gen. Physiol.* 109:693–702) had shown that external sodium partially blocks vertebrate calcium channels. Use of sodium-free solutions enhances currents of channels expressed in Xenopus oocytes. Solution 2, used for external sodium-free recordings, consisted of (in mM): 40 Ba(OH), 52 TEA, 5 HEPES, adjusted to pH 7.4 with methanesulfonic acid (Yana et al., 1993).

To determine whether insect calcium channel currents are enhanced in the absence of external sodium, peak currents were measured in an oocyte expressing the Drosophila L23RDD2 α1 along with rabbit α2-δ and Drosophila β. The oocyte was first perfused at ~1.67 ml/min for 12 min with Solution 2 and then perfused with Solution 1 for 8 min. As shown in the preliminary experiment in FIG. 15, the current rapidly decreased with the onset of perfusion of Solution 1(containing sodium). This decrease was partially reversed by the return of Solution 2 which contains no sodium. This observation is consistent with insect calcium channels showing the same partial sodium block as vertebrate calcium channels. Additional experiments are required to confirm this result and to systematically document the basis for the peak amplitude differences between the two solutions. However, based on these preliminary results, many of the experiments presented in this report were done in Solution 2 to enhance current levels.

EXAMPLE XVI

Effects of Coexpression of L23RDD2 α1 with α2-δ and β Subunits

For mammalian calcium channels it is well documented that expression of functional channels is stimulated by coexpression with α2-δ and β subunits (Singer et al. (1991) *Science* 253:1553–1557; Itagaki et al. (1992) FEBS Lett. 297:221–225; Williams et al. (1992) Neuron 8:71–84; Shistik et al. (1995) *J. Physiol.* (Lond) 489:55–62; Bangalore et al. (1996) Am. *J. Physiol.* 270:H1521–H1528; Wiser et al. (1996) *FEBS Lett.* 379:15–20). In addition, channel kinetics are also affected by the presence of these subunits. Since the object of our work is to define conditions for the most robust expression of the Drosophila α1 subunit, we next examined the effect of the auxiliary subunits on current expression in Xenopus oocytes using cRNA diluted 0.5. Recordings were done in Solution 2 following preinjection with BAPTA.

As shown by duplicate experiments (1 and 2) in FIG. 16, no detectable currents are produced by expression of the Drosophila α1 subunit alone. This can be seen even more clearly in FIG. 17, where the scale has been expanded to show the low current expressing oocytes. Coexpression of α1 with β shows some detectable current while coexpression of α1 with α2-δ shows little or no enhancement over the control endogenous current stimulation by α2-δ (FIG. 17). However, currents are dramatically enhanced by coexpression of α1 with both α2-δ and P. Although the α2-δ and β combination in the absence of the Drosophila α1 subunit stimulates the endogenous oocyte calcium channel currents, the endogenous peak currents are much lower (−121±6.8 nA in Experiment 1 and −292.0±21.2 nA in Experiment 2) than those recorded in the presence of the Drosophila α1 subunit (−1108.4+70.6 nA in Experiment 1 and −1112.3±63.1 nA in Experiment 2). Thus, for optimal expression of the Drosophila Dmca1D calcium channel, coexpression with both α2-δ and β is required. We are using a Drosophila β subunit, but a rabbit α2-δ subunit. This experiment provides evidence for the existence of an α2-δ homolog in Drosophila.

EXAMPLE XVII

Comparison of Calcium Versus Barium as the Charge Carrier: Effects On Peak Current and Channel Inactivation Peak current:

Many mammalian calcium channels show significantly higher currents when barium is used as the charge carrier instead of calcium (Bourinet et al. (1996) *J. Neurosci* 16:4983–4993.). As illustrated in FIG. 18 (bottom panel), the rabbit cardiac calcium channel is one such channel. The peak current in barium saline is 3722.5±214.9 nA while that in calcium saline is 2079.8±336.7 nA. This represents an ~1.8-fold increase in barium compared to calcium. In contrast, there is no statistically significant difference in peak current with the Drosophila channel (upper panel) in barium (850.4±136.5 nA) versus calcium (706.9±98.4 nA). This lack of current enhancement in barium saline suggests that this insect calcium channel may have a different ion selectivity than mammalian channels. These experiments were done in Solution 1 following preinjection with BAPTA. For the calcium saline, the barium in Solution 1 was replaced with equimolar calcium and EGTA was omitted.

Channel inactivation:

Another difference between insect and mammalian cardiac calcium channels is in the extent and conditions which induce channel inactivation. As seen in FIG. 18 (bottom panel), the rabbit cardiac channel does not show inactivation in barium containing Solution 1, but does show a calcium-dependent inactivation in calcium containing Solution 1. In contrast, the Drosophila channel (FIG. 18 upper panel) shows apparent inactivation in barium saline and this inactivation is faster in calcium saline.

As part of the biophysical characterization of the Drosophila channel, we have graphically compared the rate of inactivation in the two salines as a function of membrane potential and have superimposed these plots on the current voltage relationship (FIG. 19). This shows that the inactivation in calcium Solution 1 is maximum at voltages close to those eliciting maximum calcium influx. These studies suggest that the Drosophila calcium channel has the molecular determinants for calcium-induced inactivation, but the characteristics of Drosophila channel inactivation may differ from those observed with mammalian cardiac calcium channels (Zhou et al. (1997) *Proc. Natl. Acad. Sci. USA* 94:2301–2305).

EXAMPLE XVIII

Sensitivity of the L23RDD2-Containing Calcium Channels to the Dihydropyridine Antagonist, Nifedipine When we first cloned the Dmca1D Drosophila calcium channel α1 subunit, we proposed that it might correspond to the dihydropyridine-insensitive channel identified by ligand binding studies in Drosophila head membranes (Zheng et al. (1995) *J. Neurosci.* 15:1132–1143). Work with chimeras expressed in Xenopus oocytes and electrophysiological studies on the larval muscle preparation suggested that the Dmca1D gene actually encoded a dihydropyridine-sensitive channel. Now that we have defined conditions for expression of the α1 subunit, we have begun pharmacological characterization of this subunit.

FIG. 20 summarizes a dose response curve for the dihydropyridine antagonist nifedipine using oocytes expressing CRNA (in ng/ul): 150 L23RDD2 α1, 75 α2-δ, and 41.5 β. Each point represents 3 to 9 oocytes recorded in Solution 1. The EC50 for nifedipine is ~3 μM. This compares well with the nifedipine sensitivity determined for this calcium channel in Drosophila larval muscle where 10 μM nifedipine blocks 80% of the current associated with the Dmca1D current (Gielow et al. (1995) *J. Neurosci.* 15:6085–6093). These experiments unambiguously demonstrate the sensitivity of this Drosophila calcium channel to dihydropyridine antagonists. They also demonstrate that, at least for this drug, the pharmacological sensitivity as defined by Xenopus oocyte expression is an accurate reflection of larval muscle sensitivity. Thus, the Xenopus oocyte expression system is ready for use in testing compounds active against this calcium channel in insects.

EXAMPLE XIX

Sensitivity of the L23RDD2-Containing Calcium Channels to the Dihydropyridine Agonist BayK8644

In continuing the pharmacological characterization of the Drosophila Dmca1D calcium channel, we next determined sensitivity to the dihydropyridine agonist BayK8644 tested in Solution 2. BAPTA injection preceded all recordings. FIG. 21 shows the same oocyte recorded first in the absence of BayK8644 and then perfused with 2 μM BayK8644. The upper traces show the rabbit cardiac calcium channel in the absence (left) and presence (right) of BayK. The peak current in the absence of BayK is 488.2 nA while that in the presence is 1673.7 nA. This mammalian calcium channel shows two typical effects of BayK: increase in the peak current and slowing of the tail currents. In contrast, the Drosophila channel (lower traces) shows no stimulation. Peak current in the absence of BayK (1548.5 nA) is actually a bit higher than in its presence (1208.1 nA). In addition, tail currents show no obvious change in kinetics in the presence of BayK, although in Drosophila, as in mammalian channels, the apparent magnitude of the tail current seems enhanced by BayK.

These studies document an interesting difference between this insect calcium channel and the vertebrate L-type channels which- are their closest relatives. Although the insect channel is sensitive to dihydropyridine antagonists, it is insensitive to dihydropyridine agonists. This documents the utility of the Xenopus oocyte expression system to rapidly define differences in pharmacological specificity between insect and vertebrate calcium channels. This work also provides information of fundamental significance for modeling the differences between agonist and antagonist binding sites for the dihydropyridine class of calcium channels.

EXAMPLE XX

Model for Residues Involved in Dihydropyridine Binding in Calcium Channels: Sensitivity Differences Between Insect and Mammalian Channels The similarity between the structures for the dihydropyridine agonist BayK8644 and the antagonist nifedipine are summarized in FIG. 22. The groups which differ are shown in red in the nifedipine structure. Because of the similarity in these structures, overlap in the binding sites for agonists and antagonists is expected. Studies on vertebrate $α_1$ subunits have shown the IIIS5, IIIS6, and IVS6 transmembrane domains participate in dihydropyridine interactions in L-type calcium channels (Grabner et al. (1996) *Neuron* 16:207–218). As summarized in FIG. 23, systematic site-directed mutagenesis of single amino acid-residues which differ between L-type and non L-type α1 subunits implicate many amino acid residues on one side of putative a helices of transmembrane domains IIIS5 and IVS6 as being involved in high affinity binding of dihydropyridine antagonists and/or agonists (Peterson et al. (1996) *J. Biol. Chem.* 271:5293–52969; Peterson et al. (1997) *J. Biol. Chem.* 272:18752–18758). FIG. 23 summarizes these vertebrate calcium channel mutagenesis studies and compares the sequences in the regions of interest in vertebrate channels with those in Drosophila channels. The sequences in the dihydropyridine (DHP)-insensitive channels are given in the group below the L-type DHP-sensitive group. Those residues which have been mutagenized are boxed. In general, those which do not affect dihydropyridine sensitivity when changed are boxed in blue while those which do affect sensitivity are boxed in red. Residues which differ between sensitive vertebrate channels and the Dmca1D subunit are circled. These circled residues are candidates for changes which may be responsible for the difference in dihydropyridine agonist sensitivity between Drosophila and vertebrate channels. Although most of the vertebrate experiments examined sensitivity to dihydropyridine antagonists, the * residues indicate changes which affect both agonist and antagonist sensitivity. It is interesting to note that when both Y and M in domain IVS6 (heavy red underline) were changed, agonist sensitivity was abolished. One of these (LM) is altered in Drosophila. Perhaps this change in combination with one of the other circled residue changes (such as the altered proline residue at the beginning of domain IVS6) may be responsible for the lack of agonist sensitivity for the Drosophila channel.

FIG. 24 shows the Drosophila Dmca1D sequences in domains IIIS6 and IVS6 with the model for dihydropyridine interactions deduced from the mutagenesis studies superimposed. The yellow triangles are a schematic representation of parts of the dihydropyridine molecule thought to interact with the channel amino acid side chains. Residues within red circles affect dihydropyridine sensitivity when mutated. Those residues in which the letter for the amino acid are in green represent those amino acids in Drosophila which differ from the vertebrate L-type channels and therefore may be involved in the lack of sensitivity to dihydropyridine agonist in the insect channel. These studies illustrate how pharmacological comparison between insect and vertebrate channels may help to elucidate the nature of the binding domain.

Although the invention has been described in detail for the purpose of illustration, it is understood that such detail is solely for that purpose, and variations can be made therein by those skilled in the art without departing from the spirit and scope of the invention which is described by the following claims.

What is claimed is:

1. A method of screening a chemical agent for effectiveness as a pesticide, said method comprising:

providing a cell comprising a heterologous DNA molecule encoding an invertebrate calcium channel $\alpha_1$ subunit, wherein said DNA molecule is expressed by said cell, thereby forming a functional calcium channel;

exposing said cell to said chemical agent; and evaluating said cell to determine the pesticidal activity, as indicated by altered channel function, of said chemical agent.

2. The method of claim 1, wherein said cell is evaluated by comparing the calcium channel current in the presence of said chemical agent to the calcium channel current in the absence of said agent.

3. A method according to claim 1, wherein said invertebrate is *Drosophila melanogaster*.

4. A method according to claim 1, wherein said DNA molecule encodes the amino acid sequence corresponding to SEQ. ID. NO. 2.

5. A method according to claim 1, wherein said DNA molecule has the nucleotide sequence corresponding to SEQ. ID. NO. 1.

6. A method according to claim 1, wherein said cell is a *Xenopus oocyte*.

7. An method according to claim 1, wherein said calcium channel subunit is neuronal.

8. A method of identifying chemical agents which specifically interact with, and bind to, the calcium channel on the surface of a mammalian cell, said method comprising:
   contacting a mammalian cell with one or more chemical agents, wherein said cell comprises a DNA molecule encoding an invertebrate calcium channel $\alpha_1$ subunit, and wherein said DNA molecule is expressed by said cell, thereby forming a functional calcium channel; and
   identifying those chemical agents which bind to the mammalian cell; thereby identifying chemical agents which specifically interact with, and bind to, the calcium channel.

9. The method of claim 8, wherein a chemical agent that specifically interacts with, and binds to, the calcium channel is identified by comparing the calcium channel current in the presence of said chemical agent to the calcium channel current in the absence of said agent.

10. A method of identifying chemical agents which specifically interact with, and bind to, the calcium channel on the surface of a mammalian cell, said method comprising:
    contacting a mammalian cell with one or more chemical agents, wherein said cell comprises a DNA molecule encoding an invertebrate calcium channel $\alpha_1$ subunit, and wherein said DNA molecule is expressed by said cell, thereby forming a functional calcium channel; and
    identifying those chemical agents which bind to the mammalian cell; thereby identifying chemical agents which specifically interact with, and bind to, the calcium channel,
wherein said invertebrate is *Drosophila melanogaster*.

11. A method of identifying chemical agents which specifically interact with, and bind to, the calcium channel on the surface of a mammalian cell, said method comprising:
    contacting a mammalian cell with one or more chemical agents, wherein said cell comprises a DNA molecule encoding an invertebrate calcium channel $\alpha_1$ subunit, and wherein said DNA molecule is expressed by said cell, thereby forming a functional calcium channel; and
    identifying those chemical agents which bind to the mammalian cell; thereby identifying chemical agents which specifically interact with, and bind to, the calcium channel,
wherein said DNA molecule encodes the amino acid sequence corresponding to SEQ. ID. NO. 2.

12. A method of identifying chemical agents which specifically interact with, and bind to, the calcium channel on the surface of a mammalian cell, said method comprising:
    contacting a mammalian cell with one or more chemical agents, wherein said cell comprises a DNA molecule encoding an invertebrate calcium channel $\alpha_1$ subunit, and wherein said DNA molecule is expressed by said cell, thereby forming a functional calcium channel; and
    identifying those chemical agents which bind to the mammalian cell; thereby identifying chemical agents which specifically interact with, and bind to, the calcium channel,
wherein said DNA molecule has the nucleotide sequence corresponding to SEQ. ID. NO. 1.

13. A method of identifying chemical agents which specifically interact with, and bind to, the calcium channel on the surface of a mammalian cell, said method comprising:
    contacting a mammalian cell with one or more chemical agents, wherein said cell comprises a DNA molecule encoding an invertebrate calcium channel $\alpha_1$ subunit, and wherein said DNA molecule is expressed by said cell, thereby forming a functional calcium channel; and
    identifying those chemical agents which bind to the mammalian cell; thereby identifying chemical agents which specifically interact with, and bind to, the calcium channel,
wherein said calcium channel subunit is neuronal.

14. A method of identifying chemical agents which specifically interact with, and bind to, the calcium channel on the surface of a mammalian cell, said method comprising:
    contacting a mammalian cell with one or more chemical agents, wherein said cell comprises a DNA molecule encoding an invertebrate calcium channel $\alpha_1$ subunit, and wherein said DNA molecule is expressed by said cell, thereby forming a functional calcium channel; and
    identifying those chemical agents which bind to the mammalian cell; thereby identifying chemical agents which specifically interact with, and bind to, the calcium channel,
wherein said chemical agents are organic calcium channel blocking agents.

* * * * *

SEQUENCE LISTING (1) GENERAL INFORMATION:

(iii) NUMBER OF SEQUENCES: 57

(2) INFORMATION FOR SEQ ID NO: 1:

(i) SEQUENCE CHARACTERISTICS:
        (A) LENGTH: 8075 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 157..7704

(xi) SEQUENCE DESCRIPTION: SEQ ID NO: 1:

```
GGTCATCATT GGCTCTCAGA GGATTCTCTG CTGCCAACAT AGCCGATGAA AACATAATGC       60

AACACAGAAT AATGTTGCCG AAATTGCTGT GATTGCAAAG CCTCGACCTC GACCTCAACC      120

TCGACCTCCG CCTCCACCAC CACCACGAAT ACTGTG ATG GGT GGC GGG GAG CTG       174
                                     Met Gly Gly Gly Glu Leu
                                       1               5

GTG AAC TGT ATA GCC TAC GAT GAC AAC ACC CTG GTC ATC GAG AGG AAA       222
Val Asn Cys Ile Ala Tyr Asp Asp Asn Thr Leu Val Ile Glu Arg Lys
         10                  15                  20

CCC TCG CCC TCC TCC CCG TCC ACC AGC CGG CGT TAT CTG AAG GCC GAA       270
Pro Ser Pro Ser Ser Pro Ser Thr Ser Arg Arg Tyr Leu Lys Ala Glu
             25                  30                  35

ACG CCG ACG CGT GGC AGT CGA AAG TAC AAC CGC AAG TCA TCG GCT AAA       318
Thr Pro Thr Arg Gly Ser Arg Lys Tyr Asn Arg Lys Ser Ser Ala Lys
 40                  45                  50

AGT GAT TTG GAA GTG GTC GTT GTC AAG CCG GAA CAC CAT CAT CAG CAT       366
Ser Asp Leu Glu Val Val Val Lys Pro Glu His His His Gln His
 55                  60                  65                  70

CGA TCT CCG ACG ATA ACG CTT CCG GTT CCG GCT AAC CCA CTA ACC ACA       414
Arg Ser Pro Thr Ile Thr Leu Pro Val Pro Ala Asn Pro Leu Thr Thr
                 75                  80                  85

TCG GCA TCG GCG GGA TCC TCG CCC ACG GGA GCG GGA TTG GCA GCC GGA       462
Ser Ala Ser Ala Gly Ser Ser Pro Thr Gly Ala Gly Leu Ala Ala Gly
             90                  95                 100

TTG GGA ACT GCC TCG GGA ACG GTC CTG CAA CAA AGC TGC AGT GCA CTT       510
Leu Gly Thr Ala Ser Gly Thr Val Leu Gln Gln Ser Cys Ser Ala Leu
            105                 110                 115

GAT CCG CCC GAG GAT TCG AAT CAG CCC AGC GGG ACC AGG AGG CGA GCC       558
Asp Pro Pro Glu Asp Ser Asn Gln Pro Ser Gly Thr Arg Arg Arg Ala
120                 125                 130

ACC AGC ACC GAG CTC GCC CTC AGC AAC GTC ACC AGT CAG ATT GTG AAC       606
Thr Ser Thr Glu Leu Ala Leu Ser Asn Val Thr Ser Gln Ile Val Asn
135                 140                 145                 150
```

-continued

```
AAT GCC ACC TAC AAG CTA GAC TTC AAG CAA CGT CGT CAC AAA AGC AAC        654
Asn Ala Thr Tyr Lys Leu Asp Phe Lys Gln Arg Arg His Lys Ser Asn
            155                 160                 165

AAC GGA GGC AGT GAG TCA GGA TCT CTA ACC GGA ATA GCC ACA GGA CCG        702
Asn Gly Gly Ser Glu Ser Gly Ser Leu Thr Gly Ile Ala Thr Gly Pro
170                 175                 180

GCG ACA AGT CCC GCA GGA CCA ACA GGA CCA ACC AGT TCC AGC GGC AAG        750
Ala Thr Ser Pro Ala Gly Pro Thr Gly Pro Thr Ser Ser Ser Gly Lys
            185                 190                 195

CGG CGC AAG TCC AGT TGC ACA TCC TGC GGC GGA GGT GGC ATC AGT GCC        798
Arg Arg Lys Ser Ser Cys Thr Ser Cys Gly Gly Gly Gly Ile Ser Ala
200                 205                 210

CCA CCC CCG AGA CTA ACG CCC GAG GAG GCG TGG CAA CTG CAA CCA CAG        846
Pro Pro Pro Arg Leu Thr Pro Glu Glu Ala Trp Gln Leu Gln Pro Gln
215                 220                 225                 230

AAC AGT GTT ACC AGT GCC GGC AGC ACA AAT AGT AGT TTC AGC AGC GGC        894
Asn Ser Val Thr Ser Ala Gly Ser Thr Asn Ser Ser Phe Ser Ser Gly
            235                 240                 245

GGC GGA CGC GAC GAT AAT AGT AGT TAC AGT GCC GTC GGC GGC GAT AGC        942
Gly Gly Arg Asp Asp Asn Ser Ser Tyr Ser Ala Val Gly Gly Asp Ser
            250                 255                 260

AGC AGC AGC AAT AGT TGC AAC TGC GAT ATC ACC GGT GAT AAC AGT ACA        990
Ser Ser Ser Asn Ser Cys Asn Cys Asp Ile Thr Gly Asp Asn Ser Thr
            265                 270                 275

TTG CAT GGT TTG GGC GTC GGC GAC GTT TGT AGT TTC ATC GCC GAT TGT       1038
Leu His Gly Leu Gly Val Gly Asp Val Cys Ser Phe Ile Ala Asp Cys
            280                 285                 290

GAC GAC AAT AGC GAG GAC GAC GAC GGC GAT CCG AAT AAC CAG GAT CTC       1086
Asp Asp Asn Ser Glu Asp Asp Asp Gly Asp Pro Asn Asn Gln Asp Leu
295                 300                 305                 310

AGC TCG CAA ACC CTG CGC ACA GCG GCC ATC GTA GCG GCA GTT GCG GCA       1134
Ser Ser Gln Thr Leu Arg Thr Ala Ala Ile Val Ala Ala Val Ala Ala
            315                 320                 325

GCA GCC AAG GAA CAG GCC CAG GAG CAA TCG CTC GCC GAC TGC GAG AGC       1182
Ala Ala Lys Glu Gln Ala Gln Glu Gln Ser Leu Ala Asp Cys Glu Ser
            330                 335                 340

TTC AGC GAT CGC CGG CAG GAT GCC GAT GAG GAC GTC CGC ATC ATT CAG       1230
Phe Ser Asp Arg Arg Gln Asp Ala Asp Glu Asp Val Arg Ile Ile Gln
            345                 350                 355

GAT TGC TGC GGC GGC AAC AAC GAC TCA CTC GAA GAC GTT GGC GAG GTG       1278
Asp Cys Cys Gly Gly Asn Asn Asp Ser Leu Glu Asp Val Gly Glu Val
360                 365                 370

GAC GAC AAC GCC GAC GTT GTC GTG AGA AAG AAC TCA AGG AAT CGT CCC       1326
Asp Asp Asn Ala Asp Val Val Val Arg Lys Asn Ser Arg Asn Arg Pro
375                 380                 385                 390

TCG ATC AGA AGG ACA TGC AGG ATA ACC GAG GAG GAC GAC GAC GAG GAC       1374
Ser Ile Arg Arg Thr Cys Arg Ile Thr Glu Glu Asp Asp Asp Glu Asp
            395                 400                 405

GAG AAC GCG GAC TAC GGT GAT TTC GAT CGG GAG GAT CAA GAG CTA GAC       1422
Glu Asn Ala Asp Tyr Gly Asp Phe Asp Arg Glu Asp Gln Glu Leu Asp
            410                 415                 420

GAC GAG GAG CCC GAG GGC ACC ACC ATT GAC ATT GAT GAG CAG GAA CAG       1470
Asp Glu Glu Pro Glu Gly Thr Thr Ile Asp Ile Asp Glu Gln Glu Gln
            425                 430                 435

CAG CAC GAC CAA GGT GAT TCC GCT GAA GAG GAA GAC CAC GAC GAG GAC       1518
Gln His Asp Gln Gly Asp Ser Ala Glu Glu Glu Asp His Asp Glu Asp
            440                 445                 450

GTC GAC GAG TAC TTT GAG GAG GAG GAG GAC GAC ACG CAG GCC TTT TCG       1566
Val Asp Glu Tyr Phe Glu Glu Glu Glu Asp Asp Thr Gln Ala Phe Ser
```

```
455                460                465                470
CCA TTC TAC TCC AGT TCC GCG GAG CTA ATT GAT AAT TTT GGT GGC GGT    1614
Pro Phe Tyr Ser Ser Ser Ala Glu Leu Ile Asp Asn Phe Gly Gly Gly
            475                480                485

GCG GGC AAG TTC TTC AAC ATA ATG GAC TTC GAG CGT GGA GCC TCC GGC    1662
Ala Gly Lys Phe Phe Asn Ile Met Asp Phe Glu Arg Gly Ala Ser Gly
            490                495                500

GAG GGA GGC TTT TCG CCA AAC GGC AAC GGT GGT CCC GGC AGC GGT GAT    1710
Glu Gly Gly Phe Ser Pro Asn Gly Asn Gly Gly Pro Gly Ser Gly Asp
            505                510                515

GTT TCC CGT ACG GCG AGA TAC GAC TCC GGG GAG GGG GAT CTG GGC GGC    1758
Val Ser Arg Thr Ala Arg Tyr Asp Ser Gly Glu Gly Asp Leu Gly Gly
            520                525                530

GGC AAC AAT ATC ATG GGC ATC GAT TCT ATG GGC ATT GCA AAC ATT CCG    1806
Gly Asn Asn Ile Met Gly Ile Asp Ser Met Gly Ile Ala Asn Ile Pro
535                540                545                550

GAA ACC ATG AAC GGC ACC ACA ATT GGA CCA AGT GGA GCC GGT GGC CAA    1854
Glu Thr Met Asn Gly Thr Thr Ile Gly Pro Ser Gly Ala Gly Gly Gln
            555                560                565

AAA GGT GGT GCT GCT GCA GGT GCC GCT GGC CAA AAG AGA CAA CAA CGC    1902
Lys Gly Gly Ala Ala Ala Gly Ala Ala Gly Gln Lys Arg Gln Gln Arg
            570                575                580

CGT GGA AAA CCG CAA CCA GAC AGA CCA CAA CGA GCA TTA TTT TGC CTG    1950
Arg Gly Lys Pro Gln Pro Asp Arg Pro Gln Arg Ala Leu Phe Cys Leu
            585                590                595

AGC GTC AAG AAT CCC CTG CGA GCC CTG TGC ATT CGC ATT GTG GAG TGG    1998
Ser Val Lys Asn Pro Leu Arg Ala Leu Cys Ile Arg Ile Val Glu Trp
            600                605                610

AAA CCA TTT GAG TTC CTT ATT TTG TTA ACC ATT TTT GCC AAC TGT ATT    2046
Lys Pro Phe Glu Phe Leu Ile Leu Leu Thr Ile Phe Ala Asn Cys Ile
615                620                625                630

GCC TTG GCG GTT TAC ACC CCT TAT CCG GGA AGC GAT TCA AAC GTG ACG    2094
Ala Leu Ala Val Tyr Thr Pro Tyr Pro Gly Ser Asp Ser Asn Val Thr
            635                640                645

AAT CAA ACC TTG GAA AAA GTT GAA TAT GTA TTC CTA GTT ATA TTC ACA    2142
Asn Gln Thr Leu Glu Lys Val Glu Tyr Val Phe Leu Val Ile Phe Thr
            650                655                660

GCG GAA TGT GTT ATG AAA ATT TTA GCA TAT GGT TTT GTG TTA CAT GAT    2190
Ala Glu Cys Val Met Lys Ile Leu Ala Tyr Gly Phe Val Leu His Asp
            665                670                675

GGT GCA TAT CTG GGA AAT GGA TGG AAT TTA TTA GAT TTT ACA ATT GTA    2238
Gly Ala Tyr Leu Gly Asn Gly Trp Asn Leu Leu Asp Phe Thr Ile Val
            680                685                690

GTT ATG GGG GCG ATA AGT ACT GCA CTC TCC CAA TTG ATG AAG GAC GCC    2286
Val Met Gly Ala Ile Ser Thr Ala Leu Ser Gln Leu Met Lys Asp Ala
695                700                705                710

TTT GAT GTG AAG GCT CTA CGT GCC TTT CGA GTG CTA CGT CCA CTG CGA    2334
Phe Asp Val Lys Ala Leu Arg Ala Phe Arg Val Leu Arg Pro Leu Arg
            715                720                725

CTT GTA TCG GGT GTA CCA AGT CTA CAG GTT GTG CTG AAT TCA ATT TTA    2382
Leu Val Ser Gly Val Pro Ser Leu Gln Val Val Leu Asn Ser Ile Leu
            730                735                740

AAG GCC ATG GTG CCA CTG TTT CAC ATT GCA CTC CTG GTC CTA TTC GTA    2430
Lys Ala Met Val Pro Leu Phe His Ile Ala Leu Leu Val Leu Phe Val
            745                750                755

ATC ATA ATC TAT GCG ATA ATT GGC CTA GAG CTC TTC TCT GGC AAA TTG    2478
Ile Ile Ile Tyr Ala Ile Ile Gly Leu Glu Leu Phe Ser Gly Lys Leu
            760                765                770

CAC AAG GCG TGT CGC GAT GAG ATC ACA GGT GAA TAC GAG GAA AAC ATC    2526
```

```
His Lys Ala Cys Arg Asp Glu Ile Thr Gly Glu Tyr Glu Glu Asn Ile
775                 780                 785                 790

CGG CCC TGC GGA GTG GGC TAC CAG TGT CCG CCG GGC TAC AAG TGC TAC       2574
Arg Pro Cys Gly Val Gly Tyr Gln Cys Pro Pro Gly Tyr Lys Cys Tyr
                795                 800                 805

GGC GGA TGG GAT GGA CCA AAC GAC GGC ATC ACC AAC TTC GAC AAC TTT       2622
Gly Gly Trp Asp Gly Pro Asn Asp Gly Ile Thr Asn Phe Asp Asn Phe
                810                 815                 820

GGC CTG GCC ATG TTG ACG GTG TTC CAG TGC GTC ACC CTT GAG GGC TGG       2670
Gly Leu Ala Met Leu Thr Val Phe Gln Cys Val Thr Leu Glu Gly Trp
                825                 830                 835

ACT GAT GTC CTT TAT AGC ATC CAA GAT GCA ATG GGC AGC GAT TGG CAG       2718
Thr Asp Val Leu Tyr Ser Ile Gln Asp Ala Met Gly Ser Asp Trp Gln
840                 845                 850

TGG ATG TAC TTC ATT TCC ATG GTT ATC CTG GGT GCC TTC TTC GTG ATG       2766
Trp Met Tyr Phe Ile Ser Met Val Ile Leu Gly Ala Phe Phe Val Met
855                 860                 865                 870

AAT CTG ATT CTC GGT GTG TTG TCC GGT GAG TTC TCC AAG GAG CGT AAC       2814
Asn Leu Ile Leu Gly Val Leu Ser Gly Glu Phe Ser Lys Glu Arg Asn
                875                 880                 885

AAG GCC AAA AAC CGC GGT GAC TTC CAG AAG CTG CGC GAG AAG CAG CAG       2862
Lys Ala Lys Asn Arg Gly Asp Phe Gln Lys Leu Arg Glu Lys Gln Gln
                890                 895                 900

ATC GAA GAG GAT CTG CGG GGC TAT CTC GAT TGG ATT ACC CAA GCC GAG       2910
Ile Glu Glu Asp Leu Arg Gly Tyr Leu Asp Trp Ile Thr Gln Ala Glu
                905                 910                 915

GAC ATT GAA CCA GAC GCC GTG GGA GGT CTG ATA TCC GAT GGC AAG GGC       2958
Asp Ile Glu Pro Asp Ala Val Gly Gly Leu Ile Ser Asp Gly Lys Gly
920                 925                 930

AAG CAG CCC AAC GAA ATG GAT TCC ACC GAG AAT CTG GGC GAA GAA ATG       3006
Lys Gln Pro Asn Glu Met Asp Ser Thr Glu Asn Leu Gly Glu Glu Met
935                 940                 945                 950

CCC GAG GTC CAA ATG ACT GAA TCA CGA TGG CGC AAA ATG AAG AAG GAC       3054
Pro Glu Val Gln Met Thr Glu Ser Arg Trp Arg Lys Met Lys Lys Asp
                955                 960                 965

TTC GAT CGA GTC AAT CGT CGA ATG CGA AGA GCC TGT CGC AAG GCA GTC       3102
Phe Asp Arg Val Asn Arg Arg Met Arg Arg Ala Cys Arg Lys Ala Val
                970                 975                 980

AAG TCG CAG GCC TTC TAT TGG CTC ATC ATC GTT TTG GTG TTT CTC AAT       3150
Lys Ser Gln Ala Phe Tyr Trp Leu Ile Ile Val Leu Val Phe Leu Asn
                985                 990                 995

ACG GGT GTC TTG GCC ACG GAG CAT TAT GGC CAA CTT GAT TGG CTA GAT       3198
Thr Gly Val Leu Ala Thr Glu His Tyr Gly Gln Leu Asp Trp Leu Asp
1000                1005                1010

AAC TTC CAG GAG TAC ACC AAC GTG TTC TTC ATC GGA CTG TTC ACC TGC       3246
Asn Phe Gln Glu Tyr Thr Asn Val Phe Phe Ile Gly Leu Phe Thr Cys
1015                1020                1025                1030

GAA ATG TTG TTG AAG ATG TAC AGC TTG GGC TTT CAG GGC TAC TTC GTT       3294
Glu Met Leu Leu Lys Met Tyr Ser Leu Gly Phe Gln Gly Tyr Phe Val
                1035                1040                1045

TCG CTG TTC AAT CGT TTT GAT TGT TTT GTG GTG ATT GGC AGC ATT ACG       3342
Ser Leu Phe Asn Arg Phe Asp Cys Phe Val Val Ile Gly Ser Ile Thr
                1050                1055                1060

GAA ACC CTG CTA ACA AAC ACG GGA ATG ATG CCG CCA TTG GGT GTC TCC       3390
Glu Thr Leu Leu Thr Asn Thr Gly Met Met Pro Pro Leu Gly Val Ser
                1065                1070                1075

GTG CTG CGT TGT GTA CGT CTC CTG AGA GTC TTT AAA GTA ACT AAG TAC       3438
Val Leu Arg Cys Val Arg Leu Leu Arg Val Phe Lys Val Thr Lys Tyr
1080                1085                1090
```

-continued

| | |
|---|---|
| TGG CGG TCT CTC TCA AAT CTC GTC GCT TCC CTA TTG AAC TCT ATA CAA<br>Trp Arg Ser Leu Ser Asn Leu Val Ala Ser Leu Leu Asn Ser Ile Gln<br>1095                1100                1105                1110 | 3486 |
| TCG ATT GCT TCA CTT TTG TTA CTG CTC TTC CTA TTT ATT GTG ATA TTT<br>Ser Ile Ala Ser Leu Leu Leu Leu Phe Leu Phe Ile Val Ile Phe<br>                1115                1120                1125 | 3534 |
| GCT TTG CTG GGC ATG CAA GTT TTT GGC GGT AAA TTT AAT TTT GAT GGC<br>Ala Leu Leu Gly Met Gln Val Phe Gly Gly Lys Phe Asn Phe Asp Gly<br>            1130                1135                1140 | 3582 |
| AAA GAG GAG AAG TAT CGA ATG AAC TTC GAC TGC TTC TGG CAG GCT CTA<br>Lys Glu Glu Lys Tyr Arg Met Asn Phe Asp Cys Phe Trp Gln Ala Leu<br>1145                1150                1155 | 3630 |
| CTC ACA GTG TTT CAG ATC ATG ACT GGC GAG GAT TGG AAT GCT GTG ATG<br>Leu Thr Val Phe Gln Ile Met Thr Gly Glu Asp Trp Asn Ala Val Met<br>            1160                1165                1170 | 3678 |
| TAT GTG GGC ATC AAT GCC TAT GGC GGT GTG TCC TCC TAT GGT GCC TTG<br>Tyr Val Gly Ile Asn Ala Tyr Gly Gly Val Ser Ser Tyr Gly Ala Leu<br>1175                1180                1185                1190 | 3726 |
| GCC TGT ATT TAC TTT ATT ATT TTG TTC ATA TGC GGT AAC TAC ATC CTG<br>Ala Cys Ile Tyr Phe Ile Ile Leu Phe Ile Cys Gly Asn Tyr Ile Leu<br>                1195                1200                1205 | 3774 |
| CTA AAC GTG TTC TTG GCC ATT GCT GTG GAT AAT TTG GCC GAT GCC GAC<br>Leu Asn Val Phe Leu Ala Ile Ala Val Asp Asn Leu Ala Asp Ala Asp<br>            1210                1215                1220 | 3822 |
| TCG CTC TCT GAG GTC GAA AAA GAA GAG GAA CCT CAC GAT GAA TCT GCT<br>Ser Leu Ser Glu Val Glu Lys Glu Glu Glu Pro His Asp Glu Ser Ala<br>                1225                1230                1235 | 3870 |
| CAG AAA AAG TCA CAT AGT CCG ACT CCA ACA ATT GAT GGC ATG GAT GAT<br>Gln Lys Lys Ser His Ser Pro Thr Pro Thr Ile Asp Gly Met Asp Asp<br>            1240                1245                1250 | 3918 |
| CAC CTC AGC ATA GAT ATC GAT ATG GAG CAA CAG GAA CTG GAT GAC GAA<br>His Leu Ser Ile Asp Ile Asp Met Glu Gln Gln Glu Leu Asp Asp Glu<br>1255                1260                1265                1270 | 3966 |
| GAC AAA ATG GAC CAT GAA ACA TTA TCA GAC GAG GAA GTT CGT GAA ATG<br>Asp Lys Met Asp His Glu Thr Leu Ser Asp Glu Glu Val Arg Glu Met<br>                1275                1280                1285 | 4014 |
| TGC GAG GAG GAA GAG GAA GTG GAT GAA GAA GGC ATG ATT ACA GCA CGA<br>Cys Glu Glu Glu Glu Glu Val Asp Glu Glu Gly Met Ile Thr Ala Arg<br>            1290                1295                1300 | 4062 |
| CCC CGA CGT ATG TCT GAG GTT AAT ACG GCA ACG AAA ATT CTA CCC ATA<br>Pro Arg Arg Met Ser Glu Val Asn Thr Ala Thr Lys Ile Leu Pro Ile<br>                1305                1310                1315 | 4110 |
| CCG CCG GGC ACA TCA TTT TTT CTT TTC TCA CAA ACG AAC AGA TTT CGC<br>Pro Pro Gly Thr Ser Phe Phe Leu Phe Ser Gln Thr Asn Arg Phe Arg<br>            1320                1325                1330 | 4158 |
| GTC TTC TGC CAC TGG CTT TGC AAT CAC AGC AAT TTC GGC AAC ATT ATT<br>Val Phe Cys His Trp Leu Cys Asn His Ser Asn Phe Gly Asn Ile Ile<br>1335                1340                1345                1350 | 4206 |
| CTG TGT TGC ATT ATG TTT TCA TCG GCT ATG TTG GCA GCA GAG AAT CCT<br>Leu Cys Cys Ile Met Phe Ser Ser Ala Met Leu Ala Ala Glu Asn Pro<br>                1355                1360                1365 | 4254 |
| CTG AGA GCC AAT GAT GAC CTG AAT AAA GTG CTC AAT AAA TTT GAT TAT<br>Leu Arg Ala Asn Asp Asp Leu Asn Lys Val Leu Asn Lys Phe Asp Tyr<br>            1370                1375                1380 | 4302 |
| TTT TTC ACG GCA GTT TTC ACA ATG GAA CTG ATT CTG AAA TTG ATT TCA<br>Phe Phe Thr Ala Val Phe Thr Met Glu Leu Ile Leu Lys Leu Ile Ser<br>                1385                1390                1395 | 4350 |
| TAC GGC TTC GTA TTA CAC GAC GGA GCC TTT TGC AGA TCC GCA TTT AAT<br>Tyr Gly Phe Val Leu His Asp Gly Ala Phe Cys Arg Ser Ala Phe Asn<br>            1400                1405                1410 | 4398 |

```
CTA TTA GAT TTA CTT GTG GTC TGC GTG TCA TTG ATT TCT CTA GTG TCC       4446
Leu Leu Asp Leu Leu Val Val Cys Val Ser Leu Ile Ser Leu Val Ser
1415                1420                1425                1430

AGT TCG GAT GCG ATT TCA GTC GTG AAA ATT CTA CGT GTG CTC CGT GTT       4494
Ser Ser Asp Ala Ile Ser Val Val Lys Ile Leu Arg Val Leu Arg Val
                    1435                1440                1445

TTA AGG CCA CTC AGA GCC ATT AAT CGT GCC AAG GGA CTG AAG CAT GTT       4542
Leu Arg Pro Leu Arg Ala Ile Asn Arg Ala Lys Gly Leu Lys His Val
                1450                1455                1460

GTT CAA TGT GTC ATA GTC GCT GTT AAG ACT ATC GGA AAT ATT GTG CTC       4590
Val Gln Cys Val Ile Val Ala Val Lys Thr Ile Gly Asn Ile Val Leu
            1465                1470                1475

GTC ACA TGC CTA CTG CAG TTC ATG TTT GCC GTA ATA GGA GTC CAA TTG       4638
Val Thr Cys Leu Leu Gln Phe Met Phe Ala Val Ile Gly Val Gln Leu
        1480                1485                1490

TTT AAG GGC AAA TTT TTC AAG TGC ACT GAT GGT TCC AAA ATG ACT CAA       4686
Phe Lys Gly Lys Phe Phe Lys Cys Thr Asp Gly Ser Lys Met Thr Gln
1495                1500                1505                1510

GAT GAA TGC TAC GGA ACC TAT CTG GTC TAT GAT GAT GGC GAT GTT CAT       4734
Asp Glu Cys Tyr Gly Thr Tyr Leu Val Tyr Asp Asp Gly Asp Val His
                    1515                1520                1525

AAG CCG CGA CTC AGG GAA CGG GAA TGG AGT AAC AAT CGC TTC CAC TTC       4782
Lys Pro Arg Leu Arg Glu Arg Glu Trp Ser Asn Asn Arg Phe His Phe
                1530                1535                1540

GAT GAT GTG GCC AAG GGC ATG TTG ACT TTG TTC ACG GTG TCC ACA TTT       4830
Asp Asp Val Ala Lys Gly Met Leu Thr Leu Phe Thr Val Ser Thr Phe
            1545                1550                1555

GAG GGC TGG CCA GGT TTG CTG TAT GTT TCA ATT GAT TCG AAT AAG GAA       4878
Glu Gly Trp Pro Gly Leu Leu Tyr Val Ser Ile Asp Ser Asn Lys Glu
        1560                1565                1570

AAC GGC GGT CCA ATA CAC AAC TTC CGT CCG ATC GTA GCT GCC TAC TAT       4926
Asn Gly Gly Pro Ile His Asn Phe Arg Pro Ile Val Ala Ala Tyr Tyr
1575                1580                1585                1590

ATA ATC TAC ATT ATT ATT ATT GCC TTC TTC ATG GTG AAC ATA TTC GTC       4974
Ile Ile Tyr Ile Ile Ile Ile Ala Phe Phe Met Val Asn Ile Phe Val
                    1595                1600                1605

GGT TTC GTT ATC GTC ACT TTC CAA AAT GAG GGT GAA CAG GAA TAT AAG       5022
Gly Phe Val Ile Val Thr Phe Gln Asn Glu Gly Glu Gln Glu Tyr Lys
                1610                1615                1620

AAT TGT GAT CTG GAT AAG AAT CAG CGC AAT TGC ATA GAA TTT GCC TTG       5070
Asn Cys Asp Leu Asp Lys Asn Gln Arg Asn Cys Ile Glu Phe Ala Leu
            1625                1630                1635

AAA GCG AAA CCC GTT AGA CGC TAT ATA CCA AAG CAT GGT ATA CAA TAT       5118
Lys Ala Lys Pro Val Arg Arg Tyr Ile Pro Lys His Gly Ile Gln Tyr
        1640                1645                1650

AAG GTC TGG TGG TTC GTC ACG TCG TCA TCC TTC GAG TAC ACA ATA TTC       5166
Lys Val Trp Trp Phe Val Thr Ser Ser Ser Phe Glu Tyr Thr Ile Phe
1655                1660                1665                1670

ATA CTG ATC ATG ATA AAC ACG GTA ACG CTG GCT ATG AAG TTT TAC AAT       5214
Ile Leu Ile Met Ile Asn Thr Val Thr Leu Ala Met Lys Phe Tyr Asn
                    1675                1680                1685

CAG CCG CTG TGG TAC ACG GAA CTT TTA GAT GCC TTG AAT ATG ATA TTT       5262
Gln Pro Leu Trp Tyr Thr Glu Leu Leu Asp Ala Leu Asn Met Ile Phe
                1690                1695                1700

ACG GCG GTG TTT GCT TTG GAA TTT GTC TTT AAA TTA GCC GCG TTT CGA       5310
Thr Ala Val Phe Ala Leu Glu Phe Val Phe Lys Leu Ala Ala Phe Arg
            1705                1710                1715

TTT AAG AAC TAC TTT GGA GAT GCT TGG AAC GTA TTC GAT TTT ATC ATC       5358
Phe Lys Asn Tyr Phe Gly Asp Ala Trp Asn Val Phe Asp Phe Ile Ile
```

```
              1720              1725              1730
GTT TTA GGC AGT TTC ATT GAC ATT GTC TAC TCT GAA ATT AAG AGC AAG      5406
Val Leu Gly Ser Phe Ile Asp Ile Val Tyr Ser Glu Ile Lys Ser Lys
1735              1740              1745              1750

GAT ACT TCT CAG ATA GCA GAA TGT GAC ATT GTA GAG GGC TGC AAA TCC      5454
Asp Thr Ser Gln Ile Ala Glu Cys Asp Ile Val Glu Gly Cys Lys Ser
              1755              1760              1765

ACC AAG AAA TCA GCT GGT TCA AAT TTA ATA TCC ATC AAT TTC TTC CGA      5502
Thr Lys Lys Ser Ala Gly Ser Asn Leu Ile Ser Ile Asn Phe Phe Arg
         1770              1775              1780

CTG TTC CGA GTT ATG CGA CTC GTC AAG CTT CTC AGC AAA GGC GAG GGC      5550
Leu Phe Arg Val Met Arg Leu Val Lys Leu Leu Ser Lys Gly Glu Gly
    1785              1790              1795

ATT CGA ACA TTA CTG TGG ACT TTT ATC AAA TCC TTC CAG GCA CTG CCC      5598
Ile Arg Thr Leu Leu Trp Thr Phe Ile Lys Ser Phe Gln Ala Leu Pro
1800              1805              1810

TAC GTA GCC CTG CTA ATT GTG CTT CTA TTT TTC ATT TAT GCG GTT GTG      5646
Tyr Val Ala Leu Leu Ile Val Leu Leu Phe Phe Ile Tyr Ala Val Val
1815              1820              1825              1830

GGG ATG CAA GTG TTC GGC AAA ATT GCT CTA GAT GGT GGA AAC GCC ATC      5694
Gly Met Gln Val Phe Gly Lys Ile Ala Leu Asp Gly Gly Asn Ala Ile
              1835              1840              1845

ACG GCC AAT AAC AAT TTC CAA ACG TTC CAG CAG GCT GTT TTA GTA CTC      5742
Thr Ala Asn Asn Asn Phe Gln Thr Phe Gln Gln Ala Val Leu Val Leu
         1850              1855              1860

TTC CGA TCG GCC ACC GGA GAA GCT TGG CAG GAA ATT ATG ATG TCC TGC      5790
Phe Arg Ser Ala Thr Gly Glu Ala Trp Gln Glu Ile Met Met Ser Cys
    1865              1870              1875

TCG GCG CAA CCG GAT GTG AAG TGC GAT ATG AAT TCA GAT ACG CCG GGA      5838
Ser Ala Gln Pro Asp Val Lys Cys Asp Met Asn Ser Asp Thr Pro Gly
1880              1885              1890

GAA CCA TGC GGT TCC TCA ATA GCC TAT CCG TAC TTT ATT TCC TTC TAT      5886
Glu Pro Cys Gly Ser Ser Ile Ala Tyr Pro Tyr Phe Ile Ser Phe Tyr
1895              1900              1905              1910

GTT CTC TGC TCG TTT TTG ATT ATT AAT CTT TTC GTG GCC GTC ATT ATG      5934
Val Leu Cys Ser Phe Leu Ile Ile Asn Leu Phe Val Ala Val Ile Met
              1915              1920              1925

GAC AAC TTT GAC TAT CTG ACT CGT GAT TGG TCG ATT TTG GGT CCC CAC      5982
Asp Asn Phe Asp Tyr Leu Thr Arg Asp Trp Ser Ile Leu Gly Pro His
         1930              1935              1940

CAC TTG GAC GAG TTT ATT CGC CTT TGG AGC GAA TAC GAT CCG GAT GCC      6030
His Leu Asp Glu Phe Ile Arg Leu Trp Ser Glu Tyr Asp Pro Asp Ala
    1945              1950              1955

AAG GGA CGC ATC AAA CAC TTG GAT GTG GTC ACA TTG CTG AGA AAG ATC      6078
Lys Gly Arg Ile Lys His Leu Asp Val Val Thr Leu Leu Arg Lys Ile
1960              1965              1970

TCC CCA CCA CTT GGC TTC GGC AAA CTG TGT CCA CAT AGA ATG GCC TGC      6126
Ser Pro Pro Leu Gly Phe Gly Lys Leu Cys Pro His Arg Met Ala Cys
1975              1980              1985              1990

AAG CGA CTG GTT TCC ATG AAC ATG CCC CTC AAC TCA GAT GGA ACG GTT      6174
Lys Arg Leu Val Ser Met Asn Met Pro Leu Asn Ser Asp Gly Thr Val
              1995              2000              2005

CTC TTC AAT GCC ACA CTG TTT GCT GTG GTC CGC ACT TCG CTG AGC ATC      6222
Leu Phe Asn Ala Thr Leu Phe Ala Val Val Arg Thr Ser Leu Ser Ile
         2010              2015              2020

AAA ACT GAC GGT AAT ATC GAT GAT GCC AAC TCC GAG CTG CGC GCC ACT      6270
Lys Thr Asp Gly Asn Ile Asp Asp Ala Asn Ser Glu Leu Arg Ala Thr
    2025              2030              2035

ATC AAG CAG ATC TGG AAG CGT ACC AAT CCG AAG CTT CTG GAT CAG GTT      6318
```

```
Ile Lys Gln Ile Trp Lys Arg Thr Asn Pro Lys Leu Leu Asp Gln Val
        2040                2045                2050

GTT CCA CCG CCG GGC AAC GAT GAC GAG GTG ACC GTC GGC AAG TTC TAC    6366
Val Pro Pro Pro Gly Asn Asp Asp Glu Val Thr Val Gly Lys Phe Tyr
2055                2060                2065                2070

GCC ACA TAT CTA ATT CAG GAC TAC TTC CGG CGC TTC AAG AAG CGC AAG    6414
Ala Thr Tyr Leu Ile Gln Asp Tyr Phe Arg Arg Phe Lys Lys Arg Lys
                2075                2080                2085

GAA CAG GAG GGC AAG GAG GGT CAT CCG GAC AGC AAT ACA GTC ACG CTG    6462
Glu Gln Glu Gly Lys Glu Gly His Pro Asp Ser Asn Thr Val Thr Leu
        2090                2095                2100

CAG GCC GGC TTG CGA ACC TTA CAC GAA GTG TCC CCA GCT CTA AAG AGA    6510
Gln Ala Gly Leu Arg Thr Leu His Glu Val Ser Pro Ala Leu Lys Arg
        2105                2110                2115

GCC ATC TCC GGC AAT CTC GAC GAG CTG GAC CAG GAG CCG GAG CCC ATG    6558
Ala Ile Ser Gly Asn Leu Asp Glu Leu Asp Gln Glu Pro Glu Pro Met
        2120                2125                2130

CAT CGT CGT CAT CAT ACG CTT TTC GGC AGC GTG TGG TCA TCG ATC CGC    6606
His Arg Arg His His Thr Leu Phe Gly Ser Val Trp Ser Ser Ile Arg
2135                2140                2145                2150

CGA CAT GGA AAC GGA ACC TTC AGG CGA AGT GCC AAG GCA ACT GCT TCG    6654
Arg His Gly Asn Gly Thr Phe Arg Arg Ser Ala Lys Ala Thr Ala Ser
                2155                2160                2165

CAG AGC AAC GGA GCC TTG GCG ATC GGT GGA TCC GCG TCC GCG GCC TTG    6702
Gln Ser Asn Gly Ala Leu Ala Ile Gly Gly Ser Ala Ser Ala Ala Leu
        2170                2175                2180

GGT GTG GGC GGT AGC TCG CTG GTC CTG GGA AGC AGC GAT CCC GCT GGC    6750
Gly Val Gly Gly Ser Ser Leu Val Leu Gly Ser Ser Asp Pro Ala Gly
        2185                2190                2195

GGG GAT TAT CTG TAC GAC ACT CTG AAC CGC AGC GTA GCC GAC GGA GTG    6798
Gly Asp Tyr Leu Tyr Asp Thr Leu Asn Arg Ser Val Ala Asp Gly Val
        2200                2205                2210

AAC AAT ATA ACG CGG AAC ATA ATG CAG GCC CGT TTG GCG GCA GCC GGA    6846
Asn Asn Ile Thr Arg Asn Ile Met Gln Ala Arg Leu Ala Ala Ala Gly
2215                2220                2225                2230

AAG CTG CAG GAC GAA CTG CAG GGG GCA GGA AGT GGC GGA GAG CTA AGG    6894
Lys Leu Gln Asp Glu Leu Gln Gly Ala Gly Ser Gly Gly Glu Leu Arg
                2235                2240                2245

ACA TTC GGC GAG AGC ATA TCC ATG CGA CCG CTG GCC AAA AAT GGA GGC    6942
Thr Phe Gly Glu Ser Ile Ser Met Arg Pro Leu Ala Lys Asn Gly Gly
        2250                2255                2260

GGA GCG GCC ACT GTG GCC GGA ACA CTG CCG CCT GAG GCG AAT GCC ATT    6990
Gly Ala Ala Thr Val Ala Gly Thr Leu Pro Pro Glu Ala Asn Ala Ile
        2265                2270                2275

AAC TAT GAC AAC CGC AAT CGT GGT ATT TTA TTG CAT CCA TAT AAC AAT    7038
Asn Tyr Asp Asn Arg Asn Arg Gly Ile Leu Leu His Pro Tyr Asn Asn
        2280                2285                2290

GTC TAC GCA CCC AAT GGT GCT CTT CCT GGC CAC GAA CGC ATG ATC CAA    7086
Val Tyr Ala Pro Asn Gly Ala Leu Pro Gly His Glu Arg Met Ile Gln
2295                2300                2305                2310

TCG ACA CCA GCT AGT CCC TAC GAT CAG CGT CGT TTA CCA ACT TCA TCT    7134
Ser Thr Pro Ala Ser Pro Tyr Asp Gln Arg Arg Leu Pro Thr Ser Ser
                2315                2320                2325

GAT ATG AAC GGT CTA GCC GAA TCA TTG ATT GGA GGG GTA CTC GCC GCT    7182
Asp Met Asn Gly Leu Ala Glu Ser Leu Ile Gly Gly Val Leu Ala Ala
        2330                2335                2340

GAA GGG ATG GGT AAA TAC TGC GAC TCC GAG TTC GTG GGG ACT GCT GCA    7230
Glu Gly Met Gly Lys Tyr Cys Asp Ser Glu Phe Val Gly Thr Ala Ala
        2345                2350                2355
```

```
CGG GAG ATG CGC GAA GCG CTG GAC ATG ACG CCC GAG GAA ATG AAC CTG      7278
Arg Glu Met Arg Glu Ala Leu Asp Met Thr Pro Glu Glu Met Asn Leu
         2360               2365               2370

GCC GCC CAC CAG ATC CTC TCC AAC GAG CAC TCG CTG AGT CTG ATC GGC      7326
Ala Ala His Gln Ile Leu Ser Asn Glu His Ser Leu Ser Leu Ile Gly
2375             2380               2385               2390

AGT AGC AAT GGT AGC ATC TTC GGT GGA TCC GCC GGT GGC CTG GGA GGG      7374
Ser Ser Asn Gly Ser Ile Phe Gly Gly Ser Ala Gly Gly Leu Gly Gly
             2395               2400               2405

GCT GGA TCT GGA GGT GTG GGT GGA TTG GGC GGT AGT AGC AGC ATT CGC      7422
Ala Gly Ser Gly Gly Val Gly Gly Leu Gly Gly Ser Ser Ser Ile Arg
         2410               2415               2420

AAC GCT TTC GGC GGA AGC GGA AGT GGA CCG TCC TCG CTG TCG CCG CAA      7470
Asn Ala Phe Gly Gly Ser Gly Ser Gly Pro Ser Ser Leu Ser Pro Gln
         2425               2430               2435

CAT CAG CCT TAC TCG GGC ACT CTG AAC TCA CCA CCG ATT CCG GAT AAT      7518
His Gln Pro Tyr Ser Gly Thr Leu Asn Ser Pro Pro Ile Pro Asp Asn
         2440               2445               2450

CGT CTG AGA CGT GTT GCC ACA GTC ACG ACC ACA AAC AAT AAC AAT AAG      7566
Arg Leu Arg Arg Val Ala Thr Val Thr Thr Thr Asn Asn Asn Asn Lys
2455             2460               2465               2470

TCC CAA GTT AGC CAA AAC AAT TCG AGT AGC TTA AAT GTT AGG GCT AAT      7614
Ser Gln Val Ser Gln Asn Asn Ser Ser Ser Leu Asn Val Arg Ala Asn
             2475               2480               2485

GCC AAT AGC CAA ATG AAC ATG TCA CCA ACT GGA CAA CCA GTG CAG CAA      7662
Ala Asn Ser Gln Met Asn Met Ser Pro Thr Gly Gln Pro Val Gln Gln
         2490               2495               2500

CAA TCG CCG CTA AGA GGA CAG GGC AAT CAG ACT TAC TCC TCA              7704
Gln Ser Pro Leu Arg Gly Gln Gly Asn Gln Thr Tyr Ser Ser
         2505               2510               2515

TAGCACCCAC ATTGTAAGCT ATACATACAG AATGTCTTCT TGATGGAACT TTAAATGTGC    7764

ATTCAGCGCA AGCTGAGGTT TATTGGCTAA TTTATTTGTT ATTTTTAGCG AAGAAAAACA    7824

CATTAGTCTT AGCATCGGGA ATTGTTATAT TTGAATTGTT CGCACACACA CAAGCGGGAA    7884

CCAAACCAAC AAAACTTGTA TAACTTGTAT AAAGAAAATC AGCTAATTGT ATATGTATAA    7944

ATATATTAAT GTTTTTGCCT TTTTGAGAAA TCTATCGTGG GCCTTCGTCC TCTAACGAGC    8004

CAGAAAACCA AAAAACCAAC AACACTAAAC TGAACAAATT AAGGAAAAAT GTATATTTTT    8064

GGATAAAAAA A                                                        8075
```

(2) INFORMATION FOR SEQ ID NO: 2:

(i) SEQUENCE CHARACTERISTICS:
        (A) LENGTH: 2516 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Gly Gly Gly Glu Leu Val Asn Cys Ile Ala Tyr Asp Asp Asn Thr
1               5                   10                  15

Leu Val Ile Glu Arg Lys Pro Ser Pro Ser Pro Ser Thr Ser Arg
            20                  25                  30

Arg Tyr Leu Lys Ala Glu Thr Pro Thr Arg Gly Ser Arg Lys Tyr Asn
        35                  40                  45

Arg Lys Ser Ser Ala Lys Ser Asp Leu Glu Val Val Val Lys Pro
    50                  55                  60

Glu His His His Gln His Arg Ser Pro Thr Ile Thr Leu Pro Val Pro
```

-continued

```
             65                  70                  75                  80
Ala Asn Pro Leu Thr Thr Ser Ala Ser Ala Gly Ser Ser Pro Thr Gly
                     85                  90                  95
Ala Gly Leu Ala Ala Gly Leu Gly Thr Ala Ser Gly Thr Val Leu Gln
            100                 105                 110
Gln Ser Cys Ser Ala Leu Asp Pro Pro Glu Asp Ser Asn Gln Pro Ser
            115                 120                 125
Gly Thr Arg Arg Arg Ala Thr Ser Thr Glu Leu Ala Leu Ser Asn Val
            130                 135                 140
Thr Ser Gln Ile Val Asn Asn Ala Thr Tyr Lys Leu Asp Phe Lys Gln
145                 150                 155                 160
Arg Arg His Lys Ser Asn Asn Gly Gly Ser Glu Ser Gly Ser Leu Thr
                    165                 170                 175
Gly Ile Ala Thr Gly Pro Ala Thr Ser Pro Ala Gly Pro Thr Gly Pro
                    180                 185                 190
Thr Ser Ser Ser Gly Lys Arg Arg Lys Ser Ser Cys Thr Ser Cys Gly
                    195                 200                 205
Gly Gly Gly Ile Ser Ala Pro Pro Arg Leu Thr Pro Glu Glu Ala
210                 215                 220
Trp Gln Leu Gln Pro Gln Asn Ser Val Thr Ser Ala Gly Ser Thr Asn
225                 230                 235                 240
Ser Ser Phe Ser Ser Gly Gly Arg Asp Asp Asn Ser Ser Tyr Ser
                    245                 250                 255
Ala Val Gly Gly Asp Ser Ser Ser Asn Ser Cys Asn Cys Asp Ile
                    260                 265                 270
Thr Gly Asp Asn Ser Thr Leu His Gly Leu Gly Val Gly Asp Val Cys
                    275                 280                 285
Ser Phe Ile Ala Asp Cys Asp Asp Asn Ser Glu Asp Asp Gly Asp
                    290                 295                 300
Pro Asn Asn Gln Asp Leu Ser Ser Gln Thr Leu Arg Thr Ala Ala Ile
305                 310                 315                 320
Val Ala Ala Val Ala Ala Ala Lys Glu Gln Ala Gln Glu Gln Ser
                    325                 330                 335
Leu Ala Asp Cys Glu Ser Phe Ser Asp Arg Arg Gln Asp Ala Asp Glu
                    340                 345                 350
Asp Val Arg Ile Ile Gln Asp Cys Cys Gly Gly Asn Asn Asp Ser Leu
                    355                 360                 365
Glu Asp Val Gly Glu Val Asp Asp Asn Ala Asp Val Val Arg Lys
                    370                 375                 380
Asn Ser Arg Asn Arg Pro Ser Ile Arg Arg Thr Cys Arg Ile Thr Glu
385                 390                 395                 400
Glu Asp Asp Asp Glu Asp Glu Asn Ala Asp Tyr Gly Asp Phe Asp Arg
                    405                 410                 415
Glu Asp Gln Glu Leu Asp Asp Glu Pro Glu Gly Thr Thr Ile Asp
                    420                 425                 430
Ile Asp Glu Gln Glu Gln Gln His Asp Gln Gly Asp Ser Ala Glu Glu
                    435                 440                 445
Glu Asp His Asp Glu Asp Val Asp Glu Tyr Phe Glu Glu Glu Asp
                    450                 455                 460
Asp Thr Gln Ala Phe Ser Pro Phe Tyr Ser Ser Ala Glu Leu Ile
465                 470                 475                 480
Asp Asn Phe Gly Gly Gly Ala Gly Lys Phe Phe Asn Ile Met Asp Phe
                    485                 490                 495
```

-continued

```
Glu Arg Gly Ala Ser Gly Glu Gly Gly Phe Ser Pro Asn Gly Asn Gly
            500                 505                 510
Gly Pro Gly Ser Gly Asp Val Ser Arg Thr Ala Arg Tyr Asp Ser Gly
        515                 520                 525
Glu Gly Asp Leu Gly Gly Gly Asn Asn Ile Met Gly Ile Asp Ser Met
    530                 535                 540
Gly Ile Ala Asn Ile Pro Glu Thr Met Asn Gly Thr Thr Ile Gly Pro
545                 550                 555                 560
Ser Gly Ala Gly Gly Gln Lys Gly Gly Ala Ala Gly Ala Ala Gly
            565                 570                 575
Gln Lys Arg Gln Gln Arg Arg Gly Lys Pro Gln Pro Asp Arg Pro Gln
        580                 585                 590
Arg Ala Leu Phe Cys Leu Ser Val Lys Asn Pro Leu Arg Ala Leu Cys
    595                 600                 605
Ile Arg Ile Val Glu Trp Lys Pro Phe Glu Phe Leu Ile Leu Leu Thr
    610                 615                 620
Ile Phe Ala Asn Cys Ile Ala Leu Ala Val Tyr Thr Pro Tyr Pro Gly
625                 630                 635                 640
Ser Asp Ser Asn Val Thr Asn Gln Thr Leu Glu Lys Val Glu Tyr Val
            645                 650                 655
Phe Leu Val Ile Phe Thr Ala Glu Cys Val Met Lys Ile Leu Ala Tyr
            660                 665                 670
Gly Phe Val Leu His Asp Gly Ala Tyr Leu Gly Asn Gly Trp Asn Leu
        675                 680                 685
Leu Asp Phe Thr Ile Val Val Met Gly Ala Ile Ser Thr Ala Leu Ser
    690                 695                 700
Gln Leu Met Lys Asp Ala Phe Asp Val Lys Ala Leu Arg Ala Phe Arg
705                 710                 715                 720
Val Leu Arg Pro Leu Arg Leu Val Ser Gly Val Pro Ser Leu Gln Val
            725                 730                 735
Val Leu Asn Ser Ile Leu Lys Ala Met Val Pro Leu Phe His Ile Ala
            740                 745                 750
Leu Leu Val Leu Phe Val Ile Ile Tyr Ala Ile Ile Gly Leu Glu
        755                 760                 765
Leu Phe Ser Gly Lys Leu His Lys Ala Cys Arg Asp Glu Ile Thr Gly
    770                 775                 780
Glu Tyr Glu Glu Asn Ile Arg Pro Cys Gly Val Gly Tyr Gln Cys Pro
785                 790                 795                 800
Pro Gly Tyr Lys Cys Tyr Gly Gly Trp Asp Gly Pro Asn Asp Gly Ile
            805                 810                 815
Thr Asn Phe Asp Asn Phe Gly Leu Ala Met Leu Thr Val Phe Gln Cys
            820                 825                 830
Val Thr Leu Glu Gly Trp Thr Asp Val Leu Tyr Ser Ile Gln Asp Ala
        835                 840                 845
Met Gly Ser Asp Trp Gln Trp Met Tyr Phe Ile Ser Met Val Ile Leu
    850                 855                 860
Gly Ala Phe Phe Val Met Asn Leu Ile Leu Gly Val Leu Ser Gly Glu
865                 870                 875                 880
Phe Ser Lys Glu Arg Asn Lys Ala Lys Asn Arg Gly Asp Phe Gln Lys
            885                 890                 895
Leu Arg Glu Lys Gln Gln Ile Glu Glu Asp Leu Arg Gly Tyr Leu Asp
            900                 905                 910
```

```
Trp Ile Thr Gln Ala Glu Asp Ile Glu Pro Asp Ala Val Gly Gly Leu
        915                 920                 925
Ile Ser Asp Gly Lys Gly Lys Gln Pro Asn Glu Met Asp Ser Thr Glu
        930                 935                 940
Asn Leu Gly Glu Glu Met Pro Glu Val Gln Met Thr Glu Ser Arg Trp
945                 950                 955                 960
Arg Lys Met Lys Lys Asp Phe Asp Arg Val Asn Arg Arg Met Arg Arg
                965                 970                 975
Ala Cys Arg Lys Ala Val Lys Ser Gln Ala Phe Tyr Trp Leu Ile Ile
                980                 985                 990
Val Leu Val Phe Leu Asn Thr Gly Val Leu Ala Thr Glu His Tyr Gly
        995                 1000                1005
Gln Leu Asp Trp Leu Asp Asn Phe Gln Glu Tyr Thr Asn Val Phe Phe
        1010                1015                1020
Ile Gly Leu Phe Thr Cys Glu Met Leu Leu Lys Met Tyr Ser Leu Gly
1025                1030                1035                1040
Phe Gln Gly Tyr Phe Val Ser Leu Phe Asn Arg Phe Asp Cys Phe Val
                1045                1050                1055
Val Ile Gly Ser Ile Thr Glu Thr Leu Leu Thr Asn Thr Gly Met Met
                1060                1065                1070
Pro Pro Leu Gly Val Ser Val Leu Arg Cys Val Arg Leu Leu Arg Val
        1075                1080                1085
Phe Lys Val Thr Lys Tyr Trp Arg Ser Leu Ser Asn Leu Val Ala Ser
        1090                1095                1100
Leu Leu Asn Ser Ile Gln Ser Ile Ala Ser Leu Leu Leu Leu Leu Phe
1105                1110                1115                1120
Leu Phe Ile Val Ile Phe Ala Leu Leu Gly Met Gln Val Phe Gly Gly
                1125                1130                1135
Lys Phe Asn Phe Asp Gly Lys Glu Glu Lys Tyr Arg Met Asn Phe Asp
                1140                1145                1150
Cys Phe Trp Gln Ala Leu Leu Thr Val Phe Gln Ile Met Thr Gly Glu
        1155                1160                1165
Asp Trp Asn Ala Val Met Tyr Val Gly Ile Asn Ala Tyr Gly Gly Val
        1170                1175                1180
Ser Ser Tyr Gly Ala Leu Ala Cys Ile Tyr Phe Ile Ile Leu Phe Ile
1185                1190                1195                1200
Cys Gly Asn Tyr Ile Leu Leu Asn Val Phe Leu Ala Ile Ala Val Asp
                1205                1210                1215
Asn Leu Ala Asp Ala Asp Ser Leu Ser Glu Val Glu Lys Glu Glu Glu
                1220                1225                1230
Pro His Asp Glu Ser Ala Gln Lys Lys Ser His Ser Pro Thr Pro Thr
        1235                1240                1245
Ile Asp Gly Met Asp Asp His Leu Ser Ile Asp Met Glu Gln
        1250                1255                1260
Gln Glu Leu Asp Asp Glu Asp Lys Met Asp His Glu Thr Leu Ser Asp
1265                1270                1275                1280
Glu Glu Val Arg Glu Met Cys Glu Glu Glu Glu Val Asp Glu Glu
                1285                1290                1295
Gly Met Ile Thr Ala Arg Pro Arg Arg Met Ser Glu Val Asn Thr Ala
                1300                1305                1310
Thr Lys Ile Leu Pro Ile Pro Pro Gly Thr Ser Phe Phe Leu Phe Ser
        1315                1320                1325
Gln Thr Asn Arg Phe Arg Val Phe Cys His Trp Leu Cys Asn His Ser
```

-continued

```
            1330                1335                1340
Asn Phe Gly Asn Ile Ile Leu Cys Cys Ile Met Phe Ser Ser Ala Met
1345                1350                1355                1360
Leu Ala Ala Glu Asn Pro Leu Arg Ala Asn Asp Asp Leu Asn Lys Val
                1365                1370                1375
Leu Asn Lys Phe Asp Tyr Phe Phe Thr Ala Val Phe Thr Met Glu Leu
            1380                1385                1390
Ile Leu Lys Leu Ile Ser Tyr Gly Phe Val Leu His Asp Gly Ala Phe
            1395                1400                1405
Cys Arg Ser Ala Phe Asn Leu Leu Asp Leu Leu Val Val Cys Val Ser
        1410                1415                1420
Leu Ile Ser Leu Val Ser Ser Ser Asp Ala Ile Ser Val Val Lys Ile
1425                1430                1435                1440
Leu Arg Val Leu Arg Val Leu Arg Pro Leu Arg Ala Ile Asn Arg Ala
                1445                1450                1455
Lys Gly Leu Lys His Val Val Gln Cys Val Ile Val Ala Val Lys Thr
            1460                1465                1470
Ile Gly Asn Ile Val Leu Val Thr Cys Leu Leu Gln Phe Met Phe Ala
        1475                1480                1485
Val Ile Gly Val Gln Leu Phe Lys Gly Lys Phe Phe Lys Cys Thr Asp
        1490                1495                1500
Gly Ser Lys Met Thr Gln Asp Glu Cys Tyr Gly Thr Tyr Leu Val Tyr
1505                1510                1515                1520
Asp Asp Gly Asp Val His Lys Pro Arg Leu Arg Glu Arg Glu Trp Ser
                1525                1530                1535
Asn Asn Arg Phe His Phe Asp Asp Val Ala Lys Gly Met Leu Thr Leu
            1540                1545                1550
Phe Thr Val Ser Thr Phe Glu Gly Trp Pro Gly Leu Leu Tyr Val Ser
            1555                1560                1565
Ile Asp Ser Asn Lys Glu Asn Gly Gly Pro Ile His Asn Phe Arg Pro
        1570                1575                1580
Ile Val Ala Ala Tyr Tyr Ile Ile Tyr Ile Ile Ile Ala Phe Phe
1585                1590                1595                1600
Met Val Asn Ile Phe Val Gly Phe Val Ile Val Thr Phe Gln Asn Glu
                1605                1610                1615
Gly Glu Gln Glu Tyr Lys Asn Cys Asp Leu Asp Lys Asn Gln Arg Asn
            1620                1625                1630
Cys Ile Glu Phe Ala Leu Lys Ala Lys Pro Val Arg Arg Tyr Ile Pro
        1635                1640                1645
Lys His Gly Ile Gln Tyr Lys Val Trp Trp Phe Val Thr Ser Ser Ser
        1650                1655                1660
Phe Glu Tyr Thr Ile Phe Ile Leu Ile Met Ile Asn Thr Val Thr Leu
1665                1670                1675                1680
Ala Met Lys Phe Tyr Asn Gln Pro Leu Trp Tyr Thr Glu Leu Leu Asp
                1685                1690                1695
Ala Leu Asn Met Ile Phe Thr Ala Val Phe Ala Leu Glu Phe Val Phe
            1700                1705                1710
Lys Leu Ala Ala Phe Arg Phe Lys Asn Tyr Phe Gly Asp Ala Trp Asn
        1715                1720                1725
Val Phe Asp Phe Ile Ile Val Leu Gly Ser Phe Ile Asp Ile Val Tyr
        1730                1735                1740
Ser Glu Ile Lys Ser Lys Asp Thr Ser Gln Ile Ala Glu Cys Asp Ile
1745                1750                1755                1760
```

-continued

```
Val Glu Gly Cys Lys Ser Thr Lys Lys Ser Ala Gly Ser Asn Leu Ile
            1765                1770                1775
Ser Ile Asn Phe Phe Arg Leu Phe Arg Val Met Arg Leu Val Lys Leu
        1780                1785                1790
Leu Ser Lys Gly Glu Gly Ile Arg Thr Leu Leu Trp Thr Phe Ile Lys
        1795                1800                1805
Ser Phe Gln Ala Leu Pro Tyr Val Ala Leu Leu Ile Val Leu Leu Phe
    1810                1815                1820
Phe Ile Tyr Ala Val Val Gly Met Gln Val Phe Gly Lys Ile Ala Leu
1825                1830                1835                1840
Asp Gly Gly Asn Ala Ile Thr Ala Asn Asn Phe Gln Thr Phe Gln
                1845                1850                1855
Gln Ala Val Leu Val Leu Phe Arg Ser Ala Thr Gly Glu Ala Trp Gln
            1860                1865                1870
Glu Ile Met Met Ser Cys Ser Ala Gln Pro Asp Val Lys Cys Asp Met
            1875                1880                1885
Asn Ser Asp Thr Pro Gly Glu Pro Cys Gly Ser Ser Ile Ala Tyr Pro
        1890                1895                1900
Tyr Phe Ile Ser Phe Tyr Val Leu Cys Ser Phe Leu Ile Ile Asn Leu
1905                1910                1915                1920
Phe Val Ala Val Ile Met Asp Asn Phe Asp Tyr Leu Thr Arg Asp Trp
                1925                1930                1935
Ser Ile Leu Gly Pro His His Leu Asp Glu Phe Ile Arg Leu Trp Ser
            1940                1945                1950
Glu Tyr Asp Pro Asp Ala Lys Gly Arg Ile Lys His Leu Asp Val Val
        1955                1960                1965
Thr Leu Leu Arg Lys Ile Ser Pro Pro Leu Gly Phe Gly Lys Leu Cys
    1970                1975                1980
Pro His Arg Met Ala Cys Lys Arg Leu Val Ser Met Asn Met Pro Leu
1985                1990                1995                2000
Asn Ser Asp Gly Thr Val Leu Phe Asn Ala Thr Leu Phe Ala Val Val
                2005                2010                2015
Arg Thr Ser Leu Ser Ile Lys Thr Asp Gly Asn Ile Asp Asp Ala Asn
            2020                2025                2030
Ser Glu Leu Arg Ala Thr Ile Lys Gln Ile Trp Lys Arg Thr Asn Pro
        2035                2040                2045
Lys Leu Leu Asp Gln Val Val Pro Pro Gly Asn Asp Asp Glu Val
            2050                2055                2060
Thr Val Gly Lys Phe Tyr Ala Thr Tyr Leu Ile Gln Asp Tyr Phe Arg
2065                2070                2075                2080
Arg Phe Lys Lys Arg Lys Glu Gln Glu Gly Lys Glu Gly His Pro Asp
            2085                2090                2095
Ser Asn Thr Val Thr Leu Gln Ala Gly Leu Arg Thr Leu His Glu Val
        2100                2105                2110
Ser Pro Ala Leu Lys Arg Ala Ile Ser Gly Asn Leu Asp Glu Leu Asp
    2115                2120                2125
Gln Glu Pro Glu Pro Met His Arg His His Thr Leu Phe Gly Ser
        2130                2135                2140
Val Trp Ser Ser Ile Arg Arg His Gly Asn Gly Thr Phe Arg Arg Ser
2145                2150                2155                2160
Ala Lys Ala Thr Ala Ser Gln Ser Asn Gly Ala Leu Ala Ile Gly Gly
            2165                2170                2175
```

Ser Ala Ser Ala Ala Leu Gly Val Gly Gly Ser Ser Leu Val Leu Gly
                2180                2185                2190

Ser Ser Asp Pro Ala Gly Gly Asp Tyr Leu Tyr Asp Thr Leu Asn Arg
            2195                2200                2205

Ser Val Ala Asp Gly Val Asn Asn Ile Thr Arg Asn Ile Met Gln Ala
        2210                2215                2220

Arg Leu Ala Ala Ala Gly Lys Leu Gln Asp Glu Leu Gln Gly Ala Gly
2225                2230                2235                2240

Ser Gly Gly Glu Leu Arg Thr Phe Gly Glu Ser Ile Ser Met Arg Pro
                2245                2250                2255

Leu Ala Lys Asn Gly Gly Gly Ala Ala Thr Val Ala Gly Thr Leu Pro
            2260                2265                2270

Pro Glu Ala Asn Ala Ile Asn Tyr Asp Asn Arg Asn Arg Gly Ile Leu
        2275                2280                2285

Leu His Pro Tyr Asn Asn Val Tyr Ala Pro Asn Gly Ala Leu Pro Gly
            2290                2295                2300

His Glu Arg Met Ile Gln Ser Thr Pro Ala Ser Pro Tyr Asp Gln Arg
2305                2310                2315                2320

Arg Leu Pro Thr Ser Ser Asp Met Asn Gly Leu Ala Glu Ser Leu Ile
                2325                2330                2335

Gly Gly Val Leu Ala Ala Glu Gly Met Gly Lys Tyr Cys Asp Ser Glu
            2340                2345                2350

Phe Val Gly Thr Ala Ala Arg Glu Met Arg Glu Ala Leu Asp Met Thr
        2355                2360                2365

Pro Glu Glu Met Asn Leu Ala Ala His Gln Ile Leu Ser Asn Glu His
2370                2375                2380

Ser Leu Ser Leu Ile Gly Ser Ser Asn Gly Ser Ile Phe Gly Gly Ser
2385                2390                2395                2400

Ala Gly Gly Leu Gly Gly Ala Gly Ser Gly Gly Val Gly Gly Leu Gly
                2405                2410                2415

Gly Ser Ser Ser Ile Arg Asn Ala Phe Gly Gly Ser Gly Ser Gly Pro
            2420                2425                2430

Ser Ser Leu Ser Pro Gln His Gln Pro Tyr Ser Gly Thr Leu Asn Ser
        2435                2440                2445

Pro Pro Ile Pro Asp Asn Arg Leu Arg Arg Val Ala Thr Val Thr Thr
        2450                2455                2460

Thr Asn Asn Asn Lys Ser Gln Val Ser Gln Asn Ser Ser Ser
2465                2470                2475                2480

Leu Asn Val Arg Ala Asn Ala Asn Ser Gln Met Asn Met Ser Pro Thr
            2485                2490                2495

Gly Gln Pro Val Gln Gln Ser Pro Leu Arg Gly Gln Gly Asn Gln
            2500                2505                2510

Thr Tyr Ser Ser
        2515

(2) INFORMATION FOR SEQ ID NO: 3:

(i) SEQUENCE CHARACTERISTICS:
        (A) LENGTH: 785 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

-continued

```
Met Ser Glu Val Asn Thr Ala Thr Lys Ile Leu Pro Ile Pro Pro Gly
1               5                   10                  15

Thr Ser Phe Phe Leu Phe Ser Gln Thr Asn Arg Phe Arg Val Phe Cys
            20                  25                  30

His Trp Leu Cys Asn His Ser Asn Glu Gly Asn Met Val Gly Gly Gly
            35                  40                  45

Ile Met Glu Ser Ser Ala Met Glu Ala Ala Glu Asn Pro Leu Arg Ala
    50                  55                  60

Asn Asp Asp Leu Asn Lys Val Leu Asn Lys Glu Asp Tyr Phe Glu Thr
65                  70                  75                  80

Ala Val Phe Asp Pro Glu Leu Ile Leu Lys Asp Ile Ser Tyr Gly Phe
                85                  90                  95

Val Leu His Asp Gly Ala Phe Cys Arg Ser Ala Arg Asn Glu Leu Asp
            100                 105                 110

Leu Leu Val Val Cys Val Ser Ile Leu Ser Leu Val Ser Ser Ser Asn
            115                 120                 125

Ala Ile Ser Val Val Lys Ile Leu Arg Val Leu Arg Val Leu Arg Pro
    130                 135                 140

Asx Arg Ala Ile Asn Arg Ala Lys Gly Leu Lys His Val Val Gln Cys
145                 150                 155                 160

Ile Val Ala Val Thr Lys Thr Ile Gly Asn Ile Val Leu Val Ile Gly
                165                 170                 175

Leu Leu Gln Phe Met Glu Ala Val Ile Gly Val Leu Phe Lys Gly Lys
            180                 185                 190

Phe Phe Lys Cys Thr Asp Gly Ser Lys Met Thr Gln Asp Glu Cys Tyr
            195                 200                 205

Gly Thr Tyr Leu Val Tyr Asp Asp Gly Asp Val His Lys Pro Arg Leu
    210                 215                 220

Arg Glu Arg Glu Trp Ser Asn Asn Arg Phe His Phe Asp Asp Val Ala
225                 230                 235                 240

Lys Gly Met Leu Thr Leu Phe Thr Val Ser Thr Phe Glu Gly Trp Pro
                245                 250                 255

Gly Leu Leu Tyr Val Ser Ile Asp Ser Asn Lys Glu Asn Gly Gly Pro
            260                 265                 270

Ile His Asn Phe Arg Pro Ile Val Ala Ala Tyr Tyr Asp Ile Tyr Ile
            275                 280                 285

Ile Ile Tyr Ala Phe Phe Met Val Asn Ile Glu Val Gly Arg Val Ile
    290                 295                 300

Val Thr Phe Gln Asn Glu Gly Glu Gln Glu Tyr Lys Asn Cys Asp Leu
305                 310                 315                 320

Asp Lys Asn Gln Arg Asn Cys Ile Glu Phe Ala Leu Lys Ala Lys Pro
                325                 330                 335

Val Arg Arg Tyr Ile Pro Lys His Gly Ile Gln Tyr Lys Val Trp Trp
            340                 345                 350

Phe Val Thr Ser Ser Ser Glu Glu Tyr Thr Ile Glu Ile Leu Ile Met
            355                 360                 365

Ile Asn Thr Val Thr Leu Ala Met Lys Phe Tyr Asn Gln Pro Leu Trp
    370                 375                 380

Tyr Thr Glu Leu Leu Asp Ala Leu Asn Met Ile Glu Ile Ala Val Glu
385                 390                 395                 400

Ala Leu Glu Glu Val Glu Lys Leu Ala Ala Phe Arg Phe Lys Asn Tyr
                405                 410                 415

Phe Gly Asp Ala Trp Asn Val Glu Asp Glu Ile Leu Val Leu Gly Ser
```

-continued

```
                420             425             430
Phe Ile Asp Leu Val Tyr Ser Glu Ile Lys Ser Lys Asp Thr Ser Gln
            435             440             445

Ile Ala Glu Cys Asp Ile Val Glu Gly Cys Lys Ser Thr Lys Lys Ser
450             455             460

Ala Gly Ser Asn Leu Ile Ser Ile Asn Phe Phe Arg Leu Glu Arg Val
465             470             475             480

Met Arg Leu Val Lys Leu Leu Ser Lys Gly Glu Gly Ile Arg Thr Leu
            485             490             495

Leu Trp Thr Phe Ile Lys Ser Phe Gln Ala Leu Pro Tyr Val Ala Leu
            500             505             510

Leu Ile Val Leu Leu Glu Glu Ile Tyr Ala Val Val Gly Met Val Glu
            515             520             525

Gly Lys Ile Ala Leu Asp Gly Gly Asn Ala Ile Thr Ala Asn Asn Asn
            530             535             540

Phe Gln Thr Phe Gln Gln Ala Val Leu Val Leu Phe Arg Ser Ala Thr
545             550             555             560

Gly Glu Ala Trp Gln Glu Ile Met Met Ser Cys Ser Ala Gln Pro Asp
            565             570             575

Val Lys Cys Asp Met Asn Ser Asp Thr Pro Gly Glu Pro Cys Gly Ser
            580             585             590

Ser Ile Ala Tyr Arg Tyr Glu Ile Ser Glu Tyr Val Leu Cys Ser Phe
            595             600             605

Leu Leu Ile Asn Leu Glu Val Ala Val Ile Met Asp Asn Phe Asp Tyr
            610             615             620

Leu Thr Arg Asp Trp Ser Ile Leu Gly Pro His His Leu Asp Glu Phe
625             630             635             640

Ile Arg Leu Trp Ser Glu Tyr Asp Pro Asp Ala Lys Gly Arg Ile Lys
            645             650             655

His Leu Asp Val Val Thr Leu Leu Arg Lys Ile Ser Pro Pro Leu Gly
            660             665             670

Phe Gly Lys Leu Cys Pro His Arg Met Ala Cys Lys Arg Leu Val Ser
            675             680             685

Met Asn Met Pro Leu Asn Ser Asp Gly Thr Val Leu Phe Asn Ala Thr
690             695             700

Leu Phe Ala Val Val Arg Thr Ser Leu Ser Ile Lys Thr Asp Gly Asn
705             710             715             720

Ile Asp Asp Ala Asn Ser Glu Leu Arg Ala Thr Ile Lys Gln Ile Trp
            725             730             735

Lys Arg Thr Asn Pro Lys Leu Leu Asp Gln Val Val Pro Pro Pro Gly
            740             745             750

Asn Asp Asp Glu Val Thr Val Gly Lys Phe Tyr Ala Thr Tyr Leu Ile
            755             760             765

Gln Asp Tyr Phe Arg Arg Phe Lys Lys Arg Lys Glu Gln Glu Gly Lys
            770             775             780

Glu
785
```

(2) INFORMATION FOR SEQ ID NO: 4:

(i) SEQUENCE CHARACTERISTICS:
        (A) LENGTH: 793 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Glu Ile Pro Val Ser Pro Arg Pro Arg Pro Leu Ala Glu Leu Gln Leu
1               5                   10                  15

Lys Glu Lys Ala Val Pro Ile Pro Glu Ala Ser Ser Phe Phe Ile Phe
                20                  25                  30

Ser Pro Thr Asn Lys Val Arg Val Leu Cys His Arg Ile Val Asn Ala
            35                  40                  45

Thr Trp Glu Ile Asn Glu Ile Leu Leu Phe Ile Leu Leu Ser Ser Ala
    50                  55                  60

Ala Asp Ala Ala Glu Asp Pro Ile Arg Ala Glu Ser Val Arg Asn Gln
65                  70                  75                  80

Ile Leu Gly Tyr Glu Asp Ile Ala Phe Ile Ser Val Glu Thr Val Glu
                85                  90                  95

Leu Val Leu Arg Met Ile Ser Tyr Gly Ala Phe Leu His Lys Gly Phe
                100                 105                 110

Ser Cys Arg Asn Leu Lys Asn Asn Ile Asp Ala Leu Leu Val Val Ala
                115                 120                 125

Val Gly Ile Arg Lys Met Ile Glu Ser Ser Thr Ile Ser Val Val Lys
    130                 135                 140

Ile Ile Arg Met Leu Arg Val Met Leu Arg His His Arg Ala Val Asn
145                 150                 155                 160

Arg Ala Lys Gly Leu Lys His Val Val Gln Cys Phe Val Ala Ile Arg
                165                 170                 175

Thr Ile Gly Asn Ile Val Ile Val Ile Thr Leu Leu Gln Glu Met Glu
                180                 185                 190

Ala Gln Ile Gln Val Gln Leu Glu Lys Gly Lys Phe Phe Ser Cys Asn
    195                 200                 205

Asp Leu Ser Lys Met Thr Glu Glu Cys Arg Gly Tyr Tyr Tyr Val
    210                 215                 220

Tyr Lys Asp Gly Asp Pro Thr Gln Met Glu Leu Arg Pro Arg Trp Ile
225                 230                 235                 240

His Asn Asp Phe His Phe Asp Asn Val Leu Ser Ala Met Met Ser Leu
                245                 250                 255

Phe Thr Val Ser Thr Phe Glu Gly Trp Pro Gln Leu Leu Tyr Arg Ala
                260                 265                 270

Ile Asp Ser Asn Glu Glu Asp Met Gly Pro Val Tyr Asn Asn Arg Val
    275                 280                 285

Glu Met Ala Ile Phe Phe Ile Ile Tyr Ile Ile Leu Ile Ala Lys Glu
290                 295                 300

Met Met Asn Gln Phe Val Gly Ile Ala Ala Val Thr Phe Gln Glu Gln
305                 310                 315                 320

Gly Glu Thr Glu Tyr Lys Asn Cys Glu Leu Asp Lys Asn Gln Arg Gln
                325                 330                 335

Cys Val Gln Tyr Ala Leu Lys Ala Arg Pro Leu Arg Cys Tyr Ile Pro
                340                 345                 350

Lys Asn Pro Tyr Gln Tyr Gln Val Trp Tyr Val Val Thr Ser Ser Tyr
                355                 360                 365

Glu Glu Tyr Leu Met Glu Ala Leu Ile Met Leu Asn Thr Ile Gly Leu
                370                 375                 380

Gly Met Gln His Tyr His Gln Ser Glu Glu Met Asn His Ile Ser Asp
385                 390                 395                 400
```

-continued

```
Ile Leu Asn Val Ala Arg Asp Leu Glu Arg Ile Leu Glu Met Ile Asp
                405                 410                 415
Lys Asn Asn Ala Phe Lys Ala Arg Gly Tyr Phe Gly Asp Arg Trp Asn
            420                 425                 430
Val Leu Asp Glu Leu Ile Trp Leu Gly Ser Ile Ile Asp Val Ile Leu
        435                 440                 445
Ser Glu Ile Asp Thr Phe Leu Ala Ser Ser Gly Gly Leu Tyr Cys Leu
    450                 455                 460
Gly Gly Gly Cys Gly Asn Val Asp Pro Asp Glu Ser Ala Arg Ile Ser
465                 470                 475                 480
Ser Ala Leu Lys Arg Leu Glu Arg Val Met Arg Leu Ile Lys Leu Asp
            485                 490                 495
Ser Arg Ala Glu Gly Val Arg Thr Leu Leu Trp Thr Phe Ile Lys Ser
        500                 505                 510
Phe Gln Ala Leu Pro Tyr Ile Ala Leu Leu Leu Val Met Leu Glu Glu
    515                 520                 525
Ile Tyr Ala Val Ile Gly Met Met Phe Gly Lys Ile Ala Leu Val Asp
    530                 535                 540
Gly Thr Gln Ile Asn Arg Asn Asn Asn Phe Gln Thr Phe Pro Gln Ala
545                 550                 555                 560
Val Leu Leu Phe Arg Cys Ala Thr Gly Glu Ala Trp Gln Glu Ile
            565                 570                 575
Leu Leu Ala Cys Ser Tyr Gly Lys Leu Cys Asp Pro Glu Ser Asp Tyr
        580                 585                 590
Ala Pro Gly Glu Glu Tyr Thr Cys Gly Thr Asn Phe Ala Tyr Tyr Tyr
    595                 600                 605
Phe Ile Ser Phe Tyr Met Leu Cys Ala Leu Phe Ile Ile Asn Leu Phe
    610                 615                 620
Val Ala Val Phe Met Asp Asn Phe Asp Tyr Leu Thr Arg Asp Trp Ser
625                 630                 635                 640
Ile Leu Gly Pro His His Leu Asp Glu Phe Lys Ala Ile Trp Ala Glu
            645                 650                 655
Tyr Asp Pro Glu Ala Lys Gly Arg Ile Lys His Leu Asp Val Val Thr
        660                 665                 670
Leu Leu Arg Arg Ile Gln Pro Pro Leu Gly Phe Gly Lys Phe Cys Pro
    675                 680                 685
His Arg Val Ala Cys Lys Arg Leu Val Gly Met Asn Met Pro Leu Asn
    690                 695                 700
Ser Asp Gly Thr Val Thr Phe Asn Ala Thr Leu Phe Ala Leu Val Arg
705                 710                 715                 720
Thr Ala Leu Lys Ile Lys Thr Glu Gly Asn Phe Glu Gln Ala Asn Glu
            725                 730                 735
Glu Leu Arg Ala Ile Ile Lys Ile Trp Lys Lys Arg Thr Ser Met Lys
        740                 745                 750
Leu Leu Asp Gln Val Ile Pro Pro Ile Gly Asp Asp Glu Val Thr Val
    755                 760                 765
Gly Lys Phe Tyr Ala Thr Phe Leu Ile Gln Glu His Phe Arg Lys Phe
    770                 775                 780
Met Lys Arg Gln Glu Glu Tyr Tyr Gly
785                 790
```

(2) INFORMATION FOR SEQ ID NO: 5:

```
    (i) SEQUENCE CHARACTERISTICS:
        (A) LENGTH: 26
        (B) TYPE: nucleic acid
        (C) STRANDEDNESS: single
        (D) TOPOLOGY: linear (ii) MOLECULE TYPE: <Unknown>

(ix) FEATURE:
        (A) NAME/KEY: misc_feature
        (B) LOCATION: 6
        (D) OTHER INFORMATION: /note= "inosine"

(ix) FEATURE:
        (A) NAME/KEY: misc_feature
        (B) LOCATION: 12
        (D) OTHER INFORMATION: /note= "inosine"

(ix) FEATURE:
        (A) NAME/KEY: misc_feature
        (B) LOCATION: 21
        (D) OTHER INFORMATION: /note= "inosine"

(xi) SEQUENCE DESCRIPTION: SEQ ID NO: 5:

ATHGYNATGY TNTTYTTYAT NTAYGC                                            26

(2) INFORMATION FOR SEQ ID NO: 6:

(i) SEQUENCE CHARACTERISTICS:
        (A) LENGTH: 26
        (B) TYPE: nucleic acid
        (C) STRANDEDNESS: single
        (D) TOPOLOGY: linear (ii) MOLECULE TYPE: <Unknown>

(ix) FEATURE:
        (A) NAME/KEY: misc_feature
        (B) LOCATION: 6
        (D) OTHER INFORMATION: /note= "inosine"

(ix) FEATURE:
        (A) NAME/KEY: misc_feature
        (B) LOCATION: 15
        (D) OTHER INFORMATION: /note= "inosine"

(ix) FEATURE:
        (A) NAME/KEY: misc_feature
        (B) LOCATION: 18
        (D) OTHER INFORMATION: /note= "inosine"

(ix) FEATURE:
        (A) NAME/KEY: misc_feature
        (B) LOCATION: 21
        (D) OTHER INFORMATION: /note= "inosine"

(xi) SEQUENCE DESCRIPTION: SEQ ID NO: 6:

TCRTCNARRT GRTGNGGNCC NARDAT                                            26

(2) INFORMATION FOR SEQ ID NO: 7:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 2
        (D) OTHER INFORMATION: /note= "any amino acid except proline"

(ix) FEATURE:
```

```
            (A) NAME/KEY: Peptide
            (B) LOCATION: 3
            (D) OTHER INFORMATION: /note= "serine or threonine"

(ix) FEATURE:
            (A) NAME/KEY: Peptide
            (B) LOCATION: 4
            (D) OTHER INFORMATION: /note= "any amino acid except proline"

(xi) SEQUENCE DESCRIPTION: SEQ ID NO: 7:

Asn Xaa Xaa Xaa
1

(2) INFORMATION FOR SEQ ID NO: 8:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1
         (D) OTHER INFORMATION: /note= "arginine or lysine"

(ix) FEATURE:
         (A) NAME/KEY: Peptide
         (B) LOCATION: 2
         (D) OTHER INFORMATION: /note= "any amino acid except proline"

(ix) FEATURE:
         (A) NAME/KEY: Peptide
         (B) LOCATION: 3
         (D) OTHER INFORMATION: /note= "any amino acid except proline"

(ix) FEATURE:
         (A) NAME/KEY: Peptide
         (B) LOCATION: 4
         (D) OTHER INFORMATION: /note= "serine or threonine"

(xi) SEQUENCE DESCRIPTION: SEQ ID NO: 8:

Xaa Xaa Xaa Xaa
1

(2) INFORMATION FOR SEQ ID NO: 9:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1
         (D) OTHER INFORMATION: /note= "serine or threonine"

(ix) FEATURE:
         (A) NAME/KEY: Modified-site
         (B) LOCATION: 2
         (D) OTHER INFORMATION: /note= "any amino acid except proline"

(ix) FEATURE:
         (A) NAME/KEY: Modified-site
         (B) LOCATION: 3
         (D) OTHER INFORMATION: /note= "any amino acid except proline"

(ix) FEATURE:
         (A) NAME/KEY: Modified-site
         (B) LOCATION: 4
```

(D) OTHER INFORMATION: /note= "Aspartic acid or glutamic acid"

(xi) SEQUENCE DESCRIPTION: SEQ ID NO: 9:

Xaa Xaa Xaa Xaa
1

(2) INFORMATION FOR SEQ ID NO: 10:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Met Phe Asp Glu Thr Trp His Lys Phe Asp Val His Gly Thr Gln Phe
1               5                   10                  15

Leu Asp Tyr Asn Asp Leu Pro Arg Phe Val Asn Ala Leu
            20                  25

(2) INFORMATION FOR SEQ ID NO: 11:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Met Phe Tyr Glu Val Trp Glu Lys Phe Asp Pro Asp Ala Thr Gln Phe
1               5                   10                  15

Met Glu Phe Glu Lys Leu Ser Gln Phe Ala Ala Ala Leu
            20                  25

(2) INFORMATION FOR SEQ ID NO: 12:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

Met Phe Tyr Glu Val Trp Glu Lys Phe Asp Pro Asp Ala Thr Gln Phe
1               5                   10                  15

Ile Glu Phe Cys Lys Leu Ser Asp Phe Ala Ala Ala Leu
            20                  25

(2) INFORMATION FOR SEQ ID NO: 13:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Met Phe Tyr Glu Val Trp Glu Lys Phe Asp Pro Asp Ala Thr Gln Phe
1               5                   10                  15

```
Ile Glu Phe Cys Lys Leu Ser Asp Phe Ala Ala Ala Leu
            20                  25
```

(2) INFORMATION FOR SEQ ID NO: 14:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

```
Met Phe Tyr Glu Ile Trp Glu Lys Phe Asp Pro Glu Ala Thr Gln Phe
1               5                   10                  15
Ile Glu Tyr Leu Ala Leu Ser Asp Phe Ala Asp Ala Leu
            20                  25
```

(2) INFORMATION FOR SEQ ID NO: 15:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

```
Met Phe Tyr Glu Thr Trp Glu Lys Phe Asp Pro Asp Ala Thr Gln Phe
1               5                   10                  15
Ile Asp Tyr Ser Arg Leu Ser Asp Phe Val Thr Asp Leu
            20                  25
```

(2) INFORMATION FOR SEQ ID NO: 16:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

```
Lys Ile Ser Tyr Leu Asp Val Leu Leu Ala Val Thr Gln Glu Val Leu
1               5                   10                  15
Gly Asp Thr Thr Glu Met Glu Ala Met Arg Leu Ser Ile
            20                  25
```

(2) INFORMATION FOR SEQ ID NO: 17:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

```
Lys Ile His Cys Leu Asp Ile Leu Phe Ala Leu Thr Lys Glu Val Leu
1               5                   10                  15
Gly Asp Ser Gly Glu Met Asp Ala Leu Lys Gln Thr Met
            20                  25
```

(2) INFORMATION FOR SEQ ID NO: 18:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

```
Glu Phe Lys Arg Ile Trp Ala Glu Tyr Asp Pro Glu Ala Lys Gly Arg
1               5                   10                  15

Ile Lys His Leu Asp Val Val Thr Leu Leu Arg Arg Ile
            20                  25
```

(2) INFORMATION FOR SEQ ID NO: 19:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

```
Glu Phe Lys Lys Ile Trp Ala Glu Tyr Asp Pro Glu Ala Thr Gly Arg
1               5                   10                  15

Ile Lys His Leu Asp Val Val Thr Leu Leu Arg Arg Ile
            20                  25
```

(2) INFORMATION FOR SEQ ID NO: 20:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

```
Glu Phe Lys Arg Ile Trp Ser Glu Tyr Asp Pro Glu Ala Lys Gly Arg
1               5                   10                  15

Ile Lys His Leu Asp Val Val Thr Leu Leu Arg Arg Ile
            20                  25
```

(2) INFORMATION FOR SEQ ID NO: 21:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

```
Glu Phe Lys Ala Ile Trp Ala Glu Tyr Asp Pro Glu Ala Lys Gly Arg
1               5                   10                  15

Ile Lys His Leu Asp Val Val Thr Leu Leu Arg Arg Ile
            20                  25
```

(2) INFORMATION FOR SEQ ID NO: 22:

(i) SEQUENCE CHARACTERISTICS:
            (A) LENGTH: 29 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 22:

Glu Phe Lys Arg Ile Trp Ser Glu Tyr Asp Pro Glu Ala Lys Gly Arg
1               5                   10                  15

Ile Lys His Leu Asp Val Val Thr Leu Leu Arg Arg Ile
                20                  25

(2) INFORMATION FOR SEQ ID NO: 23:

(i) SEQUENCE CHARACTERISTICS:
            (A) LENGTH: 29 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 23:

Glu Phe Ile Arg Leu Trp Ser Glu Tyr Asp Pro Asp Ala Lys Gly Arg
1               5                   10                  15

Ile Lys His Leu Asp Val Val Thr Leu Leu Arg Lys Ile
                20                  25

(2) INFORMATION FOR SEQ ID NO: 24:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (viii) POSITION IN GENOME:
            (A) CHROMOSOME/SEGMENT: calcium channel consensus (Repeat I)

(xi) SEQUENCE DESCRIPTION: SEQ ID NO: 24:

Gln Cys Ile Thr Met Glu Gly Trp Thr Asp Val Leu Tyr
1               5                   10

(2) INFORMATION FOR SEQ ID NO: 25:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (viii) POSITION IN GENOME:
            (A) CHROMOSOME/SEGMENT: calcium channel Drosophila (Repeat I)

(xi) SEQUENCE DESCRIPTION: SEQ ID NO: 25:

Gln Cys Val Thr Leu Glu Gly Trp Thr Asp Val Leu Tyr
1               5                   10

(2) INFORMATION FOR SEQ ID NO: 26:

(i) SEQUENCE CHARACTERISTICS:
            (A) LENGTH: 13 amino acids (B) TYPE: amino acid
            (C) STRANDEDNESS: single
            (D) TOPOLOGY: linear (ii) MOLECULE TYPE: peptide (viii) POSITION IN GENOME:
            (A) CHROMOSOME/SEGMENT: calcium channel Carp Skel (Repeat I)

(xi) SEQUENCE DESCRIPTION: SEQ ID NO: 26:

Gln Cys Ile Thr Thr Glu Ser Trp Thr Asp Val Leu Tyr
1               5                   10

(2) INFORMATION FOR SEQ ID NO: 27:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (viii) POSITION IN GENOME:
            (A) CHROMOSOME/SEGMENT: Ca chan Rab. Skel, Human Br, Rat BrD,
                Rat BrC, Rat Aorta, Rab. Heart, Rat BrB, Rab. Brl, Rat BrA
                (Rpt I)

(xi) SEQUENCE DESCRIPTION: SEQ ID NO: 27:

Gln Val Leu Thr Gly Glu Asp Trp Asn Ser Val Met Tyr
1               5                   10

(2) INFORMATION FOR SEQ ID NO: 28:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (viii) POSITION IN GENOME:
            (A) CHROMOSOME/SEGMENT: calcium channel consensus (Repeat II)

(xi) SEQUENCE DESCRIPTION: SEQ ID NO: 28:

Gln Ile Leu Thr Gly Glu Asp Trp Asn Ser Val Met Tyr
1               5                   10

(2) INFORMATION FOR SEQ ID NO: 29:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (viii) POSITION IN GENOME:
            (A) CHROMOSOME/SEGMENT: Calcium channel Drosophila (Repeat II)

(xi) SEQUENCE DESCRIPTION: SEQ ID NO: 29:

Gln Ile Met Thr Gly Glu Asp Trp Asn Ala Val Met Tyr
1               5                   10

(2) INFORMATION FOR SEQ ID NO: 30:

(i) SEQUENCE CHARACTERISTICS:
            (A) LENGTH: 13 amino acids
            (B) TYPE: amino acid (C) STRANDEDNESS: single
            (D) TOPOLOGY: linear (ii) MOLECULE TYPE: peptide (viii) POSITION IN GENOME:
            (A) CHROMOSOME/SEGMENT: Calcium channel Carp Skel (Repeat II)

(xi) SEQUENCE DESCRIPTION: SEQ ID NO: 30:

Gln Val Leu Thr Gly Glu Glu Trp Asp Ser Ile Met Tyr
1               5                   10

(2) INFORMATION FOR SEQ ID NO: 31:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (viii) POSITION IN GENOME:
            (A) CHROMOSOME/SEGMENT: calcium channel Rabbit Skel
                (Repeat II)

(xi) SEQUENCE DESCRIPTION: SEQ ID NO: 31:

Gln Cys Ile Thr Met Glu Gly Trp Thr Asp Val Leu Tyr
1               5                   10

(2) INFORMATION FOR SEQ ID NO: 32:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (viii) POSITION IN GENOME:
            (A) CHROMOSOME/SEGMENT: calcium channel Human brain and Rat
                Br-D (Repeat II)

(xi) SEQUENCE DESCRIPTION: SEQ ID NO: 32:

Gln Ile Leu Thr Gly Glu Asp Trp Asn Ala Val Met Tyr
1               5                   10

(2) INFORMATION FOR SEQ ID NO: 33:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (viii) POSITION IN GENOME:
            (A) CHROMOSOME/SEGMENT: calcium channel Rat Br-C, Rat Aorta,
                Rab. Heart, Rat Br-B, Rab. Br-1, Rat Br-A (Repeat II)

(xi) SEQUENCE DESCRIPTION: SEQ ID NO: 33:

Gln Ile Leu Thr Gly Glu Asp Trp Asn Ser Val Met Tyr
1               5                   10

(2) INFORMATION FOR SEQ ID NO: 34:

(i) SEQUENCE CHARACTERISTICS:
            (A) LENGTH: 13 amino acids
            (B) TYPE: amino acid

```
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel consensus (Repeat I)

(xi) SEQUENCE DESCRIPTION: SEQ ID NO: 34:

Arg Leu Met Thr Gln Asp Tyr Trp Glu Asn Leu Tyr Gln
1               5                   10

(2) INFORMATION FOR SEQ ID NO: 35:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel para, Rat BrII, Rat
            BrIII, Rat Heart, Rat Skel mu1, Eel (Repeat I)

(xi) SEQUENCE DESCRIPTION: SEQ ID NO: 35:

Arg Leu Met Thr Gln Asp Phe Trp Glu Asp Leu Tyr Gln
1               5                   10

(2) INFORMATION FOR SEQ ID NO: 36:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel consensus (Repeat II)

(xi) SEQUENCE DESCRIPTION: SEQ ID NO: 36:

Arg Val Leu Cys Gly Glu Trp Ile Glu Thr Met Trp Asp
1               5                   10

(2) INFORMATION FOR SEQ ID NO: 37:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel para (Repeat II)

(xi) SEQUENCE DESCRIPTION: SEQ ID NO: 37:

Arg Val Leu Cys Gly Glu Trp Ile Glu Ser Met Trp Asp
1               5                   10

(2) INFORMATION FOR SEQ ID NO: 38:

(i) SEQUENCE CHARACTERISTICS:
        (A) LENGTH: 13 amino acids
        (B) TYPE: amino acid
        (C) STRANDEDNESS: single
        (D) TOPOLOGY: linear
```

(ii) MOLECULE TYPE: peptide (viii) POSITION IN GENOME:
            (A) CHROMOSOME/SEGMENT: sodium channel Rat BrII, Rat BrIII
            (Repeat II)

(xi) SEQUENCE DESCRIPTION: SEQ ID NO: 38:

Arg Val Leu Cys Gly Glu Trp Ile Glu Ser Met Trp Asp
1               5                  10

(2) INFORMATION FOR SEQ ID NO: 39:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (viii) POSITION IN GENOME:
            (A) CHROMOSOME/SEGMENT: sodium channel Rat Heart, Rat Skel mu1
            (Repeat II)

(xi) SEQUENCE DESCRIPTION: SEQ ID NO: 39:

Arg Ile Leu Cys Gly Glu Trp Ile Glu Ser Met Trp Asp
1               5                  10

(2) INFORMATION FOR SEQ ID NO: 40:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (viii) POSITION IN GENOME:
            (A) CHROMOSOME/SEGMENT: sodium channel Eel (Repeat II)

(xi) SEQUENCE DESCRIPTION: SEQ ID NO: 40:

Arg Ala Leu Cys Gly Glu Trp Ile Glu Ser Met Trp Asp
1               5                  10

(2) INFORMATION FOR SEQ ID NO: 41:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (viii) POSITION IN GENOME:
            (A) CHROMOSOME/SEGMENT: calcium channel consensus (Repeat III)

(xi) SEQUENCE DESCRIPTION: SEQ ID NO: 41:

Thr Val Ser Thr Phe Glu Gly Trp Pro Glu Leu Leu Tyr
1               5                  10

(2) INFORMATION FOR SEQ ID NO: 42:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (viii) POSITION IN GENOME:
          (A) CHROMOSOME/SEGMENT: calcium channel Drosophila
              (Repeat III)

(xi) SEQUENCE DESCRIPTION: SEQ ID NO: 42:

Thr Val Ser Thr Phe Glu Gly Trp Pro Gly Leu Leu Tyr
1               5                  10

(2) INFORMATION FOR SEQ ID NO: 43:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (viii) POSITION IN GENOME:
          (A) CHROMOSOME/SEGMENT: calcium channel Carp Skel (Repeat III)

(xi) SEQUENCE DESCRIPTION: SEQ ID NO: 43:

Thr Ile Ser Thr Phe Glu Gly Trp Pro Glu Ile Leu Tyr
1               5                  10

(2) INFORMATION FOR SEQ ID NO: 44:

(i) SEQUENCE CHARACTERISTICS:
         (A) LENGTH: 14 amino acids
         (B) TYPE: amino acid
         (C) STRANDEDNESS: single
         (D) TOPOLOGY: linear (ii) MOLECULE TYPE: peptide (viii) POSITION IN GENOME:
          (A) CHROMOSOME/SEGMENT: Ca chan Rab. Skel, Human Br, Rat BrD,
              Rat BrC, Rat Aorta, Rab Heart, Rat BrB, Rabbit Br1, Rat
              BrA (Repeat III)

(xi) SEQUENCE DESCRIPTION: SEQ ID NO: 44:

Thr Val Ile Ser Thr Phe Glu Gly Trp Pro Glu Ile Leu Tyr
1               5                  10

(2) INFORMATION FOR SEQ ID NO: 45:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (viii) POSITION IN GENOME:
          (A) CHROMOSOME/SEGMENT: calcium channel consensus (Repeat IV)

(xi) SEQUENCE DESCRIPTION: SEQ ID NO: 45:

Arg Cys Ala Thr Gly Glu Ala Trp Gln Glu Ile Met Leu
1               5                  10

(2) INFORMATION FOR SEQ ID NO: 46:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (viii) POSITION IN GENOME:
            (A) CHROMOSOME/SEGMENT: calcium channel Drosophila (Repeat IV)

(xi) SEQUENCE DESCRIPTION: SEQ ID NO: 46:

Arg Ser Ala Thr Gly Glu Ala Trp Glu Ile Met Met
1               5                   10

(2) INFORMATION FOR SEQ ID NO: 47:

(i) SEQUENCE CHARACTERISTICS:
             (A) LENGTH: 13 amino acids
             (B) TYPE: amino acid
             (C) STRANDEDNESS: single
             (D) TOPOLOGY: linear (ii) MOLECULE TYPE: peptide (viii) POSITION IN GENOME:
            (A) CHROMOSOME/SEGMENT: calcium channel Carp Skel (Repeat IV)

(xi) SEQUENCE DESCRIPTION: SEQ ID NO: 47:

Arg Val Ala Thr Gly Glu Gln Trp Pro Lys Val Ile Leu
1               5                   10

(2) INFORMATION FOR SEQ ID NO: 48:

(i) SEQUENCE CHARACTERISTICS:
             (A) LENGTH: 13 amino acids
             (B) TYPE: amino acid
             (C) STRANDEDNESS: single
             (D) TOPOLOGY: linear (ii) MOLECULE TYPE: peptide (viii) POSITION IN GENOME:
            (A) CHROMOSOME/SEGMENT: Ca chan Rab. Skel, Human Br, Rat BrD,
                Rat BrC, Rat Aorta, Rab. Heart, Rat BrB, Rab. Br1, Rat BrA
                (Repeat IV)

(xi) SEQUENCE DESCRIPTION: SEQ ID NO: 48:

Arg Cys Ala Thr Gly Glu Gln Trp Pro Lys Val Ile Leu
1               5                   10

(2) INFORMATION FOR SEQ ID NO: 49:

(i) SEQUENCE CHARACTERISTICS:
             (A) LENGTH: 13 amino acids
             (B) TYPE: amino acid
             (C) STRANDEDNESS: single
             (D) TOPOLOGY: linear (ii) MOLECULE TYPE: peptide (viii) POSITION IN GENOME:
            (A) CHROMOSOME/SEGMENT: sodium channel consensus (Repeat III)

(xi) SEQUENCE DESCRIPTION: SEQ ID NO: 49:

Gln Val Ala Thr Phe Lys Gly Trp Met Asp Ile Met Tyr
1               5                   10

(2) INFORMATION FOR SEQ ID NO: 50:

(i) SEQUENCE CHARACTERISTICS:
             (A) LENGTH: 13 amino acids
             (B) TYPE: amino acid
             (C) STRANDEDNESS: single
             (D) TOPOLOGY: linear (ii) MOLECULE TYPE: peptide (viii) POSITION IN GENOME:
        (A) CHROMOSOME/SEGMENT: sodium channel para, Rat BrII, Rat
            BrIII, Rat Heart (Repeat III)

(xi) SEQUENCE DESCRIPTION: SEQ ID NO: 50:

Gln Val Ala Thr Phe Lys Gly Trp Ile Gln Ile Met Asn
1               5                   10

(2) INFORMATION FOR SEQ ID NO: 51:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel Rat Skel mu1
            (Repeat III)

(xi) SEQUENCE DESCRIPTION: SEQ ID NO: 51:

Gln Val Ala Thr Phe Lys Gly Trp Met Asp Ile Met Tyr
1               5                   10

(2) INFORMATION FOR SEQ ID NO: 52:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel Eel (Repeat III)

(xi) SEQUENCE DESCRIPTION: SEQ ID NO: 52:

Gln Val Ser Thr Phe Lys Gly Trp Met Asp Ile Met Tyr
1               5                   10

(2) INFORMATION FOR SEQ ID NO: 53:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel consensus (Repeat IV)

(xi) SEQUENCE DESCRIPTION: SEQ ID NO: 53:

Gln Ile Thr Thr Ser Ala Gly Trp Asp Gly Ile Leu Ala
1               5                   10

(2) INFORMATION FOR SEQ ID NO: 54:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide -continued

```
    (viii) POSITION IN GENOME:
          (A) CHROMOSOME/SEGMENT: sodium channel para (Repeat IV)

(xi) SEQUENCE DESCRIPTION: SEQ ID NO: 54:

Gln Met Ser Thr Ser Ala Gly Trp Asp Gly Val Leu Asp
1               5                   10

(2) INFORMATION FOR SEQ ID NO: 55:

(i) SEQUENCE CHARACTERISTICS:
          (A) LENGTH: 13 amino acids
          (B) TYPE: amino acid
          (C) STRANDEDNESS: single
          (D) TOPOLOGY: linear (ii) MOLECULE TYPE: peptide (viii) POSITION IN GENOME:
          (A) CHROMOSOME/SEGMENT: sodium channel Rat BrII, Rat BrIII,
              Rat Heart (Repeat IV)

(xi) SEQUENCE DESCRIPTION: SEQ ID NO: 55:

Gln Ile Ser Thr Ser Ala Gly Trp Asp Gly Val Leu Asp
1               5                   10

(2) INFORMATION FOR SEQ ID NO: 56:

(i) SEQUENCE CHARACTERISTICS:
          (A) LENGTH: 13 amino acids
          (B) TYPE: amino acid
          (C) STRANDEDNESS: single
          (D) TOPOLOGY: linear (ii) MOLECULE TYPE: peptide (viii) POSITION IN GENOME:
          (A) CHROMOSOME/SEGMENT: sodium channel Rat Skel mu1
              (Repeat IV)

(xi) SEQUENCE DESCRIPTION: SEQ ID NO: 56:

Glu Ile Thr Thr Ser Ala Gly Trp Asp Gly Leu Leu Asn
1               5                   10

(2) INFORMATION FOR SEQ ID NO: 57:

(i) SEQUENCE CHARACTERISTICS:
          (A) LENGTH: 13 amino acids
          (B) TYPE: amino acid
          (C) STRANDEDNESS: single
          (D) TOPOLOGY: linear (ii) MOLECULE TYPE: peptide (viii) POSITION IN GENOME:
          (A) CHROMOSOME/SEGMENT: sodium channel Eel (Repeat IV)

(xi) SEQUENCE DESCRIPTION: SEQ ID NO: 57:

Glu Ile Thr Thr Ser Ala Gly Trp Asp Gly Leu Leu Leu
1               5                   10
```